(12) United States Patent
West et al.

(10) Patent No.: US 8,679,550 B2
(45) Date of Patent: Mar. 25, 2014

(54) MORINDA CITRIFOLIA JUICE FORMULATIONS COMPRISING IRIDOIDS

(75) Inventors: Brett Justin West, Cedar Hills, UT (US); Claude Jarakae Jensen, Cedar Hills, UT (US); Afa Kehaati Palu, American Fork, UT (US); Shixin Deng, Lehi, UT (US); Jeffery A. Wasden, Springville, UT (US)

(73) Assignee: Tahitian Noni International, Inc., Provo, UT (US)

( * ) Notice: Subject to any disclaimer, the term of this patent is extended or adjusted under 35 U.S.C. 154(b) by 57 days.

(21) Appl. No.: 13/406,253

(22) Filed: Feb. 27, 2012

(65) Prior Publication Data

US 2012/0328720 A1 Dec. 27, 2012

Related U.S. Application Data

(60) Continuation-in-part of application No. 13/032,530, filed on Feb. 22, 2011, which is a continuation-in-part of application No. 11/034,505, filed on Jan. 13, 2005, and a continuation-in-part of application No. 10/396,868, filed on Mar. 25, 2003, now abandoned, said application No. 13/032,530 is a continuation-in-part of application No. 11/360,550, filed on Feb. 23, 2006, now abandoned, which is a division of application No. 10/285,359, filed on Oct. 31, 2002, now Pat. No. 7,033,624, said application No.

(Continued)

(51) Int. Cl.
*A61K 36/00* (2006.01)
*A61K 36/45* (2006.01)
*A61K 36/87* (2006.01)
*A61K 36/40* (2006.01)

(52) U.S. Cl.
USPC ........... 424/725; 424/732; 424/766; 424/771; 426/648

(58) Field of Classification Search
USPC .................. 424/725, 732, 766, 771; 426/648
See application file for complete search history.

(56) References Cited

U.S. PATENT DOCUMENTS

2004/0137094 A1* 7/2004 Mower et al. .................. 424/769
2008/0089941 A1* 4/2008 Mower .......................... 424/489

(Continued)

OTHER PUBLICATIONS

Nuriche: PhytoChargeTM—Dietary Supplement, Online, URL<http://web.archive.org/web/20100910053441/http://www.nuriche.com/products/naturals/powders/powders-ingredients/> Archived to Sep. 10, 2013.*

*Primary Examiner* — Patricia Leith
(74) *Attorney, Agent, or Firm* — Kirton McConkie; Michael F. Krieger

(57) ABSTRACT

Fortified food and dietary supplement products may be administered to produce desirable physiological improvement. In particular, embodiments of the invention relates to the administration of products enhanced with plant products and iridoids. A study was performed to evaluate the iridoid content, as well as the in vitro and in vivo bioactivities, of a beverage containing noni fruit, Cornelian cherries, and olive leaf extract. The major iridoids present were identified as asperulosidic acid, deacetylasperulosidic acid, oleuropein, morroniside, loganic acid, and loganin In the 2,2-Diphenylpicrylhydrazyl (DPPH) radical scavenging assay, remarkably high in vitro antioxidant activity was observed, with an $IC_{50}$ of 3.8 μL/mL. In vivo bioactivities were evaluated in type 2 diabetic Sprague Dawley rats. In a dose-dependent manner, the composition reduced abnormal weight gain, blood glucose levels, and serum advanced glycation end products (AGEs), as well as improved immunity via increased T cell counts and $CD4+/CD8^+$ ratios.

3 Claims, 8 Drawing Sheets

Table 3. Mean percentage, ± standard deviation, of T cells subsets and CD4+/CD8+ ratio by treatment group.

| Group | $CD3^+$% | $CD4^+$ % | $CD8^+$ % | $CD4^+/CD8^+$ |
|---|---|---|---|---|
| Normal control | 54.5 ± 5.49 | 49.6 ± 8.22 | 29.9 ± 5.38 | 1.71 ± 0.45 |
| Diabetic control | 37.9 ± 6.50** | 30.3 ± 6.70** | 39.1 ± 5.19** | 0.75 ± 0.254** |
| Low dose | 40.4 ± 7.72** | 32.5 ± 7.07** | 37.1 ± 4.42** | 0.91 ± 0.301** |
| Mid dose | 43.5 ± 6.87** | 39.2 ± 5.08** ## | 35.2 ± 3.11* | 1.13 ± 0.229** ## |
| High dose | 46.7 ± 8.75* # | 44.0 ± 8.77## | 32.8 ± 6.27# | 1.43 ± 0.512## |

* $p < 0.05$, ** $p < 0.01$; compared to normal controls

$p < 0.05$, ## $p < 0.01$; compared to diabetic controls

Related U.S. Application Data

11/360,550 is a continuation-in-part of application No. 10/006,014, filed on Dec. 4, 2001, now abandoned, said application No. 13/032,530 is a continuation-in-part of application No. 11/553,323, filed on Oct. 26, 2006, now abandoned, which is a division of application No. 10/993,883, filed on Nov. 19, 2004, now Pat. No. 7,186,422, which is a division of application No. 10/286,167, filed on Nov. 1, 2002, now Pat. No. 6,855,345.

(60) Provisional application No. 61/307,262, filed on Feb. 23, 2010, provisional application No. 60/536,663, filed on Jan. 15, 2004, provisional application No. 60/552,144, filed on Mar. 10, 2004, provisional application No. 60/335,343, filed on Nov. 2, 2001, provisional application No. 60/251,416, filed on Dec. 5, 2000, provisional application No. 60/335,313, filed on Nov. 2, 2001.

(56) References Cited

U.S. PATENT DOCUMENTS

2010/0215783 A1* 8/2010 McNeary ............... 424/732
2011/0206721 A1* 8/2011 Nair ................... 424/195.15

* cited by examiner

Iridoid

Non-Glycosidic Iridoid

Secoiridoid

Glycosidic Iridoid deacetylasperulosidic acid (DAA): R = H
asperulsidic acid (AA): R = Ac Table 1. Mean weight (g), ± standard deviation, of treatment groups by week.

| Group | Initial | Week 2 | Week 4 | Week 5 |
|---|---|---|---|---|
| Normal control | 214 ± 10.9 | 268 ± 10.1 | 330 ± 13.0 | 363 ± 13.1 |
| Diabetic control | 214 ± 10.2 | 291 ± 11.8** | 368 ± 13.8** | 408 ± 14.0** |
| Low dose | 214 ± 11.2 | 283 ± 11.6** | 353 ± 12.1**# | 398 ± 14.0** |
| Mid dose | 214 ± 10.3 | 278 ± 11.5# | 343 ± 11.6*## | 396 ± 12.4**## |
| High dose | 214 ± 10.7 | 275 ± 12.1# | 340 ± 13.2## | 381 ± 12.2**## |

* $p < 0.05$, ** $p < 0.01$; compared to normal controls

$p < 0.05$, ## $p < 0.01$; compared to diabetic controls

FIG. 7

Table 2. Mean blood glucose, ± standard deviation, and percentage of animals categorized as diabetic (% DM) by glucose level, at 0 and 2 hours after glucose challenge.

| Group | 0 Hour Glucose (mmol/L) | % DM | 2 Hours Glucose (mmol/L) | % DM |
|---|---|---|---|---|
| Normal control | 4.32 ± 0.39 | 0 | 6.28 ± 0.53 | 0 |
| Diabetic control | 7.93 ± 0.57* | 100 | 12.1 ± 0.58* | 100 |
| Low dose | 6.90 ± 0.57* ## | 50 | 11.3 ± 0.91* # | 60 |
| Mid dose | 6.48 ± 0.46* ## | 20 | 10.7 ± 0.68* ## | 30 |
| High dose | 6.16 ± 0.47* ## | 0 | 10.2 ± 0.55* ## | 0 |

* $p < 0.01$; compared to normal controls

$p < 0.05$, ## $p < 0.01$; compared to diabetic controls

FIG. 8

Table 3. Mean percentage, ± standard deviation, of T cells subsets and CD4+/CD8+ ratio by treatment group.

| Group | CD3$^+$% | CD4$^+$ % | CD8$^+$ % | CD4$^+$/CD8$^+$ |
|---|---|---|---|---|
| Normal control | 54.5 ± 5.49 | 49.6 ± 8.22 | 29.9 ± 5.38 | 1.71 ± 0.45 |
| Diabetic control | 37.9 ± 6.50** | 30.3 ± 6.70** | 39.1 ± 5.19** | 0.75 ± 0.254** |
| Low dose | 40.4 ± 7.72** | 32.5 ± 7.07** | 37.1 ± 4.42** | 0.91 ± 0.301** |
| Mid dose | 43.5 ± 6.87** | 39.2 ± 5.08** ## | 35.2 ± 3.11* | 1.13 ± 0.229** ## |
| High dose | 46.7 ± 8.75* # | 44.0 ± 8.77## | 32.8 ± 6.27# | 1.43 ± 0.512## |

* $p < 0.05$, ** $p < 0.01$; compared to normal controls

$p < 0.05$, ## $p < 0.01$; compared to diabetic controls

FIG. 9

Table 4. Mean AGE level, ± standard deviation, by treatment group.

| Group | AGE (pg/mL) |
|---|---|
| Normal control | 26.4 ± 3.74 |
| Diabetic control | 36.9 ± 4.67 ** |
| Low dose | 32.7 ± 4.26 ** |
| Mid dose | 31.4 ± 4.32 * # |
| High dose | 30.1 ± 5.19 ## |

*$p < 0.05$, ** $p < 0.01$; compared to normal controls

$p < 0.05$, ## $p < 0.01$; compared to diabetic controls

FIG. 10

MORINDA CITRIFOLIA JUICE FORMULATIONS COMPRISING IRIDOIDS

PRIORITY CLAIM

This application is a continuation in part which claims priority to U.S. patent application Ser. No. 13/032,530 filed Feb. 22, 2011 which claims priority to U.S. Provisional Patent Application No. 61/307,262, filed Feb. 23, 2010 and is a is a continuation in part of U.S. patent Ser. No. 11/034,505, filed Jan. 13, 2005, entitled "Profiles of Lipid Proteins and Inhibiting HMG-COA Reductase," which claims priority to Provisional Application No. 60/536,663, filed Jan. 15, 2004 and claims priority to Provisional Application No. 60/552,144, filed Mar. 10, 2004, is a continuation-in-part of U.S. Pat. No. 6,737,089, filed Apr. 17, 2001, entitled "*Morinda Citrifolia* (Noni) Enhanced Animal Food Product", and is a continuation-in-part of U.S. Pat. No. 7,244,463, filed Oct. 18, 2001, entitled "Garcinia Mangostana L. Enhanced Animal Food Product" and is a continuation-in-part of U.S. patent application Ser. No. 10/396,868, filed Mar. 25, 2003, entitled "Preventative And Treatment Effects Of Morinda Citirifolia As An Aromatase Inhibitor" and is a continuation-in-part of U.S. patent application Ser. No. 11/360,550 filed Feb. 23, 2006, entitled "Preventative and Treatment Effects of *Morinda Citrifolia* on Osteoarthritis and Its Related Conditions" which is a divisional of U.S. patent application Ser. No. 10/285,359, now U.S. Pat. No. 7,033,624, filed Oct. 31, 2002, entitled "Preventative and Treatment Effects of *Morinda Citrifolia* on Osteoarthritis and Its Related Conditions" which claims priority to U.S. Provisional Patent Application No. 60/335,343 filed Nov. 2, 2001, entitled, "Methods for Treating Osteoarthritis" and is a continuation-in-part of U.S. patent application Ser. No. 10/006,014 filed Dec. 4, 2001, entitled "Tahitian Noni Juice On Cox-1 And Cox-2 And Tahitian Noni Juice As A Selective Cox-2 Inhibitor", which claims priority to U.S. Provisional Patent Application Ser. No. 60/251,416 filed Dec. 5, 2000, entitled "Cox-1 and Cox-2 Inhibition Study on TNJ" and is a continuation-in-part of U.S. patent application Ser. No. 11/553,323, filed Oct. 26, 2006, entitled "Preventative and Treatment Effects of *Morinda Citrifolia* on Diabetes and its Related Conditions" which is a divisional of U.S. patent application Ser. No. 10/993,883, now U.S. Pat. No. 7,186,422 filed Nov. 19, 2004, entitled "Preventative And Treatment Effects Of *Morinda Citrifolia* On Diabetes And Its Related Conditions" which is a divisional of U.S. application Ser. No. 10/286,167, now U.S. Pat. No. 6,855,345 filed Nov. 1, 2002, entitled "Preventative And Treatment Effects Of *Morinda Citrifolia* On Diabetes And Its Related Conditions," which claims priority to U.S. Provisional Application Ser. No. 60/335,313, filed Nov. 2, 2001, and entitled, "Methods for Treating Conditions Related to Diabetes."

BACKGROUND

1. Field of Invention

Embodiments of the invention relate to fortified food and dietary supplement products which may be administered to produce desirable physiological improvement. In particular, embodiments of the invention relates to the administration of products enhanced with iridoids.

2. Background

Nutraceuticals may generally be defined as dietary products fortified to provide health and medical benefits, including the prevention and treatment of disease. Nutraceutical products include a wide range of goods including isolated nutrients, dietary supplements, herbal products, processed foods and beverages. With recent breakthroughs in cellular-level nutraceuticals agents, researchers, and medical practitioners are developing therapies complimentary therapies into responsible medical practice and maintenance of good health. Generally, nutraceutical include a product isolated or purified from foods, and are generally sold in forms that demonstrate a physiological benefit or provide protection against chronic disease.

There are multiple types of products that fall under the category of nutraceuticals. Nutraceuticals may be manufactured as dietary supplements, functional foods or medical product. A dietary supplement is a product that contains nutrients derived from food products that are concentrated in liquid, powder or capsule form. A dietary supplement is a product taken by mouth that contains a dietary ingredient intended to supplement the diet. Dietary ingredients in these products may include: vitamins, minerals, herbs or other botanicals, and substances such as enzymes and metabolites. Dietary supplements can also be extracts or concentrates, and may be found in many forms such as tablets capsules, softgels, gelcaps, liquides or powders.

Functional foods include ordinary food that has components or ingredients added to give it a specific medical or physiological benefit, other than a purely nutritional effect. Functional foods may be designed to allow consumers to eat enriched foods close to their natural state, rather than by taking dietary supplements manufactured in liquid or capsule form. Functional foods may be produced in their naturally-occurring form, rather than a capsule, tablet, or powder, can be consumed in the diet as often as daily, and may be used to regulate a biological process in hopes of preventing or controlling disease.

SUMMARY OF THE INVENTION

Some embodiments relate to formulations that provide a specific physiological benefit. Some embodiments relate to formulations designed to prevent or control disease. Some embodiments comprise a processed plant products and a source of iridoids and methods for manufacturing same.

Some embodiments provide a processed plant product selected from a group consisting of: extract from the leaves of the selected plant, leaf hot water extract, processed leaf ethanol extract, processed leaf steam distillation extract, fruit juice, plant extract, dietary fiber, puree juice, plant puree, fruit juice concentrate, plant puree juice concentrate, freeze concentrated fruit juice, seeds, seed extracts, extracts from defatted seeds and evaporated concentration of fruit juice, in combination with an amount of iridoids sourced from at least one of a variety of plants.

Preferred embodiments are formulated to provide a physiological benefit. For example some embodiments may selectively inhibit COX-1/COX-2, regulate TNF and Nitric oxide and 5-LOX, increases IFN-secretion, inhibit histamine release, inhibit human neutrophils, regulate elastase enzyme activity, inhibit the complement pathway, inhibit the growth microbials including gram– and gram+ bacteria, inhibit DNA repair systems, inhibit cancer cell growth & cytotoxic to cancer cells, inhibit platelet aggregations, provide DPPH scavenging effects, provide antiviral activity including anti-HSV, anti-RSV, and anti-VSV activity, provide antispasmodic activity, provide wound-healing and neuroprotective activities, reduce abnormal weight gain, moderate blood glucose levels, provide heightened immune system responses, provide anti oxydents and serum advanced glycation end products are improved via increased T cell counts and CD4+/CD8+ ratios.

BRIEF DESCRIPTION OF THE DRAWINGS

In order that the matter in which the above-recited and other advantages of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 7 depicts Table 1, the mean weight of treatment groups by week;

FIG. 8 depicts Table 2, the mean blood glucose in animals categorized as diabetic at 0 and 2 hours after glucose challenge;

FIG. 9 depicts Table 3 the mean percentage of Tcells subjects and CD4+/CD8+ ratio by treatment group; and FIG. 10 depicts Table 4, the mean AGE level by treatment group.

DETAILED DESCRIPTION OF THE INVENTION

Figure 1:
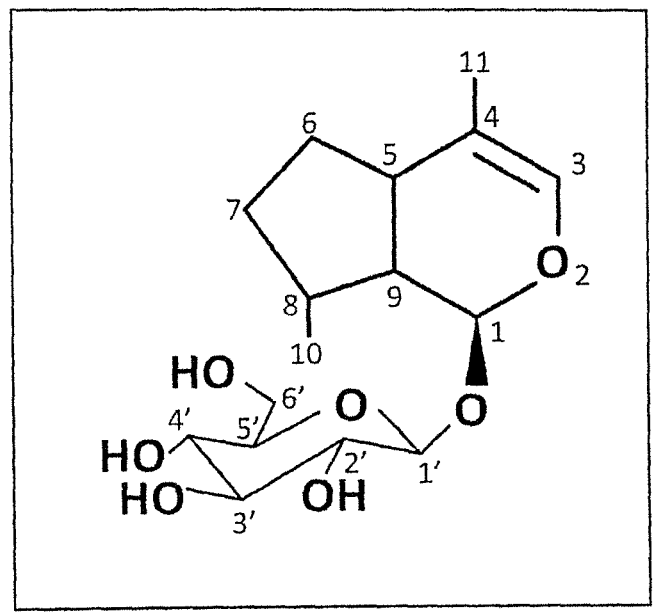
FIG. 1 depicts the structural formula for common iridoids according to some embodiments of the invention.
Figure 1:
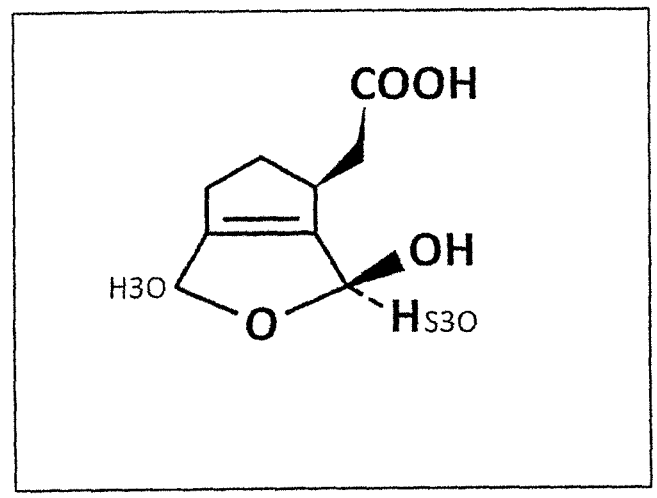

It will be readily understood that the components of the present invention, as generally described herein, could be arranged and designed in a wide variety of different configurations. Thus, the following more detailed description of embodiments of the compositions and methods of the present invention is not intended to limit the scope of the invention, as claimed, but is merely representative of the presently preferred embodiments of the invention. The scope of the invention is, therefore, indicated by the appended claims rather than by the foregoing description. All changes that come within the meaning and range of equivalency of the claims are to be embraced within their scope.

Embodiments of the present invention feature methods and compositions designed to provide a physiological benefit comprising a combination of a processed plant product and a source of iridoids. The physiological benefit arising from the synergistic combination of a component derived from the selected plant and a source of iridoids.

Embodiments of the present invention comprise plant compositions, each of which include one or more processed plant products. The plant product preferably includes plant fruit juice, which juice is preferably present in an amount capable of maximizing the desired physiological benefit without causing negative side effects when the composition is administered to a mammal. Products from the selected plant may include one more parts of the plant, including but not limited to the: fruit, including the fruit juice and fruit pulp and concentrates thereof, leaves, including leaf extract, seeds, including the seed oil, flowers, roots, bark, and wood.

Some compositions of the present invention comprise plant extracts present between about 1 and 5 percent of the weight of the total composition. Other such percentage ranges include: about 0.1 and 50 percent; about 85 and 99 percent; about 5 and 10 percent; about 10 and 15 percent; about 15 and 20 percent; about 20 and 50 percent; and about 50 and 100 percent.

In some plant compositions of the present invention, plant fruit juice evaporative concentrate is present, the evaporative concentrate having a concentration strength (described further herein) between about 8 and 12 percent. Other such percentage ranges include: about 4 and 12 percent; and about 0.5 and 12 percent.

In some plant compositions of the present invention, fruit juice freeze concentrate is present, the freeze concentrate having a concentration strength (described further herein) between about 4 and 6 percent. Other such percentage ranges include: about 0.5 and 2 percent; and about 0.5 and 6 percent.

One or more plant extracts can be further combined with other ingredients or carriers (discussed further herein) to produce a pharmaceutical plant product or composition ("pharmaceutical" herein referring to any drug or product designed to improve the health of living organisms such as human beings or mammals, including nutraceutical products) that is also a plant of the present invention. Examples of pharmaceutical plant products may include, but are not limited to, orally administered solutions and intravenous solutions.

Methods of the present invention also include the obtaining of plant compositions and extracts, including fruit juice and concentrates thereof. It will be noted that some of the embodiments of the present invention contemplate obtaining fruit juice pre-made. Various methods of the present invention shall be described in more detail further herein.

The following disclosure of the present invention is grouped into subheadings. The utilization of the subheadings is for convenience of the reader only and is not to be construed as limiting in any sense.

Processing the Selected Plant Leaves

The leaves of the selected plant are one possible component of the plant that may be present in some compositions of the present invention. For example, some compositions comprise leaf extract and/or leaf juice as described further herein. Some compositions comprise a leaf serum that is comprised of both leaf extract and fruit juice obtained from the selected plant. Some compositions of the present invention comprise leaf serum and/or various leaf extracts as incorporated into a nutraceutical product ("nutraceutical" herein referring to any product designed to improve the health of living organisms such as human beings or mammals).

In some embodiments of the present invention, the leaf extracts are obtained using the following process. First, relatively dry leaves from the selected plant are collected, cut into small pieces, and placed into a crushing device—preferably a hydraulic press—where the leaf pieces are crushed. In some embodiments, the crushed leaf pieces are then percolated with an alcohol such as ethanol, methanol, ethyl acetate, or other alcohol-based derivatives using methods known in the art. Next, in some embodiments, the alcohol and all alcohol-soluble ingredients are extracted from the crushed leaf pieces, leaving a leaf extract that is then reduced with heat to remove all the liquid therefrom. The resulting dry leaf extract will herein be referred to as the "primary leaf extract."

In some embodiments, the primary leaf extract is subsequently pasteurized. The primary leaf extract may be pasteurized preferably at a temperature ranging from 70 to 80 degrees Celsius and for a period of time sufficient to destroy any objectionable organisms without major chemical alteration of the extract. Pasteurization may also be accomplished according to various radiation techniques or methods.

In some embodiments of the present invention, the pasteurized primary leaf extract is placed into a centrifuge decanter where it is centrifuged to remove or separate any remaining leaf juice therein from other materials, including chlorophyll. Once the centrifuge cycle is completed, the leaf extract is in a relatively purified state. This purified leaf extract is then pasteurized again in a similar manner as discussed above to obtain a purified primary leaf extract.

Preferably, the primary leaf extract, whether pasteurized and/or purified, is further fractionated into two individual fractions: a dry hexane fraction, and an aqueous methanol fraction. This is accomplished preferably in a gas chromatograph containing silicon dioxide and CH2Cl2-MeOH ingredients using methods well known in the art. In some embodiments of the present invention, the methanol fraction is further fractionated to obtain secondary methanol fractions. In some embodiments, the hexane fraction is further fractionated to obtain secondary hexane fractions.

One or more of the leaf extracts, including the primary leaf extract, the hexane fraction, methanol fraction, or any of the secondary hexane or methanol fractions may be combined with the fruit juice of the fruit of the selected plant to obtain a leaf serum (the process of obtaining the fruit juice to be described further herein). In some embodiments, the leaf serum is packaged and frozen ready for shipment; in others, it is further incorporated into a nutraceutical product as explained herein.

Processing the Selected Fruit

Some embodiments of the present invention include a composition comprising fruit juice of the selected plant. In some embodiments the fruit may be processed in order to make it palatable for human consumption and included in the compositions of the present invention. Processed fruit juice can be prepared by separating seeds and peels from the juice and pulp of a ripened fruit; filtering the pulp from the juice; and packaging the juice. Alternatively, rather than packaging the juice, the juice can be immediately included as an ingredient in another product, frozen or pasteurized. In some embodiments of the present invention, the juice and pulp can be pureed into a homogenous blend to be mixed with other ingredients. Other processes include freeze drying the fruit and juice. The fruit and juice can be reconstituted during production of the final juice product. Still other processes may include air drying the fruit and juices prior to being masticated.

In a currently preferred process of producing fruit juice, the fruit is either hand picked or picked by mechanical equipment. The fruit can be harvested when it is at least one inch (2-3 cm) and up to 12 inches (24-36 cm) in diameter. The fruit preferably has a color ranging from a dark green through a yellow-green up to a white color, and gradations of color in between. The fruit is thoroughly cleaned after harvesting and before any processing occurs.

The fruit is allowed to ripen or age from 0 to 14 days, but preferably for 2 to 3 days. The fruit is ripened or aged by being placed on equipment so that the fruit does not contact the ground. The fruit is preferably covered with a cloth or netting material during aging, but the fruit can be aged without being covered.

The ripened and aged fruit is preferably placed in plastic lined containers for further processing and transport. The containers of aged fruit can be held from 0 to 30 days, but preferably the fruit containers are held for 7 to 14 days before processing. The containers can optionally be stored under refrigerated conditions prior to further processing. The fruit is unpacked from the storage containers and is processed through a manual or mechanical separator. The seeds and peel are separated from the juice and pulp.

The juice and pulp can be packaged into containers for storage and transport. Alternatively, the juice and pulp can be immediately processed into a finished juice product. The containers can be stored in refrigerated, frozen, or room temperature conditions. The juice and pulp are preferably blended in a homogenous blend, after which they may be mixed with other ingredients, such as flavorings, sweeteners, nutritional ingredients, botanicals, and colorings. The finished juice product is preferably heated and pasteurized at a minimum temperature of 181° F. (83° C.) or higher up to 212° F. (100° C.). Another product manufactured is fruit puree and puree juice, in either concentrate or diluted form. Puree is essentially the pulp separated from the seeds and is different than the fruit juice product described herein.

The product is filled and sealed into a final container of plastic, glass, or another suitable material that can withstand the processing temperatures. The containers are maintained at the filling temperature or may be cooled rapidly and then placed in a shipping container. The shipping containers are preferably wrapped with a material and in a manner to maintain or control the temperature of the product in the final containers.

The juice and pulp may be further processed by separating the pulp from the juice through filtering equipment. The filtering equipment preferably consists of, but is not limited to, a centrifuge decanter, a screen filter with a size from 1 micron up to 2000 microns, more preferably less than 500 microns, a filter press, a reverse osmosis filtration device, and any other standard commercial filtration devices. The operating filter pressure preferably ranges from 0.1 psig up to about 1000 psig. The flow rate preferably ranges from 0.1 g.p.m. up to 1000 g.p.m., and more preferably between 5 and 50 g.p.m. The wet pulp is washed and filtered at least once and up to 10 times to remove any juice from the pulp. The resulting pulp extract typically has a fiber content of 10 to 40 percent by weight. The resulting pulp extract is preferably pasteurized at a temperature of 181° F. (83° C.) minimum and then packed in drums for further processing or made into a high fiber product.

The filtered juice and the water from washing the wet pulp are preferably mixed together. The filtered juice may be vacuum evaporated to a brix of 40 to 70 and a moisture of 0.1 to 80 percent, more preferably from 25 to 75 percent. The resulting concentrated juice may or may not be pasteurized. For example, the juice would not be pasteurized in circumstances where the sugar content or water activity was sufficiently low enough to prevent microbial growth.

Processing Seeds from the Selected Plant

Some compositions of the present invention include seeds from the plant. In some embodiments of the present invention, seeds are processed by pulverizing them into a seed powder in a laboratory mill. In some embodiments, the seed powder is left untreated. In some embodiments, the seed powder is further defatted by soaking and stirring the powder in hexane—preferably for 1 hour at room temperature (Drug: Hexane—Ratio 1:10). The residue, in some embodiments, is then filtered under vacuum, defatted again (preferably for 30 minutes under the same conditions), and filtered under vacuum again. The powder may be kept overnight in a fume hood in order to remove the residual hexane.

Still further, in some embodiments of the present invention, the defatted and/or untreated powder is extracted, preferably with ethanol 50% (m/m) for 24 hours at room temperature at a drug solvent ratio of 1:2.

Processing Oil from the Selected Plant

Some embodiments of the present invention may comprise oil extracted from the plant. The method for extracting and processing the oil is described in U.S. patent application Ser. No. 09/384,785, filed on Aug. 27, 1999 and issued as U.S. Pat. No. 6,214,351 on Apr. 10, 2001, which is incorporated by reference herein. The oil typically includes a mixture of several different fatty acids as triglycerides, such as palmitic, stearic, oleic, and linoleic fatty acids, and other fatty acids present in lesser quantities. In addition, the oil preferably includes an antioxidant to inhibit spoilage of the oil. Conventional food grade antioxidants are preferably used.

Iridoids

Figure 2:
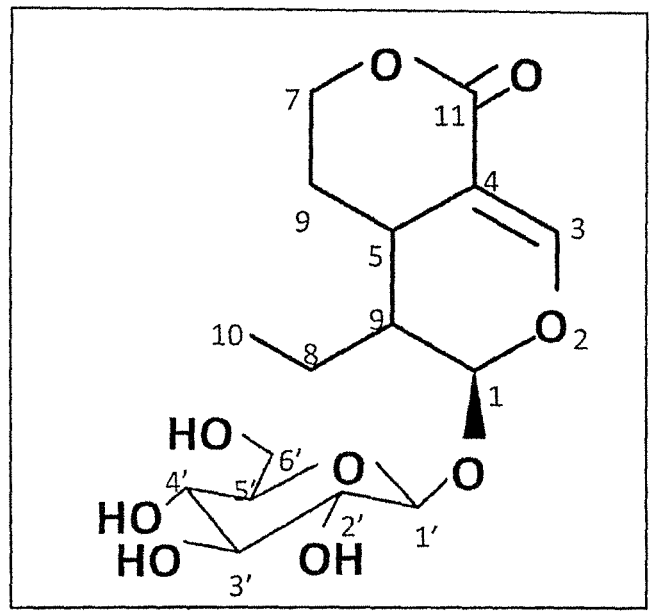
FIG. 2 depicts the structural formula for common iridoids according to some embodiments of the invention.
Figure 2:
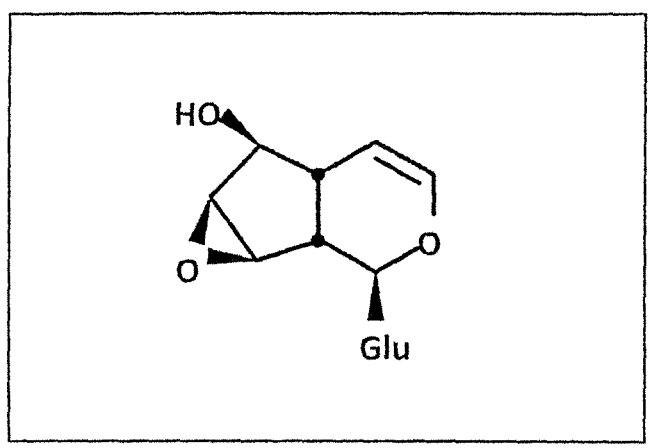
Figure 3:
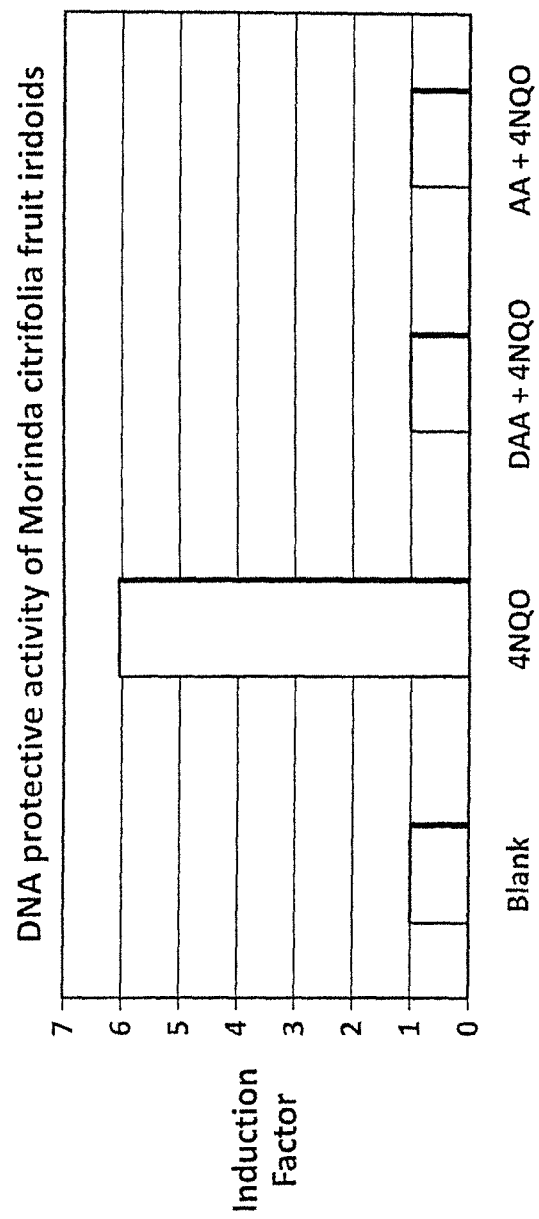
FIG. 3 depicts results from studies demonstrating the DNA protective activity of iridoid containing plant products according to some embodiments of the invention.

Embodiments of the present invention comprise plant source and/or a source of iridoids compositions, each of which include one or more processed plant or naturally occurring. Iridoids are a class of secondary metabolites found in a wide variety of plants and in some animals. Iridoids represent a large and still expanding group of cyclopenta[c]pyran monoterpenoids found in a number of folk medicinal plants used as bitter tonics, sedatives, hypotensives, antipyretics, cough medicines, remedies for wounds and skin disorder. Typical structural formulas for common iridoids are depicted in FIGS. 1 and 2. There are at least three different types of Iridoids: Glycosidic iIridoids with a sugar molecule attach to the monoterpene cyclic ring; Non-Glycosidic Iridoids without a sugar molecule attach to the monoterpene cyclic ring; and Secoiridoid iridoids known for its bitterness and function as deterrence for herbivores but it is simply a class of Iridoids derived from deoxyloganic acid via oxidation to carboxyl at $C_{11}$.

The plant and/or iridoid source may be selected from a variety of plant families and species including (referred to as "List A" below in the formulations section of this application): Scrophylariaceae, Rubiaceae, Gentianaceae, Apocynaceae, Adoxaceae, Lamiaceae, Bignoniaceae, Oleaceae, Verbenaceae, Hydrangeaceae, Orobancaceae, Eucommiaceae, Scrophulariaceae, Acanthaceae, *Galium verum, Morinda officinalis, Galium melanantherum, Pyrola calliatha, Radix Morindae, Pyrola xinjiangensis, Pyrola elliptica, Coussarea platyphylla, Craibiodendron henryi, Crotalaria emarginella,* Cranberry, *Saprosma scortechinii, Galium rivale, Arbutus andrachne, G. humifusum, G. paschale, G. mirum, G. macedonicum, G. rhodopeum, G. aegeum, Galium aparine, Vaccinium myrtillus, Vaccinium bracteatum*, Bilberry, Blueberry, Olive, *Morinda lucida*, Lingonberries, *Morinda parvifolia, Saprosma scortechinii, Arbutus andrachne, Cornus Canadensis, Cornus suecica, Galium species, Liquidambar formasans, Arbutus andrachne, Rhododendron luteum, Arbutus unedo*, Subfamily Rubioideae, *S. sagittatum, S. convolvulifolium, Arctostaphylos uva-ursi, Andromeda polifolia, Tripetaleia paniculata, Asperula adorata, Randia canthioides, Tecomella undulate, Thunbergia alata, Thunbergia fragrans, Mentzelia albescens, Deutzia scabra, Verbascum lychnitis, Mentzelia linleyi, Mentzelia lindleyi, Mentzelia lindbeimerii, Mentzelia involucrate, Randia canthioides, Lamiastrum galeobdolon, Teucrium bircanicum, Teucrium arduini, Betonica officinalis, Barleria prionitis, Harpagophytum procumbens, Ajuga decumbens, Anarrhinum orientale, Linaria clementei, Kickxia spuria, Veronicastrum sibiricum, Physostegia virginiana, Betonica officinalis, Clerodendrum thomsonae, Rebmannia glutinosa, Ajuga reptans, Rebmannia glutinosa, Penstemon nemorosus, Capraria biflora, Rogeria adenophylla, Ajuga spectabilis, Avecennia officinalis, Plantago asiatica, Vitex negundo, Penstemon cardwellii, Tecoma cbrysantha, Odontites verna, Verbascum sinuatum, Verbascum nigrum, Verbascum laxum, Buddleja globosa, Vitex agnuscastus, Penstemon eriantberus, Vitex rotundifolia, Euphrasia rostkoviana, Tecoma beptaphylla, Plantago media, Castilleja wightii, Rebmannia glutinosa, Tecoma beptaphylla, Castilleja rbexifolia, Utricularia australis, Verbascum saccatum, Verbascum sinuatum, Verbascum georgicum, Premna odorata, Premana japonica, Verbascum pulverulentum, Scrophularia scopolii, Scrobularia ningpoensis, Veronica officinalis, Besseya plantaginea, Veronicastrum sibiricum, Catalpa speciosa, Tabebuia rosea, Picrorbiza kurrooa, Veronica bellidioides, Penstemon nemorosus, Globularia alypum, Pinguicula vulgaris, Globularia Arabica, Antirrbinum orontium, Retzia capensis, Pbaulopsis imbricate, Macfadyena cynancboides, Paulownia tomentosa, Asystasia bella, Rebmannia glutinosa, Erantbemum pulcbellum, Hygropbila difformis, Boscbniakia rossica, Linaria cymbalaria, Satureja vulgaris, Lamium amplexicaule, Viburnum betulifolium, Viburnum bupebense, Tecoma stans, Plantago arenaria, Campsidium valdivianum, Campsis chinensis, Tecoma capensis, Penstemon pinifolius, Eupbrasia salisburgensis, Clerodendrum incisum, Clerodendrum incisum, Clerodendrum ugandense, Lamourouxia multifida, Nepeta cataria, Argylia radiate, Linaria cymbalaria, Monocbasma savatieri, Veronica anagallis-aquatica, Avicennia offinalis, Avicennia marina, Gentian, pedicellata, Alangium platanifolium, Lonicera coerulea, Swertica japonica, Melampyrum cristatum, Monochasma savatieri, Vitex negundo, Avicennia marina, Tarenna graveolens, Argylia radiate, Veronica anagallis-aquatica, Castilleja integra, Galium verum, Arbutus unedo, Galium mollugo, Andromeda polifolia, Gelsemium sempervirens, Verbena brasiliensis, Gelsemium sempervirens, Randia dumetorum, Penstemon barbatus, Odontites verna, Gentiana verna, Erytbraea centaurium, Gentiana pyrenaica, Desfontainia spinosa, Lonicera periclymenum, Strycbnos roborans, Pedicularis palustris, Penstemon nitidus, Citbarexylum fruticosum, Fouquieria diguetii, Nyctantbes arbortristis, Mussaenda, Besseya plantaginea, Stacbytarpbeta jamaicensis, Cantbium subcordatum, Barleria lupulina, Barleria prionitis, Plectronia odorata, Salvia digitaloides, Stacbytarpbeta mutabilis, Penstemon strictus, Duranta plumeri, Sesamum angolense, Rebmannia glutinosa, Parentucellia viscose, Melampyrum arvense, Gardenia jasminoides, Randia Formosa, Oldenlandia diffusa, Castilleja integra, Eupbrasia rostkoviana, Fouquieria diguetii, Penstemon nitidus, Feretia apodantbera, Randia cantbioides, Asystasia bella, Viburnum urceolatum, Gentiana depressa, Syringa reticulate, Deutzia scabra, Eccremocarpus scaber, Cistanche salsa, Rebmannia glutinosa, Catalpa ovate, Myoporum deserti, Teucrium marum, Gelsemium sempervirens, Viburnum urceolatum, Argylia radiate, Morinda lucida, Thunbergia gandiflora, Thunbergia alata, Thunbergia laurifolia, Mentzelia cordifolia, Angelonia integerrima, Linaria genstifolia, Caryopteris mongholica, Linaria arcusangeli, Leonurus persicus, Tubebuia impetiginosa, Phyllarthron madagascariense, Phsostegia virginiana, Harpagophytum procumbens, Caryopteris clandonensis, Cymbalaria muralis, Scrophularia buergeriana, Caryopteris mongholica, Caryopteris clandonensis, Verbascum undulatum, Globularia dumulosa, Pedicularis artselaeri, Utricularia vulgaris, Pedicularis chinensis, Verbascum phlomoides, Plantago subulata, Clerodendrum inerme, Scrophularia lepidota, Globularia davisiana, Globularia cordifolia, Holmskioldia* sanguine, Gmelina philippensis, Scrophularia nodosa, Picrorhiza kurroa, Gmelina arborea, Penstemon newberryi, Asystasia intrusa, Catalpa fructus, Scrophularia scorodonia, Premna subscandens, Catalpa ovate, Verbascum spinosum, Scrophularia auriculata, Scrophularia lepidota, Veronica hederifolia, Tabebuia impetiginosa, Veronica pectinata var. glandulosa, Baleria strigosa, Pedicularis procera, Crescentia cujete, Thunbergia grandiflora, Thunbergia laurifolia, Viburnum suspensum, Pedicularis kansuensis, Nepeta Cilicia, Euphrasia pectinata, Penstemon parryi, Penstemon barrettiae, Tecoma capensis, Pedicularis plicata, Vitex altissima, Veronica anagallis-aquatica, Clerodendrum inerme, Vitex agnus-castus, Dipsacus asperoides, Chioccoca alba, Alangium lamarckii, Cornus capitata, Strychnos nux-vomica, Alangium platanifolia var. trilobum, Gentiana linearis, Swertia franchetiana, Picconia excels, Clerodendrum inerme, Verbenoxylum reitzii, Leonurus persicus, Avicennia germinans, Canthium berberidifolium, Clerodendrum inerme, Avicennia officinalis, Lippia graveolens, Ajuga pseudoiva, Barleria lupulina, Calycophyllum spruceanum, Phlomis capitata, Phlomis nissolii, Premna barbata, Plantago alpine, Avicennia marina, Galium humifusum, Morinda coreia, Saprosma scortechinii, Plantago atrata, P. maritime, P. subulata, Erinus alpines, Paederia scandens, Tocoyena Formosa, Fagraea blumei, Hedyotis chrysotricha, Paederia scandens, Jasmium hemsleyi, Eucnide bartonioides, Rauwolfia serpentine, Picconi, excels, Gentiana kurroo, Nepeta cadmea, Gmelina philippensis, Penstemon mucronatus, Citharexylum caudatum, Phlomis aurea, Eremostachys glabra, Phlomis rigida, P. tuberose, Pedicularis plicata, Duranta erecta, Bouchea fluminensis, Phlomis brunneogaleata, Barleria lupulina, Zaluzianskya capensis, Thevetia peruviana, Plantago lagopus, Gardenoside (and its acid hydrolysis product), Asperuloside (and its acid hydrolysis product), Canthium schimperianum, Plantago arborescens, P. ovate, P. webbii, Plantago cornuti, Plantago hookeriana, Plantago altissima, Penstemon secudiflorus, Viburnum luzonicum, Galium lovcense, Nyetanthes arbor-tristis, Rothmania macrophylla, Myxopyrun smilacifolium, Nepeta racemosa, Linaria japonica, Viburnum ayavacense, Viburnum tinus, Viburnum rhytidophyllum, Viburnum lantana var. discolor, Viburnum prunifolium, Centranthus longiflorus, Viburnum sargenti, Plumeria obtuse, Dunnia sinensis, Morinda morindoides, Caryopteris clandonensis, Vitex rotundifolia, Globularia dumulosa, Pedicularis artselaeri, Cymbaria mongolica, Pedicularis kansuensis f. albiflora, Phlomis umbrosa, Dunnia sinensis, Gelsemium sempervirens, Verbena littoralis, Syringia afghanica, Tabebuia impetiginosa, Patrinia scabra, Catalpa fructus, Scrophularia lepidota, Lasianthus wallichii, Crescentia cujete, Kickxia elatine, K. spuria, K. commutate, Linaria arcusangeli, L. flava, Coelospermum billardieri, Randia spinosa, Asperula maximowiczii, Wulfenia carinthiaca, Fagraea blumei, Daphniphyllum calycinum, Penstemon ricbardsonii, Nardostachys chinensis, Sambucus ebulus, Penstemon confertus, Sambucus ebulus, Penstemon serrulatus, Penstemon birsutus, Viburnum furcatum, Viburnum betulifolium, Viburnum japonicum, Allamanda neriifolia, Plumeria acutifolia, Allamanda catbartica, Alstonia boonei, Actinidia polygama, Patrinia villosa, Patrinia gibbosa, Posoqueria latifolia, Strycbnos spinosa, Kigelia pinnata, Centrantbus ruber, Cerbera mangbas, Mentzelia spp., Teucrium marum, Eucommia ulmoides, Aucuba japonica, Gelsemium sempervirens, Syring a amurensis, Strychnos spinosa, Lonicera alpigena, Nauclea diderrichii, Olea europaea, Ligustrum japonicum, Swertia japonica, Swertia mileensis, Cruckshanksia verticillata, Gentiana asclepiadea, Jasminum multiflorum, Menyantbes trifoliate, Jasminum mesnyi, Jasminum azoricum, Jasminum sambac, Centaurium erythraea, Centaurium littorale, Gentiana gelida, Gentiana scabra, Jasmium bumile var. revolutum, Syringa vulgaris, Osmantbus ilicifolius, Ligustrum ovalifolium, Ligustrum obtusifolium, Gentiana pyrenaica, Isertia baenkeana, Olea europaea, Osmantbus fragrans, Exacum tetragonum, Hydrangea macrophylla, Hydrangea scandens, Abelia grandiflora, Dipsacus laciniatus, Scaevola racemigera, Erytbraea centaurium, Lisiantbus jefensis, Alyxia reinwardtii, Desfontainia spinosa, Patrinia saniculaefolia, Plantago asiatica, Plantago species, Gentiana species, Hapagophytum species, Pterocephalus perennis subsp. Perennis, Morinda citrifolia, Campsis grandiflora, Heracleum rapula, Syringa dilatata, Bartsia alpine, Hedyotis diffusa, Sickingia williamsii, Buddleja cordobensis, Borreria Verticillata and combinations thereof.

Some embodiments may utilize an iridoid source from any of the parts of the listed plants plant alone, in combination with each other or in combination with other ingredients. For example the leaves including leaf extracts, fruit, bark, seeds including seed oil, roots, oils, juice including the fruit juice and fruit pulp and concentrates thereof, or other product from the list of plants may be utilized as an iridoid source. Thus, while some of the parts of the plants are not mentioned above, some embodiments may use of one or more parts selected from all of the parts of the plant.

Some compositions of the present invention comprise a source of iridoids present between about 1 and 5 percent of the weight of the total composition. Other such percentage ranges include: about 0.01 and 0.1 percent; about 0.1 and 50 percent; about 85 and 99 percent; about 5 and 10 percent; about 10 and 15 percent; about 15 and 20 percent; about 20 and 50 percent; and about 50 and 100 percent.

In some embodiments the source of iridoids may be combined with other ingredients or carriers (discussed further herein) to produce a pharmaceutical grade source of iridoids ("pharmaceutical" herein referring to any drug or product designed to improve the health of living organisms such as human beings or mammals, including nutraceutical products).

In some embodiments various extracts may be utilized from one or more of the plants listed above. In some embodiments the extracts may comprise 7b-Acetoxy-10-O-acetyl-8a-hydroxydecapetaloside (Compound-2), 10-Acetoxymajoroside, 7-O-Acetyl-10-O-acetoxyloganin, 6-O-Acetylajugol, 6-O-(2_-O-Acetyl-3_O-cinnamoyl-4_-O-p-methoxy cinnamoyl-a-L-rhamnopyranosyl) catalpol, 6-O-(3_-O-Acetyl-2_-O-trans-cinnamoyl)-a-L-rhamnopyranosyl catalpol, 8-O-Acetylclandonoside, 8-O-Acetyl-6_-O-(p-coumaroyl)harpagide, 8-O-Acetyl-6-O-trans-p-coumaroyls-hanzhiside, 6-Acetyl deacetylasperuloside, 8-O-Acetyl-1-epi-shanzhigenin methyl ester, Acetylgaertneroside, 10-O-Acetylgeniposidic acid, 10-O-Acetyl-8a-hydroxydecapetaloside, 8-O-Acetyl-6b-hydroxyipolamide, 2-O-Acetyllamiridoside, 3-O-Acetylloganic acid, 4-O-Acetylloganic acid, 6-O-Acetylloganic acid, 6b-Acetyl-7b-(E)-p-methoxycinnamoyl-myxopyroside, 6b-Acetyl-7b-(Z)-p-methoxycinnamoyl-myxopyroside, 10-O-Acetylmonotropein, 8-O-Acetylmussaenoside, 10-O-Acetylpatrinoside, 3-O-Acetylpatrinoside, 6-O-Acetylplumieride-p-E-coumarate, 6-O-Acetylplumieride-p-Z-coumarate, 6-O-Acetylscandoside, 8-O-Acetylshanzhigenin methyl ester, 8-O-Acetylshanzhiside, Acuminatuside, Agnucastoside A (6-O-Foliamenthoylmussaenosidic acid), Agnucastoside B (6-O-(6,7-Dihydrofoliamenthoyl)-mussaenosidic acid), Agnucastoside C (7-O-trans-p-Coumaroyl-6-O-trans-caffeoyl-8-epi-loganic acid), Alatoside, Alboside I, Alboside II, Alboside III, Alpinoside, Angeloside, 6-O-b-D-Apiofuranosylmussaenosidic acid, 2-O-Apiosylgardoside, Aquaticoside A (6-O-Benzoyl-8-epi-loganic acid), Aquaticoside B (6-O-p-Hydroxybenzoyl-8-epi-loganic acid), Aquaticoside C (6-O-Benzoylgardoside), Arborescoside, Arborescosidic acid, Arborside D, Arcusangeloside, Artselaenin A, Artselaenin C, Artselaenin B, Asperuloide A, Asperuloide B, Asperuloide C, Asperulosidic acid ethyl ester, 6-O-a-L-(2-O-Benzoyl,3-O-trans-p-coumaroyl) rhamnopyranosylcatalpol, 10-O-Benzoyldeacetylasperulosidic acid, 6-O-Benzoyl-8-epi-loganic acid, 6-O-Benzoylgardoside, 10-O-Benzoylglobularigenin, 10-Bisfoliamenthoylcatalpol, Blumeoside A Blumeoside B, Blumeoside C, Blumeoside D, Boucheoside, Brunneogaleatoside, 3b-Butoxy-3,4-dihydroaucubin, 6-O-Butylaucubin, 6-O-Butyl-epi-aucubin, 6-O-Caffeoylajugol, 10-O-Caffeoylaucubin, 6-O-trans-Caffeoylcaryoptosidic acid, 10-O-trans-p-Caffeoylcatalpol, 10-O-E-Caffeoylgeniposidic acid, 2-Caffeoyl-mussaenosidic acid, 6-O-trans-Caffeoylnegundoside, Caryoptosidic acid, Caudatoside A, Caudatoside B, Caudatoside C, Caudatoside D, Caudatoside E, Caudatoside F, Chlorotuberoside, 10-O-(Cinnamoyl)-6-(desacetyl-alpinosidyl)catalpol, 10-O-E-Cinnamoylgeniposidic acid, 8-O-Cinnamoyl-mussaenosidic acid, 8-Cinnamoylmyoporoside, 7b-Cinnamoyloxyugandoside (Serratoside A), 7-O-trans-p-Coumaroyl-6-O-trans-caffeoyl-8-epi-loganic acid, 6-O-a-L-(2-O-trans-Cinnamoyl)-rhamnopyranosylcatalpol, 6-O-a-L-(3-O-trans-Cinnamoyl)-rhamnopyranosylcatalpol, 6-O-a-L-(4-O-trans-Cinnamoyl)-rhamnopyranosylcatalpol,
Citrifolinin A, Citrifolinoside A, Clandonensine, Clandonoside, Clandonoside II, Coelobillardin, 6-O-trans-p-Coumaroyl-8-O-acetylshanzhiside methyl ester, 6-O-cis-p-Coumaroyl-8-O-acetylshanzhiside methyl ester, 6-O-(p-Coumaroyl)antirrinoside, 10-O-cis-p-Coumaroylasystasioside E, 10-O-trans-p-Coumaroylasystasioside E, 6-O-p-Coumaroylaucubin, 6-O-p-trans-Coumaroylcaryoptosidic acid, 6-O-cis-p-Coumaroylcatalpol, 10-O-cis-p-Coumaroylcatalpol, 6-O-trans-p-Coumaroyl-7-deoxyrehmaglutin A, 6-O-cis-p-Coumaroyl-7-deoxyrehmaglutin A, 2-trans-p-Coumaroyldihydropenstemide, 2-O-Coumaroyl-8-epi-tecomoside, 10-O-trans-Coumaroyleranthemoside, 10-O-E-p-Coumaroylgeniposidic acid, 7-O-Coumaroylloganic acid, Crescentin I, Crescentin II, Crescentin III, Crescentin IV, Crescentin V, 6-O-trans-p-Coumaroylloganin, 6-O-cis-p-Coumaroylloganin, 7-O-p-Coumaroylpatrinoside, 2-O-Coumaroylplantarenaloside, 6-O-(4-O-p-Coumaroyl-b-D-xylopyranosyl)-aucubin, 7b-Coumaroyloxyugandoside, Crescentoside A, Crescentoside B, Crescentoside C, Cyanogenic glycoside of geniposidic acid, Daphcalycinosidine A, Daphcalycinosidine B, Davisioside, Deacetylalpinoside (Arborescosidic acid), Dehydrogaertneroside, Dehydromethoxygaertneroside, 5-Deoxyantirrhinoside, 4-Deoxykanokoside A, 4-Deoxykanokoside C, 6-Deoxymelittoside, 5-Deoxysesamoside, Desacetylhookerioside, Des-p-hydroxybenzoylkisasagenol B, 2,3-Diacetylisovalerosidate, 2,3-Diacetylvalerosidate, 6-O-a-L-(2-O-,3-O-Dibenzoyl, 4-O-cis-p-coumaroyl) rhamnopyranosylcatalpol, 6-O-a-L-(2-O-,3-O-Dibenzoyl-4-O-trans-p-coumaroyl) rhamnopyranosylcatalpol, 6-O-a-L-(2-O-3-O-Dibenzoyl) rhamnopyranosylcatalpol, 6a-Dihydrocornic acid, 6b-Dihydrocornic acid, 6-O-(6,7-Dihydrofoliamenthoyl)-mussaenosidic acid, 3,4-Dihydro-3a-methoxypaederoside, 3,4-Dihydro-3b-methoxypaederoside, 3,4-Dihydro-6-O-methylcatalpol, 5,6b-Dihydroxyadoxoside, 2-(2,3-Dihydroxybenzoyloxy)-7-ketologanin, 5b,6b-Dihydroxyboschnaloside, Dimer of paederosidic acid, Dimer of paederosidic acid and paederoside, Dimer of paederosidic acid and paederosidic acid methyl ester, 6-O-(3,4-Dimethoxybenzoyl)crescentin IV 3-O-b-D-glucopyranoside, 10-O-(3,4-Dimethoxy-(E)-cinnamoyl)-aucubin, 10-O-(3,4-Dimethoxy-(Z)-cinnamoyl)-catalpol, 10-O-(3,4-Dimethoxy-(E)-cinnamoyl)-catalpol, 6-O-[3-O-(trans-3,4-Dimethoxycinnamoyl)-a-L-rhamnopyranosyl]-aucubin, Dumuloside, Dunnisinin, Dunnisinoside, Duranterectoside A, Duranterectoside B, Duranterectoside C, Duranterectoside D, 6-epi-8-O-Acetylharpagide, 6-O-epi-Acetylscandoside, 6,9-epi-8-O-Acetylshanzhiside methyl ester, 8-epi-Apodantheroside, 1,5,9-epi-Deoxyloganic acid glucosyl ester, 5,9-epi-7,8-Didehydropenstemoside, (5a-H)-6a-8-epi-Dihydrocornin, 8-epi-Grandifloric acid, 7-epi-Loganin, 8-epi-Muralioside, 5,9-epi-Penstemoside, 3-epi-Phlomurin, 1-epi-Shanzhigenin methyl ester, 8-epi-Tecomoside (7b-Hydroxyplantarenaloside), 7b,8b-Epoxy-8a-dihydrogeniposide, 7,8-Epoxy-8-epi-loganic acid, 6b,7b-Epoxy-8-epi-splendoside, Epoxygaertneroside, Epoxymethoxygaertneroside, Erinoside, 8-O-Feruloylharpagide, 7-O-E-Feruloylloganic acid, 7-O—Z-Feruloylloganic acid, 6-O-E-Feruloylmonotropein, 10-O-E-Feruloylmonotropein, 6-O-trans-Feruloylnegundoside, 6-O-a-L-(4-O-cis-Feruloyl)-rhamnopyranosylcatalpol, 6-O-Foliamenthoylmussaenosidic acid, 2-O-Foliamenthoylplantarenaloside, Formosinoside, 10-O-b-D-Fructofuranosyltheviridoside, Gaertneric acid, Gaertneroside, 6-O-a-D-Galctopyranosylharpagoside, 6-O-a-D-Galactopyranosylsyringopicroside, Gelsemiol-6-trans-caffeoyl-1-glucoside, Globuloside A, Globuloside B, Globuloside C, 3-O-b-D-Glucopyranosylcatalpol, 6-O-(4-O-b-Glucopyranosyl)-trans-p-coumaroyl-8-O-acetylshanzhiside methyl ester, 6-O-a-D-Glucopyranosylloganic acid, 3-O-b-Glucopyranosylstilbericoside, 6-O-a-D-Glucopyranosylsyringopicroside, 3-O-b-D-Glucopyranosylsyringopicro side, 4-O-b-D-Glucopyranosylsyringopicroside, 3-O-b-D-Glucopyranosyltheviridoside, 6-O-b-D-Glucopyranosylthevirido side, 10-O-b-D-Glucopyranosyltheviridoside, 4-O-Glucoside of linearoside (7-O-(4-O-Glucosyl)-coumaroylloganic acid), Glucosylmentzefoliol, Gmelinoside A, Gmelinoside B, Gmelinoside C, Gmelinoside D, Gmelinoside E, Gmelinoside F, Gmelinoside G, Gmelinoside H, Gmelinoside I, Gmelinoside J, Gmelinoside K, Gmelinoside L, Gmephiloside (1-O-(8-epi-Loganoyl)-b-D-glucopyranose), Grandifloric acid, GSIR-1, Hookerioside, 6a-Hydroxyadoxoside, 6-O-p-Hydroxybenzoylasystasioside, 2-O-p-Hydroxybenzoyl-6-O-trans-caffeoyl-8-epi-loganic acid, 2-O-p-Hydroxybenzoyl-6-O-trans-caffeoylgardoside, 6-O-p-Hydroxybenzoylcatalposide, 3-O-(4-Hydroxybenzoyl)-10-deoxyeucommiol-6-O-b-D-glucopyranoside, 2-O-p-Hydroxybenzoyl-8-epi-loganic acid, 6-O-p-Hydroxybenzoyl-8-epi-loganic acid, 2-O-p-Hydroxybenzoylgardoside, 6-O-p-Hydroxybenzoylglntinoside, 7-O-p-Hydroxybenzoylovatol-1-O-(6_-O-p-hydroxybenzoyl)-b-D-glucopyranoside, 8-O(-2-Hydroxycinnamoyl)harpagide, 5-Hydroxydavisioside, 10-Hydroxy-(5a-H)-6-epi-dihydrocornin, 1b-Hydroxy-4-epi-gardendiol, 6b-Hydroxy-7-epi-loganin, (5a-H)-6a-Hydroxy-8-epi-loganin, 7b-Hydroxy-11-methylforsythide, 6b-Hydroxygardoside methyl ester, 6a-Hydroxygeniposide, 4-Hydroxy-E-globularinin, 7b-Hydroxyharpagide, 5-Hydroxyloganin, 7b-Hydroxyplantarenaloside, Humifusin A, Humifusin B, Inerminoside A, Inerminoside A1, Inerminoside B, Inerminoside C, Inerminoside D, Ipolamidic acid, Iridoid dimer of asperuloside and asperulosidic acid, Iridolactone, Iridolinarin A, Iridolinarin B, Iridolinarin C, Iridolinaroside A, 6-O-Isoferuloyl ajugol, 10-O-trans-Isoferuloylcatalpol, Isosuspensolide E, Isosuspensolide F, Isounedoside, Isovibursinoside II, Isoviburtinoside III, Jashemsloside A, Jashemsloside B, Jashemsloside C, Jashemsloside D, Jashemsloside E (6S-7-O-{6-O-[b-D-apiofuranosyl-(1→6)-b-Dglucopyranosyl]menthiafolioyl}-loganin, Kansuenin, Kansuenoside, 7-Ketologanic acid, Kickxin, Lamidic acid, Lantanoside, Linearoside (7-O-Coumaroylloganic acid), Lippioside I (6-O-p-trans-Coumaroylcaryoptosidic acid), Lippioside II (6-O-trans-Caffeoylcaryoptosidic acid), Loganic acid-6-O-b-D-glucoside, Lupulinoside, Luzonoid A, Luzonoid B, Luzonoid C, Luzonoid D, Luzonoid E, Luzonoid F, Luzonoid G, Luzonoside A, Luzonoside B, Luzonoside C, Luzonoside D, Macedonine, Macrophylloside, 7-O-(6-O-Malonyl)-cachinesidic acid (Malonic ester of 8-hydroxy-8-epiloganic acid), Melittoside 3-O-b-glucopyranoside, 5-O-Menthiafoloylkickxioside, 6-O-Menthiafoloylmussaenosidic acid, Mentzefoliol, 6-O-(4-Methoxybenzoyl)-5,7-bisdeoxycynanchoside, 6-m-Methoxybenzoylcatalpol, 6-O-(4-Methoxybenzoyl) crescentin IV (3-O-b-D-glucopyranoside), 10-O-(4-Methoxybenzoyl)impetiginoside A, 7-O-(p-Methoxybenzoyl)-tecomoside, 6-O-p-Methoxy-trans-cinnamoyl-8-O-acetylshanzhiside methyl ester, 6-O-p-Methoxy-cis-cinnamoyl-8-O-acetylshanzhiside methyl ester, 10-O-trans-p-Methoxycinnamoylasystasioside E, 10-O-cis-p-Methoxycinnamoyl asystasioside E, 10-O-cis-p-Methoxycinnamoylcatalpol, 10-O-trans-p-Methoxycinnamoylcatalpol, 8-O-Z-p-Methoxycinnamoylharpagide, 6-O-Z-p-Methoxycinnamoylharpagide, 8-O-E-p-Methoxycinnamoylharpagide, 6-O-E-p-Methoxycinnamoylharpagide, 1b-Methoxy-4-epi-gardendiol, 1b-Methoxy-4-epi-mussaenin A, 1a-Methoxy-4-epi-mussaenin A, Methoxygaertneroside, 1b-Methoxygardendiol, 4-Methoxy-Z-globularimin, 4-Methoxy-Z-globularinin, 4-Methoxy-E-globularimin, 4-Methoxy-E-globularinin, 6-O-[3-O-(trans-p-Methoxycinnamoyl)-a-L-rhamnopyranosyl]-aucubin, 1b-Methoxylmussaenin A, 6-O-Methyl-epi-aucubin, Muralioside (7b-Hydroxyharpagide), Myxopyroside, Nepetacilicioside, Nepetanudoside, Nepetanudoside B, Nepetanudoside C, Nepetanudoside D, Nepetaracemoside A, Nepetaracemoside B, Ningpogenin (revision of 1-dehydroxy-3,4-dihydroaucubingenin), Officinosidic acid (5-Hydroxy-10-O-(p-methoxycinnamoyl)-adoxosidic acid), Ovatic acid methyl ester-7-O-(6-O-p-Hydroxybenzoyl)-b-D-glucopyranoside, Ovatolactone-7-O-(6-O-p-hydroxybenzoyl)-b-D-glucopyranoside, 7-Oxocarpensioside, Paederoscandoside, Paederosidic acid methyl ester, Patrinioside, Pedicularis-lactone, Phlomiside, Phlomoidoside (6-O-(4-O-p-Coumaroyl-b-D-xylopyranosyl)-aucubin), Phlomurin, Phlorigidoside A (2-O-Acetyllamiridoside), Phlorigidoside B (8-O-Acetyl-6b-hydroxyipolamide), Phlorigidoside C (5-Deoxysesamoside), Picconioside 1, Picroside IV, Picroside V (6-m-Methoxybenzoylcatalpol), Pikuroside, Plicatoside A, Plicatoside B, Premnaodoroside D, Premnaodoroside E, Premnaodoroside F [isomeric mixture of A and B in ratio (1:1)], Premnaodoroside G (isomeric mixture of (C) and (D)), Premnosidic acid, Proceroside (7-Oxocarpensioside), Randinoside, Saletpangponoside A [6-O-(4-O-b-Glucopyranosyl)-trans-p-coumaroyl-8-O-acetylshanzhiside methyl ester], Saletpangponoside B, Saletpangponoside C, Sammangaoside C (Melittoside 3-O-b-glucopyranoside), Saprosmoside A, Saprosmoside B, Saprosmoside C, Saprosmoside D, Saprosmoside E, Saprosmoside F, Saprosmoside G, Saprosmoside H, Scorodioside (6-O-(3-O-Acetyl-2_-O-trans-cinnamoyl)-a-L-rhamnopyranosyl catalpol), Scrolepidoside, Scrophuloside A1, Scrophuloside A2, Scrophuloside A3, Scrophuloside A4, Scrophuloside A5, Scrophuloside A6, Scrophuloside A7, Scrophuloside A8, Scrophuloside B4 [6-O-(2_-O-Acetyl-3_-O-cinnamoyl-4_-O-p-methoxy cinnamoyl-a-L rhamnopyranosyl)catalpol], Scrovalentinoside, Senburiside III, Senburiside IV, Serratoside A, Serratoside B, Shanzhigenin methyl ester, 6-O—Sinapoyl scandoside methyl ester, Sintenoside, Stegioside I, Stegioside II, Stegioside III, Syringafghanoside, 7,10,2,6-Tetra-O-acetylisosuspensolide F, 7,10,2,3-Tetra-O-acetylisosuspensolide F, 7,10,2_,3_-Tetra-O-acetylsuspensolide F, Thunaloside, 7,10,2-Tri-O-acetylpatrinoside, 7,10,2_-Tri-O-acetylsuspensolide F, 6-O-a-L-(2-O-,3-O-,4-O-Tribenzoyl)-rhamnopyranosylcatalpol, 6-O-(3_,4_,5_-Trimethoxybenzoyl)ajugol, Unbuloside (6-O-[(2-O-trans-Feruloyl)-a-L-rhamnopyranosyl]-aucubin), Urphoside A, Urphoside B, Verbaspinoside (6-O-[(2_-O-trans-Cinnamoyl)-a-L-rhamnopyranosyl]-catalpol), Viburtinoside I, Viburtinoside II, Viburtinoside III, Viburtinoside IV, Viburtinoside V, Viteoid I, Viteoid II, Wulfenoside [(10-O-(Cinnamoylalpinosidyl)-6-(desacetyl-alpinosidyl)-catalpol)], Yopaaoside A, Yopaaoside B, Yopaaoside C, Zaluzioside (6b-Hydroxygardoside methyl ester), Abelioside A, Abelioside A dimethyl acetal, Abelioside B, 10-Acetoxyoleuropein, 2'-O-Acetyldihydropensternide, 2'-O-Acetylpatrinoside, 13-0-Acetylplurnieride, 7-0-Acetylsecologanol, 2'-O-Acetylswert~amain1, 10-0-Acetylviburnalloside, Actinidialactone, Allarnancin I, Allarncidin A, Allarncidin B, Allamcidin B P-c-glucose, Allarncin, Allaneroside, Allodolicholactone, 3-O-Allosylcerberidol, 3-O-Allosylcyclocerberidol, 3-O-Allosylepoxycerbeeridol, Alpigenoside, Arnarogentin, Amaroswerin, 6'-O-Apiosylebuloside m, Azoricin, 3, IO-Bis-O-allosylcerberidol, Boonein, 13-O-Caffeoylplurnieride, Centauroside, Cerberic acid, Cerberidol, Cerberinic acid, Cerbinal, Confertoside, 4'-O-cis-p-Cournaroyl-7a-rnorronisi, 4'-O-truns-p-Coumaroyl-7a-rnorronisi, 4'-O-cis-p-Cournaroyl-7P-rnorronisi, 4'-O-truns-p-Cournaroyl-7-morronisi, 13-O-Coumaroylplurnieride, Cyclocerberidol, Decentapicrin A, kentapicrin B, Decentapicrin C, Deglucoserrulatoside, Deglucosyl plumieride, Dehydroiridodialo-P-D-gentiobioside, Dehydroiridomyrrnecin, 5,6-Dehydrojasrninin, Demethyloleuropein, 1-Deoxyeucomrniol, 9'-hxyjasrninigenin, 10-Deoxyptrinoside, 10-Deoxyptrinoside aglycone, 10-Deoxypensternide, 13-Deoxyplumieride, Desacetylcentapicrin, Desfontainic acid, Desfontainoside, 2',3'-O-Diacetylfurcatoside C, 8,9-Didehydro-7-hydroxydolichodial, Diderroside, 7,7-O-Dihydroebuloside, Dihydrcepinepetalactone, Dihydrofoliamenthin, 8,9-Dihydrojasrninin, Dihydropensternide, P-Dihydroplurnericinic acid glucosyl ester, Dihydroserruloside, Dolichodial, Dolicholactone, Ebuloside, 8-epi-Dihydropensternide, 7-epi-Hydrangenoside A, 7-epi-Hydrangenoside C, 7-epi-Hydrangenoside E, 8-epi-Kingiside, 8-epi-Valerosidate, 7-rpt-Vogeloside, Epoxycerberidol, I 1-Ethoxyviburtinal, Eucommioside 1, Eucornmioside II, Fliederoside I, 2'-O-Foliarnenthoyldihydropensternide, Furcatoside A, Furcatoside B, Furcatoside C, Gelidoside I, Gelserniol, Gelserniol-I-glucoside, Gelsemiol-3-glucoside, Gentiogenal, Gentiopicral, Gentiopicroside, 7-O-Gentiroylsecologanol, Gibboside, G'-O-~-~-Glucosylgentiopicrosid, (7iR)-Haenkeanoside I, (7S)-Haenkeanoside I, Hiiragilide, Hydrangenoside A, Hydrangenoside B, Hydrangenoside C, Hydrangenoside D, Hydrangrnoside E, Hydrangenoside F, Hydrangenoside G, 9"-Hydroxy~asrnesoside, 9"-Hydroxyjasrnesos1dic acid, (7R)-IO-Hydroxyrnorroniside, (7s)-IO-Hydroxymorroniside, 10-Hydroxyoleoside dimethyl ester, 10-Hydroxyoleuropein, Ibotalactone A, Ibotalactone B, Iridodialo-P-D-gentiobioside, Lsoactinidialactone, Lsoallarnandicin, lsodehydroiridornyrmecin, Isodihydroepinepetalacton, Isodolichodial, Isoepiiridomyrmecin, (7R)-lsohaenkeanoside, (7S)-lsohaenkeanoside, Lsoligustroside, isoneonepetalactone, Isonuezhenide, Lsooleuropein, 8-lsoplumieride, Isosweroside, Jasrnesoside, Jasminin-lO"-O-glucoside, Jasminoside, Jasmisnyiroside, Jasmolactone A, Jasmolactone B, Jasmolactone B dimethylare, Jasmolactone C, Jasmolactone D, Jasmolactone D tetramethylare, Jasmoside, Jiofuran, Jioglutolide, Kingiside aglycone, Laciniatoside V, Latifonin, Ligustaloside A, Ligusraloside B, Ligusraloside B dimethyl acetal, Ligustrosidic acid, Ligustrosidic acid methyl ester, Lilacoside, Lisianthoside, Menthiafolin, Mentzerriol, 7a-Methoxyswerosode, 3-0-Methylallamancin, 3-0-Mrthylallamcin, Methyl glucooleoside, Methylgrandifloroside, (7R)—O-Methylhaenkeano side, (7S)—O-Methylhaenkeano side, (7R)—O-Methylisohaenkeanoside 1, (7S)—O-Mrthylisohaenkranoside, (7R)—O-Methylmorronisidr, (7S)—O-Methylmorroniside, Methyl syramuraldehydate, 6'-O-[(2R)-Methyl-3-veratroyloxypropanoyl, 6'-0-[(2R)-Methyl-3-veratroyloxypropanoyl, 7a-Morroniside, 7P-Morroniside, Nardosrachin, Neonuezhenide, Neooleuropein, 4aa,7a,7aa-Nepetalactone, 4aa,7α,7a P-Nepetalactone, 4ap, 70,7a P-Nepetalactone, Nepetariasidc, Nepetaside, Norviburtinal, Oleoactcosidr, 7a-morroniside, 7P-morronisidr, Olebechinacoside, Olmnuezhenide, Oleo side dimethyl ester, Oleuropeinic acid, Oleuropeinic acid methyl ester, Oleuroside, Oruwacin, Oxysporone, Patrinalloside, Penstebioside, Penstemide aglycone, Plumenoside, Plumiepoxide, la-Plumieride, Plumieride coumarare, Plumieride coumarate glucoside, Plumieridine, Posoquenin, la-Protoplumericin A, Protoplumericin A, Protoplumericin B, Pulorarioside, Rehmaglutin, Sambacin, Sambacolignoside, Sambacoside A, Sambacoside E, Sambacoside F, Scabraside, Scaevoloside, Secologanin dimethyl acetal, Secologanol, Secologanoside, Secologanoside dimethyl ester, Secoxyloganin, Serrulatoloside, Serrulatoloside aglycon, Serrulatoside, Serruloside, Stryspinolactone, Suspensolide A, Suspensolide A aglycone, Suspensolide B, Suspensolide C, Swertiamarin, Syringalactonr A, Syringalactonr B, 6'-0-Vanilloyl-8-ept-kingiside, Viburnalloside, Villosol, Villosoloside, Adoxoside, Agnuside, Allarnnndin, Allamdin, Amaropentin, Antirride, Antirrinoside, Asperuloside, Asperulosidic acid, Aucubin, Aucubin Acetate, Aucuboside, Aucubieenin-1-P-i~onialtopidc, Haldrinal, Darlerin, Dartsioeide, Iloschnalosiile, Cantleyoside, Caryoptoeide, Catalpol, Catalpol Yonoacetate, Catalposide, Centapicrin, 7-Chlorodeutziol, Cornin, Uaphylloslde, Deacetyl-Asperuloside, Decaloside, Decapetaloside, 5-9 Dehydro-nepetalactcne, Deoxl-amaropentin, 10-Deoxy Aucubin, Deoxyloeanin, Deutziol, Didrovaltrate, Dihydrofoliamenthin, Dihydropenstemide, Dihydroplumericin, 8-Dihydro Plumericinic acid, Durantoride-I, Elenolide, Epoxydeculoside, Erythroccntaurine, IO-Ethylapodanthoside, Eucommiol, Eustomoruside, Eustomoside, Eustoside, Feretoside, Foliamenthin, Forsythide, Forsythide Methyl Ester, llethyl Grandiiloro side, 11-llethyl Isoside, Lllneroeide, Jlioporoeide, 3lononielittoeirle, 316notropein, Monotronein, Jlorroniside, 3luesaenoside, Saucledd, Seomatatabiol, Sepetalactcne, Suzhenide, Jdontoride, Odontosidc Aretate, I Jleuropein, Opulus Iridoid, Opului lridoid, Onin-arin, 7-Clxologanin, I'aederoelde, I'nederoaidic, I'atrinoside, I'lumericin, Lieptoside, Sarracenin, Scabroside, Scandoside, Scandoride, Srrophularioride, Cutellariosid, ecoealioside, Secologanir, Secolopanin, Ecoivloeanin, Shanzhiside llethyl Ester, Specioside, Stilberiecside, Strictoside, Sn-eroside 1, Swertiamnrin, S-lvestroside-I, yl-estroside-II, Svl-estroside-III, Svrineoside, TLretnoeide, Tecomoside, Tecoside, Teucrium, Teucriuni Lactone B, Teucrium I. actone C, Teucriuni Lactone D, Vaccinioside, Valechlorine, Valeridine, Valerosidate and Taltrate, Haqnlpol.

Methods of the present invention comprise the administration and/or consumption of a combination of a processed plant product and a source of iridoids in an amount designed to produce a desirable physiological response. It will be understood that specific dosage levels of any compositions that will be administered to any particular patient will depend upon a variety of factors, including the patient's age, body weight, general health, gender, diet, time of administration, route of administration, rate of excretion, drug combination, and the severity of the particular diseases undergoing therapy or in the process of incubation.

Studies performed have revealed that Iridoids in combination with a processed Plant product exhibit unexpected synergistic bioactivity including; neuroprotective, anti-tumor, anti-inflammatory, anti-oxidant, cardiovascular, anti-hepatotoxic, choleretic, hypoglycemic, hypolipidemic, antispasmodic, antiviral, antimicrobial, immunomodulator, antiallergic, anti-leishmanial, and molluscicidal effect.

Preferred embodiments are formulated to provide a physiological benefit. For example, some embodiments may provide an anti-inflammatory activity selectively inhibit COX-1/COX-2 and/or by regulating regulate TNF, Nitric oxide and 5-LOX; regulate immunomodulation by increases IFN-secretion; provide antiallergic activity by inhibiting histamine release; provide anti-arthritic activity by inhibiting human neutrophils, regulating elastase enzyme activity, inhibiting the complement pathway; provide antimicrobial activity by inhibiting the growth of various microbials including gram− and gram+ bacteria; providing antifungal activity by inhibiting DNA repair systems; provide anticancer activity by inhibiting cancer cell growth and by being cytotoxic to cancer cells; provide anticoagulant activity by inhibiting platelets aggregations; provide antioxidant activity by providing DPPH scavenging effects; provide antiviral activity including anti-HSV, anti-RSV, and anti-VSV activity; provide antispasmodic activity; provide wound-healing activity by stimulating the growth of human dermal fibroblasts; and provide neuroprotective activities by blocking the release of lactate dehydrogenase (LDH), and enhancing Nerve Growth Factor-potentiating (NGF) activity.

Methods of the present invention also include manufacturing a composition comprising an iridoid source and/or extracts. Each of the methods described above in the discussion relevant to processing the plant products may likewise be utilized to process the constitutive elements of plant being utilized as a source of iridoids.

For example the leaves of one or more of the plants listed above may be processed. For example, some compositions comprise leaf extract and/or leaf juice. Some compositions comprise a leaf serum that is comprised of both leaf extract and fruit juice obtained from one or more plants. Some compositions of the present invention comprise leaf serum and/or various leaf extracts as incorporated into a nutraceutical product ("nutraceutical" herein referring to any product designed to improve the health of living organisms such as human beings or mammals).

In some embodiments of the present invention, the leaf extracts are obtained using the following process. First, relatively dry leaves from the selected plant or plants are collected, cut into small pieces, and placed into a crushing device—preferably a hydraulic press—where the leaf pieces are crushed. In some embodiments, the crushed leaf pieces are then percolated with an alcohol such as ethanol, methanol, ethyl acetate, or other alcohol-based derivatives using methods known in the art. Next, in some embodiments, the alcohol and all alcohol-soluble ingredients are extracted from the crushed leaf pieces, leaving a leaf extract that is then reduced with heat to remove all the liquid therefrom. The resulting dry leaf extract will herein be referred to as the "primary leaf extract."

In some embodiments, the primary leaf extract is subsequently pasteurized. The primary leaf extract may be pasteurized preferably at a temperature ranging from 70 to 80 degrees Celsius and for a period of time sufficient to destroy any objectionable organisms without major chemical alteration of the extract. Pasteurization may also be accomplished according to various radiation techniques or methods.

In some embodiments of the present invention, the pasteurized primary leaf extract is placed into a centrifuge decanter where it is centrifuged to remove or separate any remaining leaf juice therein from other materials, including chlorophyll. Once the centrifuge cycle is completed, the leaf extract is in a relatively purified state. This purified leaf extract is then pasteurized again in a similar manner as discussed above to obtain a purified primary leaf extract.

Preferably, the primary leaf extract, whether pasteurized and/or purified, is further fractionated into two individual fractions: a dry hexane fraction, and an aqueous methanol fraction. This is accomplished preferably in a gas chromatograph containing silicon dioxide and CH2Cl2-MeOH ingredients using methods well known in the art. In some embodiments of the present invention, the methanol fraction is further fractionated to obtain secondary methanol fractions. In some embodiments, the hexane fraction is further fractionated to obtain secondary hexane fractions.

One or more of the leaf extracts, including the primary leaf extract, the hexane fraction, methanol fraction, or any of the secondary hexane or methanol fractions may be combined with the processed plant product(s) to obtain a leaf serum. In some embodiments, the leaf serum is packaged and frozen ready for shipment; in others, it is further incorporated into a nutraceutical product as explained herein.

Some embodiments of the present invention include a composition comprising fruit juice from one or more of the listed plants. Each of the methods described above in the discussion relevant to processing the juice products may likewise be utilized to process the fruit of the plant being utilized as a source of iridoids.

Some embodiments comprise the use of seeds from the list of plants provided. Each of the methods described above in the discussion relevant to processing seeds from the plant may likewise be utilized to process the seeds of plant being utilized as a source of iridoids.

Some embodiments of the present invention may comprise oil extracted from the plant and/or plants selected as the source of iridoids. Each of the methods described above in the discussion relevant to processing the plant to produce an oil extract may likewise be utilized to process the constitutive elements of plant being utilized as a source of iridoids.

Compositions and their Use

The present invention features compositions and methods for providing a desirable physiological effect. Several embodiments of the plant and iridoid compositions comprise various different ingredients, each embodiment comprising one or more forms of a processed plant and a source of iridoids as explained herein.

Compositions of the present invention may comprise any of a number of plant components such as: extract from the leaves of the selected plant, leaf hot water extract, processed leaf ethanol extract, processed leaf steam distillation extract, fruit juice, plant extract, dietary fiber, plant puree juice, plant puree, fruit juice concentrate, puree juice concentrate, freeze concentrated fruit juice, seeds, seed extracts, extracts taken from defatted seeds, and evaporated concentration of fruit juice in combination with a source of iridoids. Compositions of the present invention may also include various other ingredients. Examples of other ingredients include, but are not limited to: artificial flavoring, other natural juices or juice concentrates such as a natural grape juice concentrate or a natural blueberry juice concentrate; carrier ingredients; and others as will be further explained herein.

Any compositions having the leaf extract from the plant or plants being utilized a as source of iridoids and the selected plant leaves, may comprise one or more of the following: the primary leaf extract, the hexane fraction, methanol fraction, the secondary hexane and methanol fractions, the leaf serum, or the nutraceutical leaf product.

In some embodiments of the present invention, active ingredients from the plant or plants being utilized as a source of iridoids and the selected plant may be extracted out using various procedures and processes. For instance, the active ingredients may be isolated and extracted out using alcohol or alcohol-based solutions, such as methanol, ethanol, and ethyl acetate, and other alcohol-based derivatives using methods known in the art. These active ingredients or compounds may be isolated and further fractioned or separated from one another into their constituent parts. Preferably, the compounds are separated or fractioned to identify and isolate any active ingredients that might help to prevent disease, enhance health, or perform other similar functions. In addition, the compounds may be fractioned or separated into their constituent parts to identify and isolate any critical or dependent interactions that might provide the same health-benefiting functions just mentioned.

Any components and compositions of and/or ingredients from the plant or plants being utilized as a source of iridoids may be further incorporated into a nutraceutical product (again, "nutraceutical" herein referring to any product designed to improve the health of living organisms). Examples of nutraceutical products may include, but are not limited to: topical products, oral compositions and various other products as may be further discussed herein.

Oral compositions may take the form of, for example, tablets, lozenges, aqueous or oily suspensions, dispersible powders or granules, emulsions, syrups, or elixirs. Such compositions may contain one or more agents such as sweetening agents, flavoring agents, coloring agents, and preserving agents. They may also contain one or more additional ingredients such as vitamins and minerals, etc. Tablets may be manufactured to contain one or more components and ingredient(s) from the plant or plants being utilized as a source of iridoids in admixture with non-toxic, pharmaceutically acceptable excipients that are suitable for the manufacture of tablets. These excipients may be, for example, inert diluents, granulating and disintegrating agents, binding agents, and lubricating agents. The tablets may be uncoated or they may be coated by known techniques to delay disintegration and absorption in the gastrointestinal tract and thereby provide sustained action over a longer period. For example, a time delay material such as glyceryl monostearate or glyceryl distearate may be used.

Aqueous suspensions may be manufactured to contain the components and ingredient(s) from the plant or plants being utilized as a source of iridoids in admixture with excipients suitable for the manufacture of aqueous suspensions. Examples of such excipients include, but are not limited to: suspending agents such as sodium carboxymethyl-cellulose, methylcellulose, hydroxy-propylmethycellulose, sodium alginate, polyvinyl-pyrrolidone, gum tragacanth and gum acacia; dispersing or wetting agents such as a naturally-occurring phosphatide like lecithin, or condensation products of an alkylene oxide with fatty acids such as polyoxyethylene stearate, or condensation products of ethylene oxide with long chain aliphatic alcohols such as heptadecaethylene-oxycetanol, or condensation products of ethylene oxide with partial esters derived from fatty acids and a hexitol such as polyoxyethylene sorbitor monooleate, or condensation products of ethylene oxide with partial esters derived from fatty acids and hexitol anhydrides such as polyethylene sorbitan monooleate.

Typical sweetening agents may include, but are not limited to: natural sugars derived from corn, sugar beets, sugar cane, potatoes, tapioca, or other starch-containing sources that can be chemically or enzymatically converted to crystalline chunks, powders, and/or syrups. Also, sweeteners can comprise artificial or high-intensity sweeteners, some of which may include aspartame, sucralose, stevia, saccharin, etc. The concentration of sweeteners may be between from 0 to 50 percent by weight of the composition, and more preferably between about 1 and 5 percent by weight.

Typical flavoring agents can include, but are not limited to, artificial and/or natural flavoring ingredients that contribute to palatability. The concentration of flavors may range, for example, from 0 to 15 percent by weight of the composition. Coloring agents may include food-grade artificial or natural coloring agents having a concentration ranging from 0 to 10 percent by weight of the composition.

Typical nutritional ingredients may include vitamins, minerals, trace elements, herbs, botanical extracts, bioactive chemicals, and compounds at concentrations from 0 to 10 percent by weight of the composition. Examples of vitamins include, but are not limited to, vitamins A, B1 through B12, C, D, E, Folic Acid, Pantothenic Acid, Biotin, etc. Examples of minerals and trace elements include, but are not limited to, calcium, chromium, copper, cobalt, boron, magnesium, iron, selenium, manganese, molybdenum, potassium, iodine, zinc, phosphorus, etc. Herbs and botanical extracts may include, but are not limited to, alfalfa grass, bee pollen, chlorella powder, Dong Quai powder, Echinacea root, Gingko Biloba extract, Horsetail herb, Indian mulberry, Shitake mushroom, spirulina seaweed, grape seed extract, etc. Typical bioactive chemicals may include, but are not limited to, caffeine, ephedrine, L-carnitine, creatine, lycopene, etc.

The ingredients to be utilized in a topical dermal product may include any that are safe for internalizing into the body of a mammal and may exist in various forms, such as gels, lotions, creams, ointments, etc., each comprising one or more carrier agents.

In one exemplary embodiment, a composition of the present invention comprises one or more of a processed plant component present in an amount by weight between about 0.01 and 100 percent y weight, and preferably between 0.01 and 95 percent by weight in combination with a processed iridoid source present in an amount by weight between about 0.01 and 100 percent by weight, and preferably between 0.01 and 95 percent by weight. Several embodiments of formulations are included in U.S. Pat. No. 6,214,351, issued on Apr. 10, 2001, which are herein incorporated by reference. However, these compositions are only intended to be exemplary, as one ordinarily skilled in the art will recognize other formulations or compositions comprising the processed product.

In another exemplary embodiment, the internal composition comprises the ingredients of: processed fruit juice or puree juice present in an amount by weight between about 0.1-80 percent; a processed source of iridoids present in an amount by weight between about 0.1-20 percent; and a carrier medium present in an amount by weight between about 20-90 percent.

The processed product and/or processed source of iridoids is the active ingredient or contains one or more active ingredients, such as quercetin, rutin, scopoletin, octoanoic acid, potassium, vitamin C, terpenoids, alkaloids, anthraquinones (such as nordamnacanthal, morindone, rubiandin, B-sitosterol, carotene, vitamin A, flavone glycosides, linoleic acid, Alizarin, amino acides, acubin, L-asperuloside, caproic acid, caprylic acid, ursolic acid, and a putative proxeronine and others. Active ingredients may be extracted utilizing aqueous or organic solvents including various alcohol or alcohol-based solutions, such as methanol, ethanol, and ethyl acetate, and other alcohol-based derivatives using any known process in the art. The active iridoid ingredients and/or quercetin and rutin may be present in amounts by weight ranging from 0.01-10 percent of the total formulation or composition. These amounts may be concentrated as well into a more potent concentration in which they are present in amounts ranging from 10 to 100 percent.

The composition comprising a selected plant and a source of iridoids may be manufactured for oral consumption. It may contain one or more agents selected from the group consisting of sweetening agents, flavoring agents, coloring agents, preserving agents, and other medicinal agents as directed.

The following compositions or formulations represent some of the preferred embodiments contemplated by the present invention. "Fruit" is utilized to refer to the fruit of a plant selected from List A above and "Plant" is utilized to refer to a plant selected from List A above.

Formulation One

| % Range | Ingredient |
| --- | --- |
| 10-80 | *Morinda citrifolia* (Noni) Fruit Nectar from Pure Noni Puree and from Juice Concentrate from French Polynesia |
| 10-80 | *Cornus mas* (Cornelian Cherry) Puree |
| 10-80 | *Cornus officinalis* Reconstituted Juice |
| 10-80 | *Vitis vinifera* (White Grape) Juice Concentrate |
| 10-80 | *Vaccinium corymbosum* (Blueberry) Juice from Concentrate |
| 1-30 | *Prunus cerasus* (Red Sour Cherry) Juice Concentrate |
| 1-30 | *Vitis labrusca* (Concord Grape) Juice Concentrate |
| <1.0 | *Olea eropea* (Olive) Leaf Extract |
| <1.0 | *Vaccinium macrocarpum* (Cranberry) Juice Concentrate |
| <1.0 | Natural Flavor |

Formulation Two

| % Range | Ingredients |
| --- | --- |
| 10-80 | *Morinda citrifolia* (Noni) Fruit Nectar from Pure Noni Puree and from Juice Concentrate from French Polynesia |
| 10-80 | *Cornus Mas* (Cornelian Cherry) |
| 10-80 | *Vitis vinifera* (White Grape) Juice Concentrate |
| 10-80 | *Vaccinium corymbosum* (Blueberry) Juice from Concentrate |
| 1-30 | *Prunus cerasus* (Red Sour Cherry) Juice Concentrate |

-continued

| % Range | Ingredients |
| --- | --- |
| 1-30 | *Vitis labrusca* (Concord Grape) Juice Concentrate |
| <1.0 | *Olea eropea* (Olive) Leaf Extract |
| <1.0 | *Vaccinium macrocarpum* (Cranberry) Juice Concentrate |
| <1.0 | Natural Flavors |

Formulation Three

| % Range | Ingredients |
| --- | --- |
| 10-80 | *Morinda citrifolia* (Noni) Fruit Nectar from Pure Noni Puree and from Juice Concentrate from French Polynesia |
| 10-80 | *Cornus officinalis* Reconstituted Juice |
| 10-80 | *Vitis vinifera* (White Grape) Juice Concentrate |
| 10-80 | *Vaccinium corymbosum* (Blueberry) Juice from Concentrate |
| 1-30 | *Prunus cerasus* (Red Sour Cherry) Juice Concentrate |
| 1-30 | *Vitis labrusca* (Concord Grape) Juice Concentrate |
| <1.0 | *Olea eropea* (Olive) Leaf Extract |
| <1.0 | Natural Flavors |

Formulation Four

| % Range | Ingredient |
| --- | --- |
| 69.29850 | *Morinda citrifolia* (Noni) Fruit Nectar from Pure Noni Puree and from Juice Concentrate from French Polynesia |
| 14.83275 | *Vitis vinifera* (White Grape) Juice Concentrate |
| 13.06150 | *Vaccinium corymbosum* (Blueberry) Juice from Concentrate |
| 1.50000 | *Prunus cerasus* (Red Sour Cherry) Juice Concentrate |
| 1.23725 | *Vitis vinifera* (Red Grape) Juice Concentrate |
| 0.07000 | Natural Flavors |

Formulation Five

| % Range | Ingredient |
| --- | --- |
| 50-100% | Fruit Nectar |
| 10-75% | *Vitis labrusca* (Concord Grape) Juice Concentrate |
| 5-50% | *Vitis vinifera* (White Grape) Juice Concentrate |
| 0-15% | Gum Arabic* |
| 0-15% | Xanthan Gum* |
| 0-5% | Natural Flavor |

*some sizes exclude these ingredients

Formulation Six

| % Range | Ingredient |
| --- | --- |
| 10-75% | Fruit Nectar |
| 10-75% | *Malus pumila* (Apple) Juice Concentrate |
| 5-50% | *Mangifera indica* (Mango) Juice Concentrate |
| 3-30% | *Passiflora edulis* (Passionfruit) Juice Concentrate |
| 0-5% | Natural Flavor |
| 0-15% | Natural Color or Concentrates (apple, cherry, radish, sweet potato) |
| 0-15% | Gum Arabic* |
| 0-15% | Xanthan Gum* |
| 0-15% | Oligofructose |
| 0-15% | Fructose |
| 0-15% | Vegetable Protein Isolate |

*some sizes exclude these ingredients

Formulation Seven

| % Range | Ingredient |
| --- | --- |
| 50-100% | Fruit Puree |
| 10-75% | Leaf Tea |

Formulation Eight

| % Range | Ingredient |
| --- | --- |
| 50-100% | Fruit Nectar |
| 3-30% | Natural Grape Juice Concentrate |
| 3-30% | Natural Blueberry Juice Concentrate |
| 0-5% | Natural Flavors |
| 0-15% | Gum Arabic* |
| 0-15% | Xanthan Gum* |

*some sizes exclude these ingredients

Formulation Nine

| % Range | Ingredient |
| --- | --- |
| 35-90% | Fruit Nectar |
| 15-60% | *Cornus mas* (Cornelian Cherry) Puree |
| 5-50% | *Cornus officinalis* Reconstituted Juice |
| 5-50% | *Vitis vinifera* (White Grape) Juice Concentrate |
| 5-50% | *Vaccinium corymbosum* (Blueberry) Juice from Concentrate |
| 0-15% | *Prunus cerasus* (Red Sour Cherry) Juice Concentrate |
| 0-15% | *Vitis labrusca* (Concord Grape) Juice Concentrate |
| 0-5% | Natural Flavor |
| 0-15% | *Olea europea* (Olive) Leaf Extract |
| 0-15% | *Vaccinium macrocarpum* (Cranberry) Juice Conc. |

*some sizes exclude these ingredients

Formulation Ten

| % Range | Ingredient |
|---|---|
| 35-90% | Fruit Nectar |
| 5-50% | *Vitis vinifera* (White Grape) Juice Concentrate |
| 3-30% | *Malus domestica* (Apple) Juice Concentrate |
| 0-15% | *Ribes nigrum* (Black Currant) Juice Concentrate |
| 0-15% | *Vitis labrusca* (Concord Grape) Juice Concentrate |
| 0-15% | *Vaccinium corymbosum* (Blueberry) Juice Concentrate |
| 0-5% | Natural Flavors |
| 0-15% | *Rubus idaeus* (Red Raspberry) Juice Concentrate |

Formulation Eleven

| % Range | Ingredient |
|---|---|
| 50-95% | Water (Aqua/Eau) |
| 0-15% | Polymethylsilsesquioxane |
| 0-20% | Glycerin |
| 0-20% | Propanediol |
| 0-20% | Cyclopentasiloxane |
| 0-20% | Cyclotetrasiloxane |
| 0-20% | Caprylic/Capric Triglyceride |
| 0-20% | Sodium Polyacrylate |
| 0-20% | Dimethicone |
| 0-15% | Hydrogenated Polydecene |
| 0-15% | Butylene Glycol |
| 0-15% | Cyclohexasiloxane |
| 0-15% | Phenoxyethanol |
| 0-15% | Leaf Juice |
| 0-15% | PEG/PPG-14/4 Dimethicone |
| 0-15% | Dimethiconol |
| 0-15% | *Avena sativa* (Oat) Kernel Extract |
| 0-15% | *Tropaeolum majus* Flower Extract |
| 0-15% | Seed Oil |
| 0-15% | Caprylyl Glycol |
| 0-15% | Aminomethyl Propanol |
| 0-15% | Sodium PCA |
| 0-15% | Ethylhexylglycerin |
| 0-15% | Panthenol |
| 0-5% | Trideceth-6 |
| 0-5% | Hexylene Glycol |
| 0-5% | Tetrasodium EDTA |
| 0-5% | Fragrance (Parfum) |
| 0-5% | Carbomer |
| 0-5% | Polysorbate 20 |
| 0-5% | Sodium Hyaluronate |
| 0-5% | Methylparaben |
| 0-5% | Ethylparaben |
| 0-5% | Propylparaben |
| 0-5% | Butylparaben |
| 0-5% | Isobutylparaben |
| 0-5% | Vegetable Oil |
| 0-5% | Tocopherol |
| 0-5% | Palmitoyl Oligopeptide |
| 0-5% | Palmitoyl Tetrapeptide-7 |
| 0-5% | Phospholipids |
| 0-5% | *Rosmarinus officinalis* (Rosemary) Leaf Extract |
| 0-5% | Tocopheryl Acetate |
| 0-5% | Retinyl Palmitate |
| 0-5% | Ascorbyl Palmitate |
| 0-5% | Quaternium-15 |
| 0-5% | EDTA |

Formulation Twelve

| % Range | Ingredient |
|---|---|
| 50-95% | Water (Aqua/Eau) |
| 3-30% | *Aloe barbadensis* Leaf Juice |
| 0-15% | Caprylic/Capric Triglyceride |
| 0-15% | *Sinorhizobium meliloti* Ferment Filtrate |
| 0-15% | Propanediol |
| 0-15% | *Carthamus tinctorius* (Safflower) Seed Oil |
| 0-15% | *Prunus armeniaca* (Apricot) Kernel Oil |
| 0-15% | Glycerin |
| 0-15% | Cetyl Alcohol |
| 0-15% | Fruit Juice |
| 0-5% | Glyceryl Stearate |
| 0-5% | PEG-100 Stearate |
| 0-5% | Sodium Polyacrylate |
| 0-5% | Cetearyl Alcohol |
| 0-5% | Phenoxyethanol |
| 0-5% | Cyclopentasiloxane |
| 0-5% | Tocopheryl Acetate |
| 0-5% | Aluminum Starch Octenylsuccinate |
| 0-5% | *Avena sativa* (Oat) Kernel Extract |
| 0-5% | Cyclotetrasiloxane |
| 0-5% | Ceteareth-20 |
| 0-5% | Sodium PCA |
| 0-5% | *Hordeum distichon* (Barley) Extract |
| 0-5% | Caprylyl Glycol |
| 0-5% | Ethylhexylglycerin |
| 0-5% | *Santalum album* (Sandalwood) Extract |
| 0-5% | *Phellodendron amurense* Bark Extract |
| 0-5% | Fragrance (Parfum) |
| 0-5% | Dimethiconol |
| 0-5% | Hexylene Glycol |
| 0-5% | Seed Oil |
| 0-5% | Disodium EDTA |
| 0-5% | Cetyl Hydroxyethylcellulose |
| 0-5% | Lecithin |
| 0-5% | Sodium Benzoate |
| 0-5% | Potassium Sorbate |
| 0-5% | Sodium Hyaluronate |
| 0-5% | Trisodium EDTA |
| 0-5% | Tocopherol |
| 0-5% | Vegetable Oil |
| 0-5% | *Rosmarinus officinalis* (Rosemary) Leaf Extract |

Formulation Thirteen

| % Range | Ingredient |
|---|---|
| 50-95% | Water (Aqua/Eau) |
| 3-30% | Caprylic/Capric Triglyceride |
| 0-15% | Glycerin |
| 0-15% | Bis-PEG-15 Methyl Ether Dimethicone |
| 0-15% | Behenyl Alcohol |
| 0-15% | Dimethicone |
| 0-15% | Pentylene Glycol |
| 0-15% | Hydroxyethyl Acrylate/Sodium Acryloyldimethyl Taurate Copolymer |
| 0-15% | Polyglyceryl-3 Stearate |
| 0-15% | Beheneth-5 |
| 0-15% | Silica |
| 0-15% | Cetearyl Alcohol |
| 0-15% | Fruit Juice |
| 0-10% | Seed Oil |
| 0-5% | Phenoxyethanol |
| 0-5% | PEG-40 Hydrogenated Castor Oil |
| 0-5% | Polysorbate 60 |
| 0-5% | Caprylyl Glycol |
| 0-5% | Titanium Dioxide |
| 0-5% | Leaf Juice |

-continued

| % Range | Ingredient |
|---|---|
| 0-5% | Ethylhexylglycerin |
| 0-5% | Hexylene Glycol |
| 0-5% | Tetrahexyldecyl Ascorbate |
| 0-5% | Tocopheryl Acetate |
| 0-5% | *Gardenia jasminoides* Meristem Cell Culture |
| 0-5% | *Olea europaea* (Olive) Leaf Extract |
| 0-5% | Disodium EDTA |
| 0-5% | Steareth-20 |
| 0-5% | *Camellia oleifera* Leaf Extract |
| 0-5% | Iron Oxides |
| 0-5% | Retinyl Palmitate |
| 0-5% | Chlorhexidine Digluconate |
| 0-5% | Xanthan Gum |
| 0-5% | N-Hydroxysuccinimide |
| 0-5% | Vegetable Oil |
| 0-5% | Tocopherol |
| 0-5% | Potassium Sorbate |
| 0-5% | Chrysin |
| 0-5% | Palmitoyl Oligopeptide |
| 0-5% | Palmitoyl Tetrapeptide-7 |
| 0-5% | *Rosmarinus officinalis* (Rosemary) Leaf Extract |

Formulation Fourteen

| % Range | Ingredient |
|---|---|
| 10-75% | Soy Protein Isolate |
| 10-75% | Sugar |
| 3-30% | Inulin (Contains Fructooligosaccharides) |
| 3-30% | Cocoa (processed with alkali) |
| 3-30% | High Oleic Sunflower Oil |
| 0-15% | Corn Syrup Solids |
| 0-15% | Whey Protein Isolate |
| 0-15% | Natural Flavors |
| 0-15% | Milk Protein Concentrate |
| 0-15% | Sodium Caseinate (a Milk Derivative) |
| 0-15% | Maltodextrin |
| 0-15% | Mono & Diglycerides |
| 0-15% | Stevia |
| 0-15% | Dipotassium Phosphate |
| 0-15% | Salt |
| 0-15% | Tricalcium Phosphate |
| 0-15% | Fruit Fiber |
| 0-15% | Xanthan Gum |
| 0-15% | Pea Protein Isolate |
| 0-15% | Soy Lecithin |
| 0-15% | Tocopherols |

Formulation Fifteen

| % Range | Ingredient |
|---|---|
| 10-75% | Soy Protein Isolate |
| 10-75% | Sugar |
| 3-30% | Inulin (Contains Fructo-oligosaccharides) |
| 3-30% | High Oleic Sunflower Oil |
| 3-30% | Corn Syrup Solids |
| 0-15% | Whey Protein Isolate |
| 0-15% | Milk Protein Concentrate |
| 0-15% | Natural and Artificial Flavors |
| 0-15% | Sodium Caseinate (a Milk Derivative) |
| 0-15% | Maltodextrin |
| 0-15% | Mono & Diglycerides |
| 0-15% | Citric Acid |
| 0-15% | Stevia |

-continued

| % Range | Ingredient |
|---|---|
| 0-15% | Beta Carotene |
| 0-15% | Dipotassium Phosphate |
| 0-15% | Salt |
| 0-15% | Tricalcium Phosphate |
| 0-15% | Fruit Fiber |
| 0-15% | Xanthan Gum |
| 0-15% | Pea Protein Isolate |
| 0-15% | Soy Lecithin |
| 0-15% | Tocopherols |

Formulation Sixteen

| % Range | Ingredient |
|---|---|
| 10-75% | Soy Protein Isolate |
| 10-75% | Sugar |
| 3-30% | Inulin (Contains Fructo-oligosaccharides) |
| 3-30% | High Oleic Sunflower Oil |
| 3-30% | Corn Syrup Solids |
| 0-15% | Whey Protein Isolate |
| 0-15% | Milk Protein Concentrate |
| 0-15% | Natural and Artificial Flavors |
| 0-15% | Sodium Caseinate (a Milk Derivative) |
| 0-15% | Maltodextrin |
| 0-15% | Mono & Diglycerides |
| 0-15% | Stevia |
| 0-15% | Dipotassium Phosphate |
| 0-15% | Salt |
| 0-15% | Tricalcium Phosphate |
| 0-15% | Fruit Fiber |
| 0-15% | Xanthan Gum |
| 0-15% | Pea Protein Isolate |
| 0-15% | Soy Lecithin |
| 0-15% | Tocopherols |

Formulation Seventeen

| % Range | Ingredient |
|---|---|
| 10-75% | Apple Juice |
| 10-75% | Coconut Water |
| 5-50% | Mango Puree |
| 5-50% | Pineapple Juice |
| 3-30% | Orange Juice |
| 3-30% | Prune Juice |
| 0-15% | Polydextrose |
| 0-15% | Acerola Cherry Juice |
| 0-15% | Passion Fruit Juice |
| 0-15% | Fruit Puree |
| 0-15% | *Aloe barbadensis* (Aloe Vera) Gel |
| 0-15% | Natural Flavors |
| 0-15% | Deglycyrrhizinated Licorice |
| 0-15% | *Taraxacum officinale* (Dandelion) Root |

Formulation Eighteen

| % Range | Ingredient |
| --- | --- |
| 35-90% | Sugar |
| 5-50% | Psyllium Husk Fiber |
| 5-50% | Oat Seed Fiber (contains Beta Glucan) |
| 0-15% | Inulin (from Chicory Root) |
| 0-15% | Citric Acid |
| 0-15% | Natural Flavors |
| 0-15% | Maltodextrin |
| 0-15% | Beet Juice (Natural Color) |
| 0-15% | Stevia |
| 0-15% | Turmeric (Natural Color) |
| 0-15% | Dehydrated Lemon Juice |
| 0-15% | Fruit Fiber |
| 0-15% | Silicon Dioxide |

Formulation Nineteen

| % Range | Ingredient |
| --- | --- |
| 35-90% | Sugar |
| 5-50% | Psyllium Husk Fiber |
| 5-50% | Oat Seed Fiber (Contains Beta Glucan) |
| 0-15% | Inulin (from Chicory Root) |
| 0-15% | Citric Acid |
| 0-15% | Natural Flavors |
| 0-15% | Beta Carotene (Natural Color) |
| 0-15% | Maltodextrin |
| 0-15% | Fruit Fiber |
| 0-15% | Stevia |
| 0-15% | Dehydrated Orange Juice from concentrate |

Formulation Twenty

| % Range | Ingredient |
| --- | --- |
| 10-50% | Rolled Oats |
| 3-30% | Soy Protein Isolate |
| 3-30% | Rice Flour |
| 3-30% | Salt |
| 0-15% | Coconut |
| 0-30% | Corn Syrup |
| 5-35% | Brown Rice Syrup |
| 0-15% | Glycerin |
| 0-15% | Sea Salt |
| 0-75% | Sugar |
| 0-30% | Chocolate Liquor |
| 0-30% | Cocoa Butter |
| 0-30% | Soya Lecithin (an emulsifier) |
| 0-30% | Vanilla Extract |
| 0-15% | Brown Sugar |
| 0-20% | Natural Flavors |
| 0-15% | High Oleic Sunflower Oil |
| 0-30% | Fruit Juice |
| 0-30% | Natural Grape Juice Concentrate |
| 0-30% | Natural Blueberry Juice Concentrate |
| 0-15% | Molasses |
| 5-50% | Fractionated Palm Kernel Oil |
| 5-50% | Cocoa Processed with Alkali |
| 5-50% | Lactose |
| 5-50% | Palm Oil |
| 5-50% | Soy Lecithin (an emulsifier) |
| 5-50% | Vanilla |
| 0-15% | Soy Protein Isolate |
| 0-15% | Lecithin |
| 0-15% | Whey Protein Isolate |
| 0-15% | Whey Protein Concentrate |
| 0-15% | Calcium Caseinate (a milk derivative) |

Formulation Twenty-One

| % Range | Ingredient |
| --- | --- |
| 0-30% | Soy Protein Isolate |
| 0-30% | Rice Flour |
| 0-30% | Salt |
| 0-40% | Rolled Oats |
| 5-50% | Brown Rice Syrup |
| 5-50% | Corn Syrup |
| 0-15% | Glycerin |
| 0-15% | Sugar |
| 5-50% | Peanuts |
| 0-15% | Peanut Salt |
| 0-15% | Peanut Flour |
| 0-15% | Peanut Oil |
| 0-30% | Glucose |
| 3-30% | Sugar |
| 3-30% | Modified Palm Kernel Oil |
| 3-30% | Water |
| 3-30% | Skim Milk Powder |
| 3-30% | Glycerin |
| 3-30% | Soy Lecithin |
| 3-30% | Artificial Flavor |
| 3-30% | Salted Butter |
| 3-30% | Sodium Citrate |
| 3-30% | Fractionated Palm Kernel Oil |
| 3-30% | Cocoa Processed with Alkali |
| 3-30% | Lactose |
| 3-30% | Palm Oil |
| 3-30% | Soy Lecithin (an emulsifier) |
| 3-30% | Vanilla |
| 0-15% | Natural and Artificial Flavor |
| 0-30% | Fruit juice |
| 0-30% | Natural Grape Juice Concentrate |
| 0-30% | Natural Blueberry Juice Concentrate |
| 0-30% | Natural Flavors |
| 0-15% | Soy Protein Isolate |
| 0-15% | Lecithin |
| 0-15% | Whey Protein Isolate |
| 0-15% | Whey Protein Concentrate |
| 0-15% | Calcium Caseinate (a milk derivative) |

Formulation Twenty-Two

| % Range | Ingredient |
| --- | --- |
| 5-50% | Calcium Carbonate |
| 5-50% | Microcrystalline Cellulose |
| 5-50% | Ascorbic Acid |
| 3-30% | Magnesium Oxide |
| 3-30% | Stearic Acid |
| 3-30% | Zinc Amino Acid Chelate |
| 0-15% | d-alpha Tocopheryl Succinate |
| 0-15% | Selenium Chelate |
| 0-15% | Vitamin B6 (Pyridoxine HCl) |
| 0-15% | Vitamin B1 (Thiamin Mononitrate) |
| 0-15% | Pantothenic Acid (d-Calcium Pantothenate) |
| 0-15% | Maltodextrin |

| % Range | Ingredient |
|---|---|
| 0-15% | Riboflavin |
| 0-15% | Beta Carotene |
| 0-15% | Croscarmellose Sodium |
| 0-15% | Magnesium Stearate |
| 0-15% | Silicon Dioxide |
| 0-15% | Dicalcium Phosphate |
| 0-15% | Coating (Sodium Carboxymethylcellulose, Dextrin, Dextrose, Medium Chain Triglycerides) |
| 0-15% | Niacinamide |
| 0-15% | Chromium Chelate |
| 0-15% | Copper Gluconate |
| 0-15% | Vitamin K1 (Phytonadione) |
| 0-15% | Hydroxypropyl methylcellulose |
| 0-15% | Vitamin D3 (Cholecalciferol) |
| 0-15% | Fruit pulp |
| 0-15% | Folic Acid |
| 0-15% | Cellulose |
| 0-15% | Biotin |
| 0-15% | Vitamin B12 (Cyanocobalamine) |

Formulation Twenty-Three

| % Range | Ingredient |
|---|---|
| 5-50% | Calcium Carbonate |
| 5-50% | Microcrystalline Cellulose |
| 5-50% | Ascorbic Acid |
| 3-30% | Magnesium Oxide |
| 3-30% | Stearic Acid |
| 3-30% | Selenium Chelate |
| 0-15% | Zinc Amino Acid Chelate |
| 0-15% | d-alpha Tocopheryl Succinate |
| 0-15% | Vitamin B6 (Pyridoxine HCl) |
| 0-15% | Ferrous Chelate |
| 0-15% | Pantothenic Acid (d-Calcium Pantothenate) |
| 0-15% | Vitamin B1 (Thiamin Mononitrate) |
| 0-15% | Riboflavin |
| 0-15% | Maltodextrin |
| 0-15% | Beta Carotene |
| 0-15% | Niacinamide |
| 0-15% | Croscarmellose Sodium |
| 0-15% | Magnesium Stearate |
| 0-15% | Silicon Dioxide |
| 0-15% | Dicalcium Phosphate |
| 0-15% | Coating (Sodium Carboxymethylcellulose, Dextrin, Dextrose, Medium Chain Triglycerides |
| 0-15% | Sodium Citrate) |
| 0-15% | Vitamin K1 (Phytonadione) |
| 0-15% | Chromium Chelate |
| 0-15% | Copper Gluconate |
| 0-15% | Hydroxypropyl methylcellulose |
| 0-15% | Vitamin D3 (Cholecalciferol) |
| 0-15% | Fruit Pulp |
| 0-15% | Folic Acid |
| 0-15% | Cellulose |
| 0-15% | Biotin |
| 0-15% | Vitamin B12 (Cyanocobalamin) |

Formulation Twenty-Four

| % Range | Ingredient |
|---|---|
| 35-90% | Fruit Puree |
| 5-50% | Purified Water |
| 5-50% | Methylsulfonylmethane (MSM) |
| 3-30% | Glucosamine HCl |
| 0-15% | Pulp |
| 0-15% | Soy Lecithin |
| 0-15% | dl-alpha Tocopheryl Acetate (Vitamin E) |
| 0-15% | Flaxseed Oil |
| 0-15% | Priopionic Acid |
| 0-15% | Xanthan Gum |
| 0-15% | Sunflower Oil |
| 0-15% | Mixed Tocopherols |
| 0-15% | Rosemary Extract |

Formulation Twenty-Five

| % Range | Ingredient |
|---|---|
| 35-90% | Fruit Puree |
| 10-75% | Purified Water |
| 0-15% | Pulp |
| 0-15% | Soy Lecithin |
| 0-15% | dl-alpha Tocopheryl Acetate (Vitamin E) |
| 0-15% | Flaxseed Oil |
| 0-15% | Priopionic Acid |
| 0-15% | Xanthan Gum |
| 0-15% | Sunflower Oil |
| 0-15% | Mixed Tocopherols |
| 0-15% | Rosemary Extract |

Formulation Twenty-Six

| % Range | Ingredient |
|---|---|
| 50-100% | Water (Aqua) |
| 0-15% | Polyacrylamide |
| 0-15% | Fruit Juice |
| 0-15% | 2-Phenoxyethanol |
| 0-15% | C13-14 Isoparaffin |
| 0-15% | Caprylyl Glycol |
| 0-15% | Fragrance |
| 0-15% | Laureth-7 |
| 0-15% | Potassium Sorbate |
| 0-15% | Tetrasodium EDTA |
| 0-15% | FD&C Red #33 |
| 0-15% | Ethanol |
| 0-15% | FD&C Blue #1 |
| 0-15% | Sodium Hydroxide |
| 0-15% | Leaf Extract |

Formulation Twenty-Seven

| % Range | Ingredient |
|---|---|
| 35-90% | Purified Water |
| 10-75% | Fruit Puree |
| 0-15% | Soy Lecithin |
| 0-15% | Natural Mesquite Smoke Flavor |
| 0-15% | Fish Oil |
| 0-15% | Safflower Oil |
| 0-15% | Flaxseed Oil |

-continued

| % Range | Ingredient |
|---|---|
| 0-15% | dl-alpha Tocopheryl Oil (Vitamin E) |
| 0-15% | Microalgae Oil |
| 0-15% | Glucosamine HCl |
| 0-15% | Xanthan Gum |
| 0-15% | Priopionic Acid |
| 0-15% | Cetyl Myristoleate |
| 0-15% | L-Threonine |
| 0-15% | Sunflower Oil |
| 0-15% | Mixed Tocopherols |
| 0-15% | Rosemary Extract |

Formulation Twenty-Eight

| % Range | Ingredient |
|---|---|
| 35-90% | Purified Water |
| 10-75% | Fruit Puree |
| 0-15% | Natural Mesquite Smoke Flavor |
| 0-15% | Fish Oil |
| 0-15% | Soy Lecithin |
| 0-15% | Safflower Oil |
| 0-15% | dl-alpha Tocopheryl Oil (Vitamin E) |
| 0-15% | Flaxseed Oil |
| 0-15% | Xanthan Gum |
| 0-15% | Microalgae Oil |
| 0-15% | Priopionic Acid |
| 0-15% | Cetyl Myristoleate |
| 0-15% | Sunflower Oil |
| 0-15% | Mixed Tocopherols |
| 0-15% | Rosemary Extract |

Formulation Twenty-Nine

| % Range | Ingredient |
|---|---|
| 10-75% | Water |
| 5-50% | Wheat Flour |
| 5-50% | Fruit Puree |
| 5-50% | Chicken Meat |
| 3-30% | Corn Flour |
| 3-30% | Wheat Gluten |
| 0-15% | Sugar |
| 0-15% | Gelatin, tech grade |
| 0-15% | Natural Smoke Flavor |
| 0-15% | Glycerin |
| 0-15% | Dextrose |
| 0-15% | Garlic Powder |
| 0-15% | Safflawer Seed Oil |
| 0-15% | Salt |
| 0-15% | Phosphoric Acid |
| 0-15% | Soy Lecithin |
| 0-15% | Onion Powder |
| 0-15% | Fish Oil |
| 0-15% | Potassium Sorbate |
| 0-15% | Flax seed Oil |
| 0-15% | Caramel Color |
| 0-15% | dl-alpha Tocopheryl Acetate |
| 0-15% | Propionic Acid |
| 0-15% | Xanthan Gum |
| 0-15% | Sunflower Oil |
| 0-15% | Mixed Tocopherols |
| 0-15% | Rosemary Extract |

Formulation Thirty

| % Range | Ingredient |
|---|---|
| 35-90% | Fruit Puree |
| 10-75% | Purified Water |
| 0-15% | pulp |
| 0-15% | dl-alpha Tocopheryl Oil (Vitamin E) |
| 0-15% | Soy Lecithin |
| 0-15% | Propionic Acid |
| 0-15% | Flaxseed Oil |
| 0-15% | Xanthan Gum |
| 0-15% | Sunflower Oil |
| 0-15% | Mixed Tocopherols |
| 0-15% | Rosemary Extract |

Formulation Thirty-One

| % Range | Ingredient |
|---|---|
| 35-90% | Fruit Puree Organic |
| 10-75% | Water |

Formulation Thirty-Two

| % Range | Ingredient |
|---|---|
| 50-100% | Fruit Puree |
| 0-15% | Pulp |
| 0-15% | dl-alpha Tocopheryl Oil (Vitamin E) |
| 0-15% | Microalgae Oil |
| 0-15% | Propionic Acid |
| 0-15% | Xanthan Gum |
| 0-15% | Sunflower Oil |
| 0-15% | Mixed Tocopherols |
| 0-15% | Rosemary Extract |

Formulation Thirty-Three

| % Range | Ingredient |
|---|---|
| 35-90% | Fruit Puree Organic |
| 10-75% | Water |

Formulation Thirty-Four

| % Range | Ingredient |
|---|---|
| 50-100% | Clarified Fruit Puree |

Formulation Thirty-Five

| % Range | Ingredient |
|---|---|
| 50-100% | Clarified Fruit Puree |

Formulation Thirty-Six

| % Range | Ingredient |
|---|---|
| 50-100% | Clarified Fruit Puree |

Formulation Thirty-Seven

| % Range | Ingredient |
|---|---|
| 50-100% | Clarified Fruit Puree |

Formulation Thirty-Eight

| % Range | Ingredient |
|---|---|
| 10-75% | Plant Sterols |
| 5-50% | Calcium Carbonate |
| 5-50% | Vegetable Capsules |
| 3-30% | Microcrystalline Cellulose |
| 3-30% | Acerola Extract (*Malpighia glabra linne*) |
| 3-30% | Magnesium Oxide |
| 0-15% | Niacinamide Yeast |
| 0-15% | Maltodextrin |
| 0-15% | Zinc Amino Acid Chelate |
| 0-15% | Biotin Yeast |
| 0-15% | Folic Acid Yeast |
| 0-15% | Pantothenic Acid Yeast |
| 0-15% | Leaf |
| 0-15% | Fruit |
| 0-15% | Selenium Chelate |
| 0-15% | Organic Rice Flour |
| 0-15% | Silica |
| 0-15% | d-alpha Tocopheryl Succinate |
| 0-15% | Kelp (*Laminaria digitata*) |
| 0-15% | Manganese Chelate |
| 0-15% | Berry Blend (see formula or label for list) |
| 0-15% | Quercetin |
| 0-15% | Riboflavin Yeast |
| 0-15% | Copper Gluconate |
| 0-15% | Modified Food Starch |
| 0-15% | Vitamin B6 Yeast |
| 0-15% | Daikon Sprout (*Raphanus sativus*) |
| 0-15% | Kale Sprout (*Brassica oleracea*) |
| 0-15% | Broccoli Sprout (*Brassica oleracea*) |
| 0-15% | Cabbage Sprout (*Brassica oleracia*) |
| 0-15% | Garlic Bulb (*Allium Sativum*) |
| 0-15% | Thiamin Yeast |
| 0-15% | Chromium Chelate |
| 0-15% | Vitamin D2 (Ergocalciferol) |
| 0-15% | Natural Beta Carotene |
| 0-15% | Molybdenum Chelate |
| 0-15% | Vitamin B12 Yeast |
| 0-15% | Water |
| 0-15% | Ethyl Cellulose |
| 0-15% | dl-Alpha Tocopherol |

Formulation Thirty-Nine

| % Range | Ingredient |
|---|---|
| 35-90% | *Camellia sinensis* (Green Tea) Leaf |
| 5-50% | Leaf Tea |
| 5-50% | *Jasminum odoratissimum* (Jasmine) Flowers |

Formulation Fourty

| % Range | Ingredient |
|---|---|
| 0-100% | Leaf |

Formulation Fourty-One

| % Range | Ingredient |
|---|---|
| 35-90% | Water (Aqua) |
| 10-75% | Leaf Juice |
| 3-30% | Pentylene Glycol |
| 0-15% | Acrylates/C10-30 Alkyl Acrylate Crosspolymer |
| 0-15% | Butylene Glycol |
| 0-15% | Potassium Hydroxide |
| 0-15% | Alcohol |
| 0-15% | *Vanilla tahitensis* (Vanilla) Fruit Extract |
| 0-15% | Phenoxyethanol |
| 0-15% | PEG-8 Laurate |
| 0-15% | Laureth-4 |
| 0-15% | Sodium Dehydroacetate |
| 0-15% | Disodium EDTA |
| 0-15% | Leaf Extract |
| 0-15% | Fragrance (Parfum) |

Formulation Fourty-Two

| % Range | Ingredient |
|---|---|
| 35-90% | Water (Aqua) |
| 10-75% | Leaf Juice |
| 3-30% | Pentylene Glycol |
| 0-15% | Butylene Glycol |
| 0-15% | Ethoxydiglycol |
| 0-15% | Phenoxyethanol |
| 0-15% | PEG 8 Laurate |
| 0-15% | Laureth-4 |
| 0-15% | Sodium Dehydroacetate |
| 0-15% | Disodium EDTA |
| 0-15% | Sodium Citrate |
| 0-15% | Citric Acid |

-continued

| % Range | Ingredient |
|---|---|
| 0-15% | Leaf Extract |
| 0-15% | Fragrance |
| 0-15% | *Vanilla tahitensis* (Vanilla) Fruit Extract |
| 0-15% | Methylparaben |
| 0-15% | Propylparaben |

Formulation Fourty-Three

| % Range | Ingredient |
|---|---|
| 50-100% | Seed Oil |
| 0-15% | Vegetable Oil |
| 0-15% | Tocopherol |
| 0-15% | *Rosmarinus officinalis* (Rosemary) Leaf Extract |

Formulation Fourty-Four

| % Range | Ingredient |
|---|---|
| 10-75% | Milk Protein Isolate |
| 10-75% | Soy Protein Isolated |
| 10-75% | Whey Protein Isolate |
| 5-50% | Dutch Cocoa |
| 5-50% | Inulin |
| 5-50% | High Oleic Sunflower Oil |
| 0-15% | Cereal Solids/Corn Syrup Solids |
| 0-15% | Natural and Artificial Flavors |
| 0-15% | Egg Albumin |
| 0-15% | Cellulose Gel |
| 0-15% | Salt |
| 0-15% | Lecithin (from Soy and Egg) |
| 0-15% | Sodium Caseinate (A milk derivative) |
| 0-15% | Mono and Diglycerides |
| 0-15% | Dipotassium Phosphate |
| 0-15% | Maltodextrin |
| 0-15% | Silicon Dioxide |
| 0-15% | Sucralose |
| 0-15% | Pulp |
| 0-15% | Mixed Tocopherols |
| 0-15% | Magnesium Carbonate |

Formulation Fourty-Five

| % Range | Ingredient |
|---|---|
| 10-75% | Fructose |
| 5-50% | Isolated Soy Protein |
| 5-50% | Milk Protein Isolate |
| 5-50% | Whey Protein Isolate |
| 3-30% | Dutch Cocoa |
| 0-15% | Inulin |
| 0-15% | High Oleic Sunflower Oil |
| 0-15% | Cereal Solids/Corn Syrup Solids |
| 0-15% | Natural and Artificial Flavors |
| 0-15% | Egg Albumin |
| 0-15% | Cellulose Gel |
| 0-15% | Salt |
| 0-15% | Sodium Caseinate (A milk derivative) |
| 0-15% | Mono-and Diglycerides |
| 0-15% | Dipotassium Phosphate |

-continued

| % Range | Ingredient |
|---|---|
| 0-15% | Malto-dextrin |
| 0-15% | Silicon Dioxide |
| 0-15% | Soy Lecithin |
| 0-15% | Pulp |
| 0-15% | Mixed Tocopherols |
| 0-15% | Magnesium Carbonate |

Formulation Fourty-Six

| % Range | Ingredient |
|---|---|
| 10-75% | Milk Protein Isolate |
| 10-75% | Soy Protein Isolate |
| 10-75% | Whey Protein Isolate |
| 5-50% | High Oleic Sunflower Oil |
| 3-30% | Cereal Solids/Corn Syrup Solids |
| 3-30% | Inulin |
| 0-15% | Artificial Flavors |
| 0-15% | Cellulose Gel |
| 0-15% | Egg Albumin |
| 0-15% | Sodium Caseinate (A milk derivative) |
| 0-15% | Lecithin (from Soy and Egg) |
| 0-15% | Mono and Diglycerides |
| 0-15% | Dipotassium Phosphate |
| 0-15% | Silicon Dioxide |
| 0-15% | Malto-dextrin |
| 0-15% | Sucralose |
| 0-15% | Pulp |
| 0-15% | Mixed Tocopherols |

Formulation Fourty-Seven

| % Range | Ingredient |
|---|---|
| 10-75% | Fructose |
| 5-50% | Milk Protein Isolate |
| 5-50% | Soy Protein Isolate |
| 5-50% | Whey Protein Isolate |
| 3-30% | Inulin (contains Fructooligosaccharides) |
| 0-15% | High Oleic Sunflower Oil |
| 0-15% | Corn Syrup Solids |
| 0-15% | Artificial Flavors |
| 0-15% | Cellulose Gel |
| 0-15% | Egg Albumin |
| 0-15% | Maltodextrin |
| 0-15% | Sodium Caseinate (a Milk Derivative) |
| 0-15% | Mono and Diglycerides |
| 0-15% | Dipotassium Phosphate |
| 0-15% | Lecithin |
| 0-15% | Tricalcium Phosphate |
| 0-15% | Fruit Powder |
| 0-15% | Tocopherols |

Formulation Fourty-Eight

| % Range | Ingredient |
|---|---|
| 35-90% | Corn Syrup |
| 35-90% | Sugar |
| 3-30% | Palm Oil |

-continued

| % Range | Ingredient |
|---|---|
| 0-15% | Fruit juice, Natural Grape Juice Concentrate, Natural Blueberry Juice Concentrate, Natural Flavors |
| 0-15% | Mono-and Diglycerides |
| 0-15% | Citric Acid |
| 0-15% | Natural Colors |
| 0-15% | Natural Flavors |
| 0-15% | Soy Lecithin |
| 0-15% | Salt |

Formulation Fourty-Nine

| % Range | Ingredient |
|---|---|
| 35-90% | Corn Syrup |
| 35-90% | Sugar |
| 3-30% | Palm Oil |
| 0-15% | Fruit juice, Natural Grape Juice Concentrate, Natural Blueberry Juice Concentrate, Natural Flavors |
| 0-15% | Mono-and Diglycerides |
| 0-15% | Citric Acid |
| 0-15% | Natural Colors |
| 0-15% | Natural Flavors |
| 0-15% | Soy Lecithin |
| 0-15% | Salt |

Formulation Fifty

| % Range | Ingredient |
|---|---|
| 35-90% | Fruit Juice |
| 5-50% | *Hypericum perforatum* (St. Johns Wort) Extract |
| 5-50% | *Passiflora incarnata* (Passion Flower) Extract |
| 3-30% | Fruit Pulp |
| 0-15% | Citric acid |

Formulation Fifty-One

| % Range | Ingredient |
|---|---|
| 50-100% | Fruit Juice |
| 3-30% | *Panax ginseng* Root Extract |
| 3-30% | *Eleutherococcus senticosus* Root Extract |
| 0-15% | *Schisandra chinensis* Fruit Extract |
| 0-15% | Grape Juice Concentrate |
| 0-15% | Apple Juice Concentrate |
| 0-15% | Pear Juice Concentrate |
| 0-15% | Dextrin |
| 0-15% | Citric acid |

Formulation Fifty-Two

| % Range | Ingredient |
|---|---|
| 35-90% | Fruit Juice |
| 5-50% | Fruit Pulp |
| 3-30% | *Crataegus pinnatifida* (Chinese Hawthorn) Berry Extract |
| 0-15% | *Commiphora mukul* (Guggul) Resin Extract |
| 0-15% | *Zingiber officinale* (Ginger) Rhizome Extract |
| 0-15% | Coenzyme Q10 (Ubiquinone) |
| 0-15% | Citric acid |

Formulation Fifty-Three

| % Range | Ingredient |
|---|---|
| 35-90% | Fruit Juice |
| 5-50% | Fruit Pulp |
| 5-50% | Glucosamine HCL |
| 0-15% | *Curcuma longa* (Curcumin) Root Extract |
| 0-15% | Citric acid |

Formulation Fifty-Four

| % Range | Ingredient |
|---|---|
| 0-100% | Fruit Juice Concentrate |

Formulation Fifty-Five

| % Range | Ingredient |
|---|---|
| 35-90% | Fruit Juice |
| 5-50% | Fruit Pulp |
| 3-30% | *Bacopa monnieri* (Bacopa) Plant Extract |
| 0-15% | *Ginkgo biloba* (Ginkgo) Leaf Extract |
| 0-15% | *Lycopodium serratum* (Huperzine) Plant Extract |
| 0-15% | Citric acid |

Formulation Fifty-Six

| % Range | Ingredient |
|---|---|
| 35-95% | Water/Aqua |
| 0-15% | *Cocos nucifera* (Coconut) Oil |
| 0-15% | *Aleurites moluccana* (Kukui) Seed Oil |
| 0-15% | *Macadamia integrifolia* (Macadamia) Seed Oil |
| 0-15% | Cetearyl Alcohol |
| 0-15% | *Butyrospermum parkii* (Shea Butter) |
| 0-15% | Glycerin |
| 0-15% | Glyceryl Stearate |
| 0-15% | PEG-100 Stearate |
| 0-15% | *Theobroma cacao* (Cocoa) Seed Butter |
| 0-15% | *Mangifera indica* (Mango) Seed Butter |
| 0-15% | Dimethicone |

-continued

| % Range | Ingredient |
|---|---|
| 0-15% | Ceteareth-20 |
| 0-15% | Phenoxyethanol |
| 0-15% | Caprylyl Glycol |
| 0-15% | Fragrance |
| 0-15% | Carbomer |
| 0-15% | Tocopheryl Acetate |
| 0-15% | Seed Oil |
| 0-15% | Aminomethyl Propanol |
| 0-15% | Butylene Glycol |
| 0-15% | Potassium Sorbate |
| 0-15% | Disodium EDTA |
| 0-15% | *Pikea robusta* (Red Algae) Extract |
| 0-15% | *Adiantum pedatum* (Maidenhair) Extract |
| 0-15% | *Citrus aurantifolia* (Lime) Fruit Extract |
| 0-15% | Tocopherol |
| 0-15% | Honey Extract |
| 0-15% | *Gardenia tahitensis* (Tiare) Flower |

Formulation Fifty-Seven

| % Range | Ingredient |
|---|---|
| 35-95% | Water/Aqua |
| 0-15% | *Cocos nucifera* (Coconut) Oil |
| 0-15% | *Aleurites moluccana* (Kukui) Seed Oil |
| 0-15% | *Macadamia integrifolia* (Macadamia) Seed Oil |
| 0-15% | Cetearyl Alcohol |
| 0-15% | *Butyrospermum parkii* (Shea Butter) |
| 0-15% | Glycerin |
| 0-15% | Glyceryl Stearate |
| 0-15% | PEG-100 Stearate |
| 0-15% | *Mangifera indica* (Mango) Seed Butter |
| 0-15% | *Theobroma cacao* (Cocoa) Seed Butter |
| 0-15% | Dimethicone |
| 0-15% | Ceteareth-20 |
| 0-15% | Phenoxyethanol |
| 0-15% | Caprylyl Glycol |
| 0-15% | Fragrance (Parfum) |
| 0-15% | Carbomer |
| 0-15% | Tocopheryl Acetate |
| 0-15% | Seed Oil |
| 0-15% | Aminomethyl Propanol |
| 0-15% | Butylene Glycol |
| 0-15% | Potassium Sorbate |
| 0-15% | Disodium EDTA |
| 0-15% | *Pikea robusta* (Red Algae) Extract |
| 0-15% | *Adiantum pedatum* (Maidenhair) Extract |
| 0-15% | *Citrus aurantifolia* (Lime) Fruit Extract |
| 0-15% | Tocopherol |
| 0-15% | *Carica papaya* (Papaya) Fruit Extract |
| 0-15% | *Vanilla tahitensis* Fruit Extract |
| 0-15% | Honey Extract |
| 0-15% | Vegetable Oil |
| 0-15% | *Gardenia tahitensis* (Tiare) Flower |
| 0-15% | *Rosmarinus officinalis* (Rosemary) Leaf Extract |

Formulation Fifty-Eight

| % Range | Ingredient |
|---|---|
| 35-95% | Water/Aqua |
| 0-15% | *Cocos nucifera* (Coconut) Oil |
| 0-15% | *Aleurites moluccana* (Kukui) Seed Oil |
| 0-15% | *Macadamia integrifolia* (Macadamia) Seed Oil |
| 0-15% | Cetearyl Alcohol |
| 0-15% | *Butyrospermum parkii* (Shea Butter) |

-continued

| % Range | Ingredient |
|---|---|
| 0-15% | Glycerin |
| 0-15% | Glyceryl Stearate |
| 0-15% | PEG-100 Stearate |
| 0-15% | *Theobroma Cacao* (Cocoa) Seed Butter |
| 0-15% | *Mangifera indica* (Mango) Seed Butter |
| 0-15% | Dimethicone |
| 0-15% | Ceteareth-20 |
| 0-15% | Phenoxyethanol |
| 0-15% | Caprylyl Glycol |
| 0-15% | Fragrance |
| 0-15% | Carbomer |
| 0-15% | Tocopheryl Acetate |
| 0-15% | Seed Oil |
| 0-15% | Aminomethyl Propanol |
| 0-15% | Butylene Glycol |
| 0-15% | Potassium Sorbate |
| 0-15% | Disodium EDTA |
| 0-15% | *Pikea robusta* (Red Algae) Extract |
| 0-15% | *Adiantum pedatum* (Maidenhair) Extract |
| 0-15% | *Citrus aurantifolia* (Lime) Fruit Extract |
| 0-15% | Tocopherol |
| 0-15% | *Mangifera indica* (Mango) Fruit Extract |
| 0-15% | *Bougainvillea glabra* (Bougainvillea) Flower Extract |
| 0-15% | Honey Extract |
| 0-15% | *Gardenia tahitensis* (Tiare) Flower |

Formulation Fifty-Nine

| % Range | Ingredient |
|---|---|
| 35-95% | Water/Aqua |
| 0-15% | *Cocos nucifera* (Coconut) Oil |
| 0-15% | *Aleurites moluccana* (Kukui) Seed Oil |
| 0-15% | *Macadamia integrifolia* (Macadamia) Seed Oil |
| 0-15% | Cetearyl Alcohol |
| 0-15% | *Butyrospermum parkii* (Shea Butter) |
| 0-15% | Glycerin |
| 0-15% | Glyceryl Stearate |
| 0-15% | PEG-100 Stearate |
| 0-15% | *Theobroma cacao* (Cocoa) Seed Butter |
| 0-15% | *Mangifera indica* (Mango) Seed Butter |
| 0-15% | Dimethicone |
| 0-15% | Ceteareth-20 |
| 0-15% | Phenoxyethanol |
| 0-15% | Caprylyl Glycol |
| 0-15% | Fragrance (Parfum) |
| 0-15% | Carbomer |
| 0-15% | Tocopheryl Acetate |
| 0-15% | Seed Oil |
| 0-15% | Aminomethyl Propanol |
| 0-15% | Butylene Glycol |
| 0-15% | Potassium Sorbate |
| 0-15% | Disodium EDTA |
| 0-15% | *Pikea robusta* (Red Algae) Extract |
| 0-15% | *Adiantum pedatum* (Maidenhair) Extract |
| 0-15% | *Citrus aurantifolia* (Lime) Fruit Extract |
| 0-15% | Tocopherol |
| 0-15% | *Prunus persica* (Peach) Fruit Extract |
| 0-15% | *Carica papaya* (Papaya) Fruit Extract |
| 0-15% | *Vanilla tahitensis* (Vanilla) Fruit Extract |
| 0-15% | Honey Extract |
| 0-15% | Vegetable Oil |
| 0-15% | *Gardenia tahitensis* (Tiare) Flower |
| 0-15% | *Rosmarinus officinalis* (Rosemary) Leaf Extract |

Formulation Sixty

| % Range | Ingredient |
|---|---|
| 50-100% | Water/Aqua |
| 0-15% | Decyl Glucoside |
| 0-15% | Cocamidopropyl Hydroxysultaine |
| 0-15% | Cocamidopropyl Betaine |
| 0-15% | Cocamide MIPA |
| 0-15% | Acrylates Copolymer |
| 0-15% | Disodium Laureth Sulfosuccinate |
| 0-15% | Disodium Lauryl Sulfosuccinate |
| 0-15% | Fragrance |
| 0-15% | Glycol Stearate |
| 0-15% | Butylene Glycol |
| 0-15% | Sodium Chloride |
| 0-15% | Potassium Sorbate |
| 0-15% | Sodium Hydroxide |
| 0-15% | Stearamide AMP |
| 0-15% | Disodium EDTA |
| 0-15% | *Pikea robusta* (Red Algae) Extract |
| 0-15% | Citric Acid |
| 0-15% | Panthenol |
| 0-15% | Methylchloroisothiazolinone and Methylisothiazolinone |
| 0-15% | *Macadamia integrifolia* (Macadamia) Seed Oil |
| 0-15% | *Adiantum pedatum* (Tropical Fern) Extract |
| 0-15% | *Citrus aurantifolia* (Lime) Fruit Extract |
| 0-15% | Seed Oil |
| 0-15% | *Cocos nucifera* (Coconut) Oil |
| 0-15% | Phenoxyethanol |
| 0-15% | Pantolactone |
| 0-15% | Honey Extract |
| 0-15% | *Gardenia tahitensis* (Tiare) Flower |
| 0-15% | Tocopherol |
| 0-15% | *Glycine Soja* (Soybean) Oil |
| 0-15% | *Rosmarinus officinalis* (Rosemary) Leaf Extract |

Formulation Sixty-One

| % Range | Ingredient |
|---|---|
| 50-100% | Water/Aqua |
| 0-15% | Decyl Glucoside |
| 0-15% | Cocamidopropyl Hydroxysultaine |
| 0-15% | Cocamidopropyl Betaine |
| 0-15% | Cocamide MIPA |
| 0-15% | Acrylates Copolymer |
| 0-15% | Disodium Laureth Sulfosuccinate |
| 0-15% | Disodium Lauryl Sulfosuccinate |
| 0-15% | Fragrance |
| 0-15% | Butylene Glycol |
| 0-15% | Glycol Stearate |
| 0-15% | Sodium Chloride |
| 0-15% | Potassium Sorbate |
| 0-15% | Sodium Hydroxide |
| 0-15% | Disodium EDTA |
| 0-15% | *Pikea robusta* (Red Algae) Extract |
| 0-15% | Citric Acid |
| 0-15% | Panthenol |
| 0-15% | Stearic Acid |
| 0-15% | Aminomethyl Propanol |
| 0-15% | Methylchloroisothiazolinone and Methylisothiazolinone |
| 0-15% | *Adiantum pedatum* (Maidenhair) Extract |
| 0-15% | *Citrus aurantifolia* (Lime) Fruit Extract |
| 0-15% | Seed Oil |
| 0-15% | *Cocos nucifera* (Coconut) Oil |
| 0-15% | Phenoxyethanol |
| 0-15% | *Carica papaya* (Papaya) Fruit Extract |
| 0-15% | *Vanilla tahitensis* (Vanilla) Fruit Extract |
| 0-15% | Pantolactone |
| 0-15% | Honey Extract |
| 0-15% | *Gardenia tahitensis* (Tiare) Flower |
| 0-15% | Vegetable Oil |
| 0-15% | Tocopherol |
| 0-15% | *Rosmarinus officinalis* (Rosemary) Leaf Extract |

Formulation Sixty-Two

| % Range | Ingredient |
|---|---|
| 50-100% | Water (Aqua) |
| 0-15% | Decyl Glucoside |
| 0-15% | Cocamidopropyl Hydroxysultaine |
| 0-15% | Cocamidopropyl Betaine |
| 0-15% | Cocamide MIPA |
| 0-15% | Acrylates Copolymer |
| 0-15% | Disodium Laureth Sulfosuccinate |
| 0-15% | Disodium Lauryl Sulfosuccinate |
| 0-15% | Fragrance (Parfum) |
| 0-15% | Butylene Glycol |
| 0-15% | Glycol Stearate |
| 0-15% | Sodium Chloride |
| 0-15% | Potassium Sorbate |
| 0-15% | Sodium Hydroxide |
| 0-15% | Disodium EDTA |
| 0-15% | *Pikea robusta* (Red Algae) Extract |
| 0-15% | Citric Acid |
| 0-15% | Panthenol |
| 0-15% | Stearic Acid |
| 0-15% | Aminomethyl Propanol |
| 0-15% | Methylchloroisothiazolinone and Methylisothiazolinone |
| 0-15% | *Adiantum pedatum* (Maidenhair) Extract |
| 0-15% | *Citrus aurantifolia* (Lime) Fruit Extract |
| 0-15% | Seed Oil |
| 0-15% | *Cocos nucifera* (Coconut) Oil |
| 0-15% | Phenoxyethanol |
| 0-15% | *Bougainvillea glabra* (Bougainvillea) Flower Extract |
| 0-15% | *Mangifera indica* (Mango) Fruit Extract |
| 0-15% | Pantolactone |
| 0-15% | Honey Extract |
| 0-15% | *Gardenia tahitensis* (Tiare) Flower |
| 0-15% | Vegetable Oil |
| 0-15% | Tocopherol |
| 0-15% | *Rosmarinus officinalis* (Rosemary) Leaf Extract |

Formulation Sixty-Three

| % Range | Ingredient |
|---|---|
| 50-100% | Water (Aqua) |
| 0-15% | Decyl Glucoside |
| 0-15% | Cocamidopropyl Hydroxysultaine |
| 0-15% | Cocamidopropyl Betaine |
| 0-15% | Cocamide MIPA |
| 0-15% | Acrylates Copolymer |
| 0-15% | Disodium Laureth Sulfosuccinate |
| 0-15% | Disodium Lauryl Sulfosuccinate |
| 0-15% | Fragrance |
| 0-15% | Butylene Glycol |
| 0-15% | Glycol Stearate |
| 0-15% | Sodium Chloride |
| 0-15% | Potassium Sorbate |
| 0-15% | Sodium Hydroxide |
| 0-15% | Disodium EDTA |
| 0-15% | *Pikea robusta* (Red Algae) Extract |

-continued

| % Range | Ingredient |
|---|---|
| 0-15% | Citric Acid |
| 0-15% | Panthenol |
| 0-15% | Stearic Acid |
| 0-15% | Aminomethyl Propanol |
| 0-15% | Methylchloroisothiazolinone and Methylisothiazolinone |
| 0-15% | *Adiantum pedatum* (Maidenhair) Extract |
| 0-15% | *Citrus aurantifolia* (Lime) Fruit Extract |
| 0-15% | Seed Oil |
| 0-15% | *Cocos nucifera* (Coconut) Oil |
| 0-15% | Phenoxyethanol |
| 0-15% | *Carica papaya* (Papaya) Fruit Extract |
| 0-15% | *Prunus persica* (Peach) Fruit Extract |
| 0-15% | *Vanilla tahitensis* (Vanilla) Fruit Extract |
| 0-15% | Pantolactone |
| 0-15% | Honey Extract |
| 0-15% | *Gardenia tahitensis* (Tiare) Flower |
| 0-15% | Vegetable Oil |
| 0-15% | Tocopherol |
| 0-15% | *Rosmarinus officinalis* (Rosemary) Leaf Extract |

Formulation Sixty-Four

| % Range | Ingredient |
|---|---|
| 10-75% | Water (Aqua) |
| 5-50% | *Cocos nucifera* (Coconut) Oil |
| 5-50% | *Elaeis guineensis* (Palm) Oil |
| 3-30% | Cyclomethicone |
| 3-30% | Cetearyl Alcohol |
| 3-30% | Glycerin |
| 3-30% | Glyceryl Stearate |
| 3-30% | PEG-100 Stearate |
| 0-15% | Fruit Juice |
| 0-15% | *Citris Aurantium dulcis* (Orange) Oil |
| 0-15% | Phenoxyethanol |
| 0-15% | *Glycine soja* (Soybean) Oil |
| 0-15% | PEG-150 Distearate |
| 0-15% | Chlorphenesin |
| 0-15% | Xanthan Gum |
| 0-15% | Benzoic Acid |
| 0-15% | *Cananga odorata* (Ylang Ylang) Oil |
| 0-15% | Butylene Glycol |
| 0-15% | *Aleurites moluccana* (Kukui) Seed Oil |
| 0-15% | *Mangifera indica* (Mango) Seed Oil |
| 0-15% | *Macadamia ternifolia* (Macadamia) Seed Oil |
| 0-15% | Seed Oil |
| 0-15% | Disodium EDTA |
| 0-15% | Sorbic Acid |
| 0-15% | Aminomethyl Propanol |
| 0-15% | *Jasminum officinale* (Jasmine) Oil |
| 0-15% | *Calophyllum tacamahaca* (Tamanu) Seed Oil |
| 0-15% | Riboflavin |
| 0-15% | *Gardenia tahitensis* (Tiare) Flower |
| 0-15% | Tocopherol |
| 0-15% | Vegetable Oil |
| 0-15% | *Rosmarinus officinalis* (Rosemary) Leaf Extract |

Formulation Sixty-Five

| % Range | Ingredient |
|---|---|
| 50-100% | Water/Aqua |
| 0-15% | Cetearyl Alcohol |
| 0-15% | Behentrimonium Methosulfate |
| 0-15% | Cetyl Alcohol |

-continued

| % Range | Ingredient |
|---|---|
| 0-15% | *Cocos nucifera* (Coconut) Oil |
| 0-15% | Dimethicone |
| 0-15% | Fruit Juice |
| 0-15% | Fragrance (Parfum) |
| 0-15% | *Mangifera indica* (Mango) Seed Butter |
| 0-15% | Quaternium-91 |
| 0-15% | Cinnamidopropyltrimonium Chloride |
| 0-15% | Cetrimonium Methosulfate |
| 0-15% | Hydroxyethylcellulose |
| 0-15% | Panthenol |
| 0-15% | Butylene Glycol |
| 0-15% | Phytantriol |
| 0-15% | *Pikea robusta* (Red Algae) Extract |
| 0-15% | *Gardenia tahitensis* (Tiare) Flower |
| 0-15% | Potassium Sorbate |
| 0-15% | Seed Oil |
| 0-15% | Hydrolyzed Rice Protein |
| 0-15% | Tetrasodium EDTA |
| 0-15% | Citric Acid |
| 0-15% | Sodium Acetate |
| 0-15% | Starches/Sugars in situ |
| 0-15% | DL-Lactone |
| 0-15% | Methylisothiazolinone |
| 0-15% | Sodium Chloride |
| 0-15% | Aminopropanol |
| 0-15% | Phenoxyethanol |
| 0-15% | Cellulose |
| 0-15% | *Citrus grandis* (Grapefruit) Fruit Extract |
| 0-15% | Sodium Hydroxide |
| 0-15% | Chlorphenesin |
| 0-15% | Ethanedial |
| 0-15% | Glycerin |
| 0-15% | Sorbic Acid |
| 0-15% | Vegetable Oil |
| 0-15% | Tocopherol |
| 0-15% | *Rosmarinus officinalis* (Rosemary) Leaf Extract |

Formulation Sixty-Six

| % Range | Ingredient |
|---|---|
| 50-100% | Water/Aqua |
| 3-30% | Cetearyl Alcohol |
| 0-15% | Behentrimonium Methosulfate |
| 0-15% | Cetyl Alcohol |
| 0-15% | Dimethicone |
| 0-15% | *Macadamia integrifolia* (Macadamia) Seed Oil |
| 0-15% | Fruit Juice |
| 0-15% | *Cocos nucifera* (Coconut) Oil |
| 0-15% | *Mangifera indica* (Mango) Seed Butter |
| 0-15% | Quaternium 91 |
| 0-15% | Fragrance |
| 0-15% | Cetrimonium Methosulfate |
| 0-15% | Cinnamidoproplytrimonium Chloride |
| 0-15% | Butylene Glycol |
| 0-15% | Hydroxyethylcellulose |
| 0-15% | Panthenol |
| 0-15% | Phytantriol |
| 0-15% | *Pikea robusta* (Red Algae) Extract |
| 0-15% | *Gardenia tahitensis* (Tiare) Flower |
| 0-15% | Seed Oil |
| 0-15% | Potassium Sorbate |
| 0-15% | Tetrasodium EDTA |
| 0-15% | Citric Acid |
| 0-15% | Glycerin |
| 0-15% | Hydrolyzed Rice Protein |
| 0-15% | Sodium Acetate |
| 0-15% | *Hedychium coronium* (Awapuhi) Root Extract |
| 0-15% | dl-Lactone |
| 0-15% | Methylisothiazolinone |
| 0-15% | Phenoxyethanol |
| 0-15% | Starches/Sugars in situ |

-continued

| % Range | Ingredient |
|---|---|
| 0-15% | Aminopropanol |
| 0-15% | Sodium Chloride |
| 0-15% | Cellulose |
| 0-15% | Pearl Powder |
| 0-15% | Maris Sal (Sea Salt) |
| 0-15% | *Aleurites moluccana* (Kukui) Seed Extract |
| 0-15% | *Plumeria rubra* (Plumeria) Flower Extract |
| 0-15% | *Colocasia antiquorum* (Taro) Root Extract |
| 0-15% | Sodium Hydroxide |
| 0-15% | Tocopherol |
| 0-15% | Ethanedial |
| 0-15% | Chlorphenesin |
| 0-15% | Sorbic Acid |

Formulation Sixty-Seven

| % Range | Ingredient |
|---|---|
| 50-100% | Water/Aqua |
| 3-30% | Cetearyl Alcohol |
| 0-15% | Behentrimonium Methosulfate |
| 0-15% | Cetyl Alcohol |
| 0-15% | Dimethicone |
| 0-15% | *Macadamia integrifolia* (Macadamia) Seed Oil |
| 0-15% | Fruit Juice |
| 0-15% | *Cocos nucifera* (Coconut) Oil |
| 0-15% | *Mangifera indica* (Mango) Seed Butter |
| 0-15% | Quaternium-91 |
| 0-15% | Fragrance |
| 0-15% | Cetrimonium Methosulfate |
| 0-15% | Panthenol |
| 0-15% | Butylene Glycol |
| 0-15% | Cinnamidopropyltrimonium Chloride |
| 0-15% | Hydroxyethylcellulose |
| 0-15% | *Theobroma cacao* (Cocoa) Seed Butter |
| 0-15% | Pantethine |
| 0-15% | *Pikea robusta* (Red Algae) Extract |
| 0-15% | Hydrolyzed Rice Protein |
| 0-15% | Hydrolyzed Soy Protein |
| 0-15% | Potassium Sorbate |
| 0-15% | Seed Oil |
| 0-15% | Phytantriol |
| 0-15% | Tetrasodium EDTA |
| 0-15% | Citric Acid |
| 0-15% | Sodium Chloride |
| 0-15% | Sodium Acetate |
| 0-15% | Starches/Sugars in Situ |
| 0-15% | *Ficus carica* (Fig) Fruit Extract |
| 0-15% | *Hedychium coronarium* (Awapuhi) Root Extract |
| 0-15% | *Citrus aurantifolia* (Lime) Fruit Extract |
| 0-15% | dl-Lactone |
| 0-15% | Phenoxyethanol |
| 0-15% | *Gardenia tahitensis* (Tiare) Flower |
| 0-15% | Aminopropanol |
| 0-15% | Methylisothiazolinone |
| 0-15% | Chlorphenesin |
| 0-15% | Cellulose |
| 0-15% | Glycerin |
| 0-15% | Sodium Hydroxide |
| 0-15% | Ethanedial |
| 0-15% | Tocopherol |
| 0-15% | Sorbic Acid |
| 0-15% | Vegetable Oil |
| 0-15% | *Rosmarinus officinalis* (Rosemary) Leaf Extract |

Formulation Sixty-Eight

| % Range | Ingredient |
|---|---|
| 50-100% | Water/Aqua |
| 0-15% | Decyl Glucoside |
| 0-15% | Sodium Lauroyl Sarcosinate |
| 0-15% | Cocamidopropyl Hydroxysultaine |
| 0-15% | Cocamidopropyl Betaine |
| 0-15% | Fruit Juice |
| 0-15% | Cocamide MIPA |
| 0-15% | Sodium Chloride |
| 0-15% | Disodium Laureth Sulfosuccinate |
| 0-15% | Disodium Lauryl Sulfosuccinate |
| 0-15% | Fragrance |
| 0-15% | Butylene Glycol |
| 0-15% | Hexylene Glycol |
| 0-15% | Polyquaternium 10 |
| 0-15% | Panthenol |
| 0-15% | Hydrolyzed Rice Protein |
| 0-15% | Potassium Sorbate |
| 0-15% | *Pikea robusta* (Red Algae) Extract |
| 0-15% | Citric Acid |
| 0-15% | Methylchloroisothiazolinone and Methylisothiazolinone |
| 0-15% | Tetrasodium EDTA |
| 0-15% | Starch/Sugar |
| 0-15% | *Citrus grandis* (Grapefruit) Fruit Extract |
| 0-15% | *Hedychium coronarium* (White Ginger) Root Extract |
| 0-15% | *Saponaria officinalis* (Soapwort) Extract |
| 0-15% | Phenoxyethanol |
| 0-15% | Chlorphenesin |
| 0-15% | Glycerin |
| 0-15% | Sodium Hydroxide |
| 0-15% | Sorbic Acid |

Formulation Sixty-Nine

| % Range | Ingredient |
|---|---|
| 50-100% | Water (Aqua) |
| 0-15% | Decyl Glucoside |
| 0-15% | Sodium Lauroyl Sarcosinate |
| 0-15% | Cocamidopropyl Hydroxysultaine |
| 0-15% | Cocamidopropyl Betaine |
| 0-15% | Fruit Juice |
| 0-15% | Cocamide MIPA |
| 0-15% | Sodium Chloride |
| 0-15% | Disodium Laureth Sulfosuccinate |
| 0-15% | Disodium Lauryl Sulfosuccinate |
| 0-15% | Fragrance |
| 0-15% | Glycol Distearate |
| 0-15% | Butylene Glycol |
| 0-15% | Polyquaternium-10 |
| 0-15% | Hexylene Glycol |
| 0-15% | Panthenol |
| 0-15% | Coco-Glucoside |
| 0-15% | Potassium Sorbate |
| 0-15% | Cocodimonium Hydroxypropyl Hydrolyzed Rice Protein |
| 0-15% | *Cocos nucifera* (Coconut) Oil |
| 0-15% | Glyceryl Oleate |
| 0-15% | Glyceryl Stearate |
| 0-15% | *Pikea robusta* (Red Algae) Extract |
| 0-15% | Citric Acid |
| 0-15% | Seed Oil |
| 0-15% | Glycerin |
| 0-15% | Methylchloroisothiazolinone and Methylisothiazolinone |
| 0-15% | Tetrasodium EDTA |
| 0-15% | *Hedychium coronarium* (Awapuhi) Root Extract |
| 0-15% | *Saponaria officinalis* (Soapwort) Root Extract |
| 0-15% | Benzoic Acid |

-continued

| % Range | Ingredient |
|---|---|
| 0-15% | Phenoxyethanol |
| 0-15% | Pearl Powder |
| 0-15% | Maris Sal |
| 0-15% | Sodium Hydroxide |
| 0-15% | *Aleurites moluccana* (Kukui) Seed Extract |
| 0-15% | *Plumeria rubra* (Plumeria) Flower Extract |
| 0-15% | *Colocasia antiquorum* (Taro) Root Extract |
| 0-15% | Chlorphenesin |
| 0-15% | *Gardenia tahitensis* (Tiare) Flower |
| 0-15% | Sorbic Acid |
| 0-15% | Vegetable Oil |
| 0-15% | Tocopherol |
| 10-15% | *Rosmarinus officinalis* (Rosemary) Leaf Extract |

Formulation Seventy

| % Range | Ingredient |
|---|---|
| 50-100% | Water/Aqua |
| 0-15% | Decyl Glucoside |
| 0-15% | Sodium Lauroyl Sarcosinate |
| 0-15% | Cocamidopropyl Hydroxysultaine |
| 0-15% | Cocamidopropyl Betaine |
| 0-15% | Fruit Juice |
| 0-15% | Cocamide MIPA |
| 0-15% | Sodium Chloride |
| 0-15% | Disodium Laureth Sulfosuccinate |
| 0-15% | Disodium Lauryl Sulfosuccinate |
| 0-15% | Fragrance |
| 0-15% | Butylene Glycol |
| 0-15% | Polyquaternium-10 |
| 0-15% | Panthenol |
| 0-15% | Hexylene Glycol |
| 0-15% | Potassium Sorbate |
| 0-15% | Hydrolyzed Rice Protein |
| 0-15% | Hydrolyzed Soy Protein |
| 0-15% | Pantethine |
| 0-15% | *Pikea robusta* (Red Algae) Extract |
| 0-15% | Citric Acid |
| 0-15% | Phytantriol |
| 0-15% | Methylchloroisothiazolinone and Methylisothiazolinone |
| 0-15% | Tetrasodium EDTA |
| 0-15% | Starches/Sugars in Situ |
| 0-15% | *Hedychium coronarium* (Awapuhi) Root Extract |
| 0-15% | *Ficus carica* (Fig) Fruit Extract |
| 0-15% | *Citrus aurantifolia* (Lime) Fruit Extract |
| 0-15% | Phenoxyethanol |
| 0-15% | Aminopropanol |
| 0-15% | dl-Lactone |
| 0-15% | Chlorphenesin |
| 0-15% | Glycerin |
| 0-15% | Sodium Hydroxide |
| 0-15% | Seed Oil |
| 0-15% | *Cocos nucifera* (Coconut) Oil |
| 0-15% | Sorbic Acid |
| 0-15% | *Ananas sativus* (Pineapple) Fruit Extract |
| 0-15% | *Carica papaya* (Papaya) Fruit Extract |
| 0-15% | *Gardenia tahitensis* (Tiare) Flower |
| 0-15% | Vegetable Oil |
| 0-15% | Tocopherol |
| 0-15% | *Rosmarinus officinalis* (Rosemary) Leaf Extract |

Formulation Seventy-One

| % Range | Ingredient |
|---|---|
| 35-90% | Water/Aqua |
| 3-30% | Cetearyl Alcohol |
| 3-30% | Fruit Juice |
| 0-15% | Glycerin |
| 0-15% | *Prunus amygdalus dulcis* (Sweet Almond) Oil |
| 0-15% | *Elaeis guineensis* (Palm) Oil |
| 0-15% | *Butyrospermum parkii* (Shea Butter) |
| 0-15% | *Cocos nucifera* (Coconut) Oil |
| 0-15% | Cetearyl Glucoside |
| 0-15% | Phenoxyethanol |
| 0-15% | Fragrance |
| 0-15% | Seed Oil |
| 0-15% | Tocopheryl Acetate |
| 0-15% | Xanthan Gum |
| 0-15% | Potassium Sorbate |
| 0-15% | Retinyl Palmitate |
| 0-15% | Tetrasodium EDTA |
| 0-15% | Caprylyl Glycol |
| 0-15% | *Vitis vinifera* (Grape) Seed Extract |
| 0-15% | *Gardenia tahitensis* Flower |
| 0-15% | Ascorbyl Palmitate |
| 0-15% | Sodium Hydroxide |
| 0-15% | Tocopherol |
| 0-15% | Ash |

Formulation Seventy-Two

| % Range | Ingredient |
|---|---|
| 35-90% | SD Alcohol-40 |
| 10-75% | Hydrofluorocarbon 152A |
| 5-50% | Water/Aqua |
| 3-30% | Dimethyl Ether |
| 0-15% | Acrylates Copolymer |
| 0-15% | Aminomethyl Propanol |
| 0-15% | Fragrance |
| 0-15% | Fruit Juice |
| 0-15% | Linoleamidopropyl Ethyldimonium Ethosulfate |
| 0-15% | Triethyl Citrate |
| 0-15% | AMP-Isostearoyl Hydrolyzed Wheat Protein |
| 0-15% | Cyclomethicone |
| 0-15% | PEG/PPG-17/18 Dimethicone |
| 0-15% | Glycerin |
| 0-15% | Cinnamidopropyltrimonium Chloride |
| 0-15% | *Aleurites moluccana* (Kukui) Seed Oil |
| 0-15% | Phytantriol |
| 0-15% | Seed Oil |
| 0-15% | Panthenol |
| 0-15% | *Pyrus malus* (Apple) Fruit Extract |
| 0-15% | Hydrolyzed Soy Protein |
| 0-15% | Hydrolyzed Rice Protein |
| 0-15% | Phenoxyethanol |
| 0-15% | Citric Acid |
| 0-15% | Chlorphenesin |
| 0-15% | Tocopherol |
| 0-15% | Sorbic Acid |

Formulation Seventy-Three

| % Range | Ingredient |
| --- | --- |
| 50-100% | Water/Aqua |
| 0-15% | Polyimide-1 |
| 0-15% | Phenoxyethanol |
| 0-15% | Caprylyl Glycol |
| 0-15% | Carbomer |
| 0-15% | Panthenol |
| 0-15% | Polysilicone-15 |
| 0-15% | *Carthamus tinctorius* (Safflower) Seed Oil |
| 0-15% | Aminomethyl Propanol |
| 0-15% | Potassium Sorbate |
| 0-15% | Fragrance |
| 0-15% | Disodium EDTA |
| 0-15% | *Aleurites moluccana* (Kukui) Seed Oil |
| 0-15% | Phytantriol |
| 0-15% | *Macadamia integrifolia* (Macadamia) Seed Oil |
| 0-15% | Glycerin |
| 0-15% | *Pyrus malus* (Apple) Fruit Extract |
| 0-15% | Hydrolyzed Soy Protein |
| 0-15% | Hydrolyzed Rice Protein |
| 0-15% | Seed Oil |
| 0-15% | Citric Acid |
| 0-15% | Chlorphenesin |
| 0-15% | Sorbic Acid |
| 0-15% | Tocopherol |
| 0-15% | Vegetable Oil |
| 0-15% | *Rosmarinus officinalis* (Rosemary) Leaf Extract |

Formulation Seventy-Four

| % Range | Ingredient |
| --- | --- |
| 5-50% | Milk Protein Isolate |
| 5-50% | Inulin (Contains Fructooligosaccharides) |
| 5-50% | Soy Protein Isolate |
| 3-30% | Dutch Cocoa |
| 3-30% | Citrus Fiber (From Peel & Pulp) |
| 3-30% | Oat Fiber (From Seed) |
| 3-30% | Whey Protein Isolate |
| 3-30% | High Oleic Sunflower Oil |
| 0-15% | Gum Acacia (From Sap) |
| 0-15% | Corn Syrup Solids |
| 0-15% | Soybean Fiber |
| 0-15% | Natural and Artificial Flavors |
| 0-15% | Cellulose Gum |
| 0-15% | Guar Gum |
| 0-15% | Egg Albumin |
| 0-15% | Malto-Dextrin |
| 0-15% | Sodium Caseinate (A Milk Derivative) |
| 0-15% | Salt |
| 0-15% | Mono-and Diglycerides |
| 0-15% | Carrageenan |
| 0-15% | Dipotassium Phosphate |
| 0-15% | Silicon Dioxide |
| 0-15% | Soy Lecithin |
| 0-15% | Potassium Chloride |
| 0-15% | Sucralose (Sweetener) |
| 0-15% | Vitamin C (as Ascorbic Acid and Ascorbyl Palmitate) |
| 0-15% | Fruit Fiber |
| 0-15% | Vitamin E (as dl-alpha Tocopheryl Acetate and Mixed Tocopherols) |
| 0-15% | Dicalcium Phosphate |
| 0-15% | Magnesium Oxide |
| 0-15% | Vitamin A (as Vitamin A Palmitate and Beta-Carotene) |
| 0-15% | Niacin (as Niacinamide) |
| 0-15% | Zinc (as Zinc Oxide) |
| 0-15% | Iron (as Iron Electrolytic) |
| 0-15% | Copper (as Copper Gluconate) |
| 0-15% | Pantothenic Acid (as d-Calcium Pantothenate) |
| 0-15% | Vitamin D (as Cholecalciferol) |
| 0-15% | Hydrogenated Soybean Oil |
| 0-15% | Vitamin B6 (as Pyridoxine Hydrochloride) |
| 0-15% | Sucrose |
| 0-15% | Riboflavin (Vitamin B2) |
| 0-15% | Thiamin (as Thiamine Mononitrate) |
| 0-15% | Vitamin B12 (as Cyanocobalamin) |
| 0-15% | Folic Acid |
| 0-15% | Biotin |
| 0-15% | Iodine (as Potassium Iodide) |
| 0-15% | Sodium Ascorbate |

Formulation Seventy-Five

| % Range | Ingredient |
| --- | --- |
| 5-50% | Milk Protein Isolate |
| 5-50% | Inulin (Contains Fructooligosaccharides) |
| 5-50% | Soy Protein Isolate |
| 3-30% | Oat Fiber (From Seed) |
| 3-30% | Citrus Fiber (From Peel & Pulp) |
| 3-30% | Whey Protein Isolate |
| 3-30% | High Oleic Sunflower Oil |
| 3-30% | Gum Arabic (From Sap) |
| 0-15% | Corn Syrup Solids |
| 0-15% | Soybean Fiber |
| 0-15% | Natural and Artificial Flavors |
| 0-15% | Cellulose Gum |
| 0-15% | Guar Gum |
| 0-15% | Egg Albumin |
| 0-15% | Malto-Dextrin |
| 0-15% | Sodium Caseinate (A Milk Derivative) |
| 0-15% | Salt |
| 0-15% | Mono- and Diglycerides |
| 0-15% | Dipotassium Phosphate |
| 0-15% | Carrageenan |
| 0-15% | Silicon Dioxide |
| 0-15% | Soy Lecithin |
| 0-15% | Potassium Chloride |
| 0-15% | Vitamin C (as Ascorbic Acid, Ascorbyl Palmitate, and Sodium Ascorbate) |
| 0-15% | Fruit Fiber |
| 0-15% | Vitamin E (as dl-alpha Tocopheryl Acetate and Mixed Tocopherols) |
| 0-15% | Dicalcium Phosphate |
| 0-15% | Sucralose (a Sweetener) |
| 0-15% | Magnesium Oxide |
| 0-15% | Vitamin A (as Vitamin A Palmitate and Beta-Carotene) |
| 0-15% | Niacin (as Niacinamide) |
| 0-15% | Zinc (as Zinc Oxide) |
| 0-15% | Iron (as Iron Electrolytic) |
| 0-15% | Copper (as Copper Gluconate) |
| 0-15% | Dextrin |
| 0-15% | Pantothenic Acid (as d-Calcium Pantothenate) |
| 0-15% | Vitamin D (as Cholecalciferol) |
| 0-15% | Vegetable Oil |
| 0-15% | Vitamin B6 (as Pyridoxine Hydrochloride) |
| 0-15% | Sucrose |
| 0-15% | Riboflavin (Vitamin B2) |
| 0-15% | Thiamin (as Thiamine Mononitrate) |
| 0-15% | Vitamin B12 (as Cyanocobalamin) |
| 0-15% | Folic Acid |
| 0-15% | Biotin |
| 0-15% | Iodine (as Potassium Iodide) |

Formulation Seventy-Six

| % Range | Ingredient |
|---|---|
| 35-90% | *Garcinia Cambogia* Fruit Extract |
| 3-30% | Gelatin |
| 3-30% | L-Carnitine |
| 0-15% | Maltodextrin |
| 0-15% | Chromium Chelate |
| 0-15% | Magnesium Stearate |
| 0-15% | Silicon Dioxide |
| 0-15% | Fruit Fiber |

Formulation Seventy-Seven

| % Range | Ingredient |
|---|---|
| 50-00% | Water (Aqua) |
| 3-30% | Fruit Juice |
| 0-15% | *Carthamus tinctorius* (Safflower) Seed Oil |
| 0-15% | Cetyl Alcohol |
| 0-15% | Glycerin |
| 0-15% | Glyceryl Stearate |
| 0-15% | Progesterone |
| 0-15% | Ethoxydiglycol |
| 0-15% | Stearic Acid |
| 0-15% | *Helianthus annuus* (Sunflower) Seed Oil |
| 0-15% | Sodium Stearoyl Lactylate |
| 0-15% | Phenoxyethanol |
| 0-15% | Caprylyl Glycol |
| 0-15% | Triethanolamine |
| 0-15% | Carbomer |
| 0-15% | Polysorbate 20 |
| 0-15% | Hydrogenated Lecithin |
| 0-15% | Seed Oil |
| 0-15% | Tocopheryl Acetate |
| 0-15% | Disodium EDTA |
| 0-15% | Sorbic Acid |
| 0-15% | Tocopherol |

Formulation Seventy-Eight

| % Range | Ingredient |
|---|---|
| 35-90% | Calcium Carbonate |
| 5-50% | Magnesium Oxide |
| 5-50% | Microcrystalline Cellulose |
| 0-15% | Maltodextrin |
| 0-15% | Calcium Citrate |
| 0-15% | Croscarmellose Sodium |
| 0-15% | Fruit Fiber |
| 0-15% | Water |
| 0-15% | HPMC, Maltodextrin, Fractionated Coconut Oil |
| 0-15% | Magnesium Stearate |
| 0-15% | Silicon Dioxide |
| 0-15% | Vitamin D (as Cholecalciferol) |

Formulation Seventy-Nine

| % Range | Ingredient |
|---|---|
| 50-100% | Water |
| 0-15% | TNJ Concentrate |
| 0-15% | Iti White Guava Puree #3100 |
| 0-15% | Encore Orange Juice Concentrate |
| 0-15% | Milne Cranberry Juice Conc. Essence Ret. 50 Brix |
| 0-15% | NW Naturals Pineapple Ju. Conc #19666 |
| 0-15% | Milne Concord Grape Ju. Conc. 68 Brix Essnce Ret. |
| 0-15% | Tree Top Apple Juice Conc. TTA01 |
| 0-15% | Tree Top Pear Juice Conc. TTP01 |
| 0-15% | Roche Vitamin Premix # XR13338000 no biotin/Vit E Beta Carotene (Vitamin A) Ascorbic Acid (Vitamin C) Cholecalciferol (Vitamin D3) Thiamine Mononitrate (Vitamin B1) Riboflavin (Vitamin B2) Niacinamide (Vitamin B3) Pyridoxine Hydrochloride (Vitamin B6) Folic Acid (Vitamin B9) Cyanocobalamin (Vitamin B12) Calcium Pantothenate (Vitamin B5) Maltodextrin (Carrier) |

Formulation Eighty

| % Range | Ingredient |
|---|---|
| 35-90% | Fish Oil (300/200 EPH/DHA |
| 5-50% | Seed Oil |
| 5-50% | Flax Seed Oil |
| 0-15% | Borage Oil |
| 0-15% | Vitamin E (d-Alpha Tocopheryl Acetate) |
| 0-15% | Evening Primrose Oil |
| 0-15% | Black Currant Seed Oil |

Formulation Eighty-One

| % Range | Ingredient |
|---|---|
| 35-90% | Soy Protein Concentrate |
| 10-75% | Soy Protein Isolate |
| 3-30% | Dutch Cocoa |
| 0-15% | Calcium Carbonate |
| 0-15% | High Oleic Sunflower Oil |
| 0-15% | Calcium Phosphate |
| 0-15% | Corn Syrup Solids |
| 0-15% | Maltodextrin |
| 0-15% | Salt |
| 0-15% | Natural and Artificial Flavors |
| 0-15% | Soy Lecithin |
| 0-15% | Sodium Caseinate |
| 0-15% | Sucralose |
| 0-15% | Mono and Diglycerides |
| 0-15% | Dipotassium Phosphate |
| 0-15% | Tricalcium Phosphate |
| 0-15% | Malic Acid |
| 0-15% | Fruit Fiber |
| 0-15% | Mixed Tocopherols |

Formulation Eighty-Two

| % Range | Ingredient |
| --- | --- |
| 35-90% | Soy Protein Concentrate |
| 10-75% | Soy Protein Isolate |
| 0-15% | Calcium Carbonate |
| 0-15% | High Oleic Sunflower Oil |
| 0-15% | Corn Syrup Solids |
| 0-15% | Maltodextrin |
| 0-15% | Salt |
| 0-15% | Natural and Artificial Flavors |
| 0-15% | Soy Lecithin |
| 0-15% | Sodium Caseinate |
| 0-15% | Sucralose |
| 0-15% | Mono and Diglycerides |
| 0-15% | Dipotassium Phosphate |
| 0-15% | Tricalcium Phosphate |
| 0-15% | Silicon dioxide |
| 0-15% | Malic Acid |
| 0-15% | Vitamin A (from beta-carotene |
| 0-15% | Fruit Fiber |
| 0-15% | Mixed Tocopherols |

Formulation Eighty-Three

| % Range | Ingredient |
| --- | --- |
| 10-75% | Soy Protein Concentrate |
| 10-75% | Soy Protein Isolate |
| 0-15% | Calcium Carbonate |
| 0-15% | High Oleic Sunflower Oil |
| 0-15% | Calcium Phosphate |
| 0-15% | Corn Syrup Solids |
| 0-15% | Maltodextrin |
| 0-15% | Natural Flavors |
| 0-15% | Soy Lecithin |
| 0-15% | Salt |
| 0-15% | Sodium Caseinate |
| 0-15% | Mono and Diglycerides |
| 0-15% | Dipotassium Phosphate |
| 0-15% | Tricalcium Phosphate |
| 0-15% | Sucralose |
| 0-15% | Malic Acid |
| 0-15% | Fruit Fiber |
| 0-15% | Mixed Tocopherols |

Formulation Eighty-Four

| % Range | Ingredient |
| --- | --- |
| 10-75% | Maltodextrin (tableting excipient) |
| 5-50% | Microcrystalline cellulose (tableting excipient) |
| 5-50% | Vitamin E (as d-alpha-tocopherol Acid Succinate) |
| 3-30% | Vegetable oil and Cellulose (coating excipient) |
| 3-30% | Ascorbic Acid |
| 0-15% | Coral Calcium |
| 0-15% | Croscarmellose sodium (tableting excipient) |
| 0-15% | Dicalcium Phosphate (carrier) |
| 0-15% | Red clover Extract (*Trifolium pratense*) |
| 0-15% | Pyridoxine Hydrochloride |
| 0-15% | Silicon Dioxide (excipient) |
| 0-15% | Chasteberry Extract (*Vitex agnus-catus*) |
| 0-15% | Inositol |
| 0-15% | P-Amino Benzoic Acid (PABA) |
| 0-15% | Choline Bitartrate |
| 0-15% | Magenesium oxide |
| 0-15% | Black Cohosh Dry Extract (*Cimicifuga racemosa*) |
| 0-15% | Selenium Yeast |
| 0-15% | Calcium D-pantothenate |
| 0-15% | Stearic Acid (tableting excipient) |
| 0-15% | Ferric Fumarate |
| 0-15% | Calendula Flower Extract (*Calendula officinalis*) |
| 0-15% | Coating agent (dextrin, dextrose, lecithin, SCMC, sodium citrate) |
| 0-15% | Boron Amino Acid Chelate |
| 0-15% | Zinc oxide |
| 0-15% | Magnesium Stearate |
| 0-15% | Copper gluconate |
| 0-15% | Manganese Amino Acid Chelate |
| 0-15% | Beta carotene |
| 0-15% | Niacinamide |
| 0-15% | Niacin |
| 0-15% | Vanadium Amino Acid Chelate |
| 0-15% | Coating agent (Methylcellulose and glycerin) |
| 0-15% | Retinyl palmitate |
| 0-15% | Cholecalciferol |
| 0-15% | Fruit pulp |
| 0-15% | Chromium Amino Acid Chelate |
| 0-15% | Molybdenum Amino Acid Chelate |
| 0-15% | Thiamine Mononitrate |
| 0-15% | Riboflavin |
| 0-15% | Cyanocobalamin |
| 0-15% | Folic Acid |
| 0-15% | Biotin |
| 0-15% | Potassium Iodide |

Formulation Eighty-Five

| % Range | Ingredient |
| --- | --- |
| 10-75% | *Ricinus communis* (Castor) Seed Oil |
| 5-50% | Ozokerite |
| 5-50% | Hydrogenated Castor Oil |
| 3-30% | Ethylhexyl Methoxycinnamate **Octinoxate |
| 3-30% | *Euphorbia cerifera* (Candelilla) Wax |
| 3-30% | Sorbitan Oleate |
| 0-15% | Benzophenone-3 **Oxybenzone |
| 0-15% | Flavor |
| 0-15% | *Butyrospermum parkii* (Shea Butter) |
| 0-15% | Seed Oil |
| 0-15% | *Aleurites moluccana* (Kukui) Seed Oil |
| 0-15% | *Macadamia ternifolia* (Macadamia) Seed Oil |
| 0-15% | Sodium Saccharin |
| 0-15% | Phenoxyethanol |
| 0-15% | *Prunus amygdalus dulcis* (Sweet Almond) Oil |
| 0-15% | Menthol |
| 0-15% | Camphor |
| 0-15% | Tocopheryl Acetate |
| 0-15% | Tocopherol |
| 0-15% | Vegetable Oil |
| 0-15% | *Rosmarinus officinalis* (Rosemary) Leaf Extract |

Formulation Eighty-Six

| % Range | Ingredient |
| --- | --- |
| 50-100% | *Ricinus communis* (Castor) Seed Oil |
| 5-50% | Ozokerite |
| 5-50% | Hydrogenated Castor Oil |
| 3-30% | Ethylhexyl Methoxycinnamate **Octinoxate |
| 3-30% | *Euphorbia cerifera* (Candelilla) Wax |

Formulation Eighty-Seven

| % Range | Ingredient |
|---|---|
| 3-30% | Sorbitan Oleate |
| 0-15% | Benzophenone-3 **Oxybenzone |
| 0-15% | Flavor |
| 0-15% | *Butyrospermum parkii* (Shea Butter) |
| 0-15% | Seed Oil |
| 0-15% | *Aleurites moluccana* (Kukui) Seed Oil |
| 0-15% | *Macadamia ternifolia* (Macadamia) Seed Oil |
| 0-15% | Sodium Saccharin |
| 0-15% | Phenoxyethanol |
| 0-15% | *Prunus amygdalus dulcis* (Sweet Almond) Oil |
| 0-15% | Menthol |
| 0-15% | Camphor |
| 0-15% | Tocopheryl Acetate |
| 0-15% | Tocopherol |
| 0-15% | Vegetable Oil |
| 0-15% | *Rosmarinus officinalis* (Rosemary) Leaf Extract |

Formulation Eighty-Eight

| % Range | Ingredient |
|---|---|
| 10-75% | *Ricinus communis* (Castor) Seed Oil |
| 5-50% | Ozokerite |
| 5-50% | Hydrogenated Castor Oil |
| 3-30% | Ethylhexyl Methoxycinnamate **Octinoxate |
| 3-30% | *Euphorbia cerifera* (Candelilla) Wax |
| 3-30% | Sorbitan Oleate |
| 0-15% | Benzophenone-3 **Oxybenzone |
| 0-15% | Flavor |
| 0-15% | *Butyrospermum parkii* (Shea Butter) |
| 0-15% | Seed Oil |
| 0-15% | *Aleurites moluccana* (Kukui) Seed Oil |
| 0-15% | *Macadamia ternifolia* (Macadamia) Seed Oil |
| 0-15% | Sodium Saccharin |
| 0-15% | Phenoxyethanol |
| 0-15% | *Prunus amygdalus dulcis* (Sweet Almond) Oil |
| 0-15% | Menthol |
| 0-15% | Camphor |
| 0-15% | Tocopheryl Acetate |
| 0-15% | Tocopherol |
| 0-15% | Vegetable Oil |
| 0-15% | *Rosmarinus officinalis* (Rosemary) Leaf Extract |

| % Range | Ingredient |
|---|---|
| 50-100% | Water (Aqua) |
| 3-30% | Fruit Juice |
| 0-15% | *Carthamus tinctorius* (Safflower) Seed Oil |
| 0-15% | Cetyl Alcohol |
| 0-15% | Glycerin |
| 0-15% | Glyceryl Stearate |
| 0-15% | Progesterone |
| 0-15% | Ethoxydiglycol |
| 0-15% | Stearic Acid |
| 0-15% | *Helianthus annuus* (Sunflower) Seed Oil |
| 0-15% | Sodium Stearoyl Lactylate |
| 0-15% | Phenoxyethanol |
| 0-15% | Caprylyl Glycol |
| 0-15% | Carbomer |
| 0-15% | Polysorbate 20 |
| 0-15% | Hydrogenated Lecithin |
| 0-15% | Triethanolamine |
| 0-15% | Seed Oil |
| 0-15% | Tocopheryl Acetate |
| 0-15% | Disodium EDTA |
| 0-15% | Sorbic Acid |
| 0-15% | Diethanolamine |
| 0-15% | Vegetable Oil |
| 0-15% | Tocopherol |
| 0-15% | *Rosmarinus officinalis* (Rosemary) Leaf Extract |

Formulation Eight-Nine

| % Range | Ingredient |
|---|---|
| 10-75% | Sodium Cocoate |
| 10-75% | Glycerin |
| 5-50% | Deionized Water |
| 5-50% | Sodium Castorate |
| 3-30% | Sodium Safflowerate |
| 3-30% | Sorbitol |
| 3-30% | *Avena sativa* (Oat) Kernel Flour |
| 0-15% | Fragrance |
| 0-15% | Fruit Juice |
| 0-15% | *Aloe barbadensis* (Aloe) Leaf Juice |

Formulation Ninety

| % Range | Ingredient |
|---|---|
| 10-75% | Sodium Cocoate |
| 10-75% | Aqua (Water) |
| 10-75% | Glycerin |
| 5-50% | Sodium Castorate |
| 3-30% | Sodium Safflowerate |
| 0-15% | Sorbitol |
| 0-15% | Fragrance |
| 0-15% | Puree |
| 0-15% | *Aloe barbadensis* (Aloe) Leaf Juice |
| 0-15% | *Cocos nucifera* (Coconut) Extract |
| 0-15% | *Cyamopsis tetragonoloba* (Guar) Gum |
| 0-15% | Methyl Paraben |
| 0-15% | Sodium Benzoate |
| 0-15% | Potassium Sorbate |
| 0-15% | Sodium Metabisulfate |
| 0-15% | Titanium Dioxide |
| 0-15% | Aluminum Hydroxide |
| 0-15% | Silica |

Formulation Ninety-One

| % Range | Ingredient |
|---|---|
| 10-75% | Sodium Cocoate |
| 10-75% | Water (Aqua) |
| 10-75% | Glycerin |
| 5-50% | Sodium Castorate |
| 3-30% | Sodium Safflowerate |
| 0-15% | Sorbitol |
| 0-15% | Fragrance (Parfum) |
| 0-15% | Fruit Puree |
| 0-15% | *Aloe barbadensis* (Aloe) Leaf Juice |
| 0-15% | *Carica papaya* (Papaya) Fruit Extract |
| 0-15% | Propylene Glycol |

-continued

| % Range | Ingredient |
|---|---|
| 0-15% | Methylparaben |
| 0-15% | Sodium Benzoate |
| 0-15% | Potassium Sorbate |
| 0-15% | Sodium Metabisulfite |
| 0-15% | Titanium Dioxide |
| 0-15% | *Helianthus annuus* (Sunflower) Seed Oil |
| 0-15% | Lecithin |
| 0-15% | Beta-Carotene |
| 0-15% | Hydrogenated Vegetable Glycerides Citrate |
| 0-15% | Ascorbic Acid |
| 0-15% | Ascorbyl Palmitate |
| 0-15% | Tocopherol |
| 0-15% | Aluminum Hydroxide |
| 0-15% | Hydrated Silica |

Formulation Ninety-Two

| % Range | Ingredient |
|---|---|
| 10-75% | Sodium Cocoate |
| 10-75% | Water (Aqua) |
| 10-75% | Glycerin |
| 5-50% | Sodium Castorate |
| 3-30% | Sodium Safflowerate |
| 0-15% | Sorbitol |
| 0-15% | Fragrance (Parfum) |
| 0-15% | Fruit Puree |
| 0-15% | *Aloe barbadensis* (Aloe) Leaf Juice |
| 0-15% | *Laminaria digitata* (Seaweed) Extract |
| 0-15% | Propylene Glycol |
| 0-15% | Methylparaben |
| 0-15% | Sodium Benzoate |
| 0-15% | Potassium Sorbate |
| 0-15% | Sodium Metabisulfite |
| 0-15% | Titanium Dioxide |
| 0-15% | Chlorophyllin-Copper Complex |
| 0-15% | Aluminum Hydroxide |
| 0-15% | Hydrated Silica |

Formulation Ninety-Three

| % Range | Ingredient |
|---|---|
| 10-75% | Sodium Cocoate |
| 10-75% | Water (Aqua) |
| 10-75% | Glycerin |
| 5-50% | Sodium Castorate |
| 3-30% | Sodium Safflowerate |
| 0-15% | Sorbitol |
| 0-15% | Fragrance (Parfum) |
| 0-15% | Fruit Puree |
| 0-15% | *Aloe barbadensis* (Aloe) Leaf Juice |
| 0-15% | *Laminaria digitata* (Seaweed) Extract |
| 0-15% | Propylene Glycol |
| 0-15% | Methylparaben |
| 0-15% | Sodium Benzoate |
| 0-15% | Potassium Sorbate |
| 0-15% | Sodium Metabisulfite |
| 0-15% | Titanium Dioxide |
| 0-15% | Chlorophyllin-Copper Complex |
| 0-15% | Aluminum Hydroxide |
| 0-15% | Hydrated Silica |

Formulation Ninety-Four

| % Range | Ingredient |
|---|---|
| 35-90% | Water/Aqua |
| 3-30% | *Octinoxate (Ethylhexylmethoxycinnamate) |
| 3-30% | *Homosalate |
| 3-30% | *Octisalate (Ethylhexyl Salicylate) |
| 0-15% | Fruit Juice |
| 0-15% | Glyceryl Stearate SE |
| 0-15% | *Oxybenzone (Benzophenone-3) |
| 0-15% | C12-15 Alkyl Benzoate |
| 0-15% | Glycerin |
| 0-15% | *Avobenzone (Butylmethoxydibenzoylmethane) |
| 0-15% | Cetearyl Alcohol |
| 0-15% | Dimethicone |
| 0-15% | Ceteareth-20 |
| 0-15% | Phenoxyethanol |
| 0-15% | Caprylyl Glycol |
| 0-15% | *Prunus amygdalus dulcis* (Sweet Almond) Oil |
| 0-15% | *Butyrospennum parkii* (Shea Butter) |
| 0-15% | *Elaeis guineensis* (Palm) Oil |
| 0-15% | Tocopheryl Acetate |
| 0-15% | Seed Oil |
| 0-15% | Carbomer |
| 0-15% | Fragrance |
| 0-15% | *Cocos nucifera* (Coconut) Oil |
| 0-15% | Potassium Sorbate |
| 0-15% | Ascorbyl Palmitate |
| 0-15% | Disodium EDTA |
| 0-15% | Sodium Hydroxide |
| 0-15% | Retinyl Palmitate |
| 0-15% | *Vitis vinifera* (Grape) Seed Extract |
| 0-15% | Tocopherol |
| 0-15% | *Gardenia tahitensis* (Tiare) Flower |

Formulation Ninety-Five

| % Range | Ingredient |
|---|---|
| 50-100% | Water/Aqua |
| 0-15% | Fruit Juice |
| 0-15% | Polysorbate 20 |
| 0-15% | Glycerin |
| 0-15% | Phenoxyethanol |
| 0-15% | Caprylyl Glycol |
| 0-15% | Panthenol |
| 0-15% | Ethoxydiglycol |
| 0-15% | *Pikea robusta* (Red Algae) Extract |
| 0-15% | Potassium Sorbate |
| 0-15% | Fragrance |
| 0-15% | Disodium EDTA |
| 0-15% | Butylene Glycol |
| 0-15% | *Macrocystis pyrifera* (Sea Kelp) Extract |
| 0-15% | *Avena sativa* (Oat) Kernel Extract |
| 0-15% | Leaf Extract |
| 0-15% | Citric Acid |
| 0-15% | Sodium Hyaluronate |
| 0-15% | Ascorbic Acid |
| 0-15% | Tocopheryl Acetate |
| 0-15% | Retinyl Palmitate |
| 0-15% | Tocopherol |

Formulation Ninety-Six

| % Range | Ingredient |
| --- | --- |
| 50-100% | Water/Aqua |
| 0-15% | Fruit Juice |
| 0-15% | Polysorbate 20 |
| 0-15% | Glycerin |
| 0-15% | Phenoxyethanol |
| 0-15% | Caprylyl Glycol |
| 0-15% | Panthenol |
| 0-15% | Ethoxydiglycol |
| 0-15% | *Pikea robusta* (Red Algae) Extract |
| 0-15% | Potassium Sorbate |
| 0-15% | Fragrance |
| 0-15% | Disodium EDTA |
| 0-15% | Butylene Glycol |
| 0-15% | *Macrocystis pyrifera* (Sea Kelp) Extract |
| 0-15% | *Avena sativa* (Oat) Kernel Extract |
| 0-15% | Leaf Extract |
| 0-15% | Citric Acid |
| 0-15% | Sodium Hyaluronate |
| 0-15% | Ascorbic Acid |
| 0-15% | Tocopheryl Acetate |
| 0-15% | Retinyl Palmitate |
| 0-15% | Tocopherol |

Formulation Ninety-Seven

| % Range | Ingredient |
| --- | --- |
| 50-100% | Water/Aqua |
| 3-30% | Decyl Glucoside |
| 0-15% | Cocamidopropyl Hydroxysultaine |
| 0-15% | Cocamidopropyl Betaine |
| 0-15% | Cocamide MIPA |
| 0-15% | Fruit Juice |
| 0-15% | Disodium Laureth Sulfosuccinate |
| 0-15% | Disodium Lauryl Sulfosuccinate |
| 0-15% | Sodium Chloride |
| 0-15% | Fragrance |
| 0-15% | Butylene Glycol |
| 0-15% | Hexylene Glycol |
| 0-15% | Potassium Sorbate |
| 0-15% | Disodium EDTA |
| 0-15% | *Pikea robusta* (Red Algae) Extract |
| 0-15% | Panthenol |
| 0-15% | Methylchloroisothiazolinone and Methylisothiazolinone |
| 0-15% | Citric Acid |
| 0-15% | *Adiantum pedatum* (Maidenhair) Extract |
| 0-15% | *Citrus aurantifolia* (Lime) Fruit Extract. |
| 0-15% | Phenoxyethanol |
| 0-15% | Honey Extract |
| 0-15% | Tocopheryl Acetate |
| 0-15% | Ascorbic Acid |
| 0-15% | Retinyl Palmitate |
| 0-15% | Tocopherol |

Formulation Ninety-Eight

| % Range | Ingredient |
| --- | --- |
| 50-100% | Water/Aqua |
| 0-15% | Fruit Juice |
| 0-15% | Polyacrylate |
| 0-15% | Salicylic Acid |
| 0-15% | Allyl Methacrylates crosspolymer |
| 0-15% | Phenoxyethanol |
| 0-15% | Polyisobutene |
| 0-15% | Caprylyl Glycol |
| 0-15% | *Salix nigra* (Willow) Bark Extract |
| 0-15% | Modified *Amorphophallus Konjac* (Konjac) Root Extract |
| 0-15% | Polysorbate 20 |
| 0-15% | Potassium Sorbate |
| 0-15% | Xanthan Gum |
| 0-15% | Ethoxydiglycol |
| 0-15% | Zinc PCA |
| 0-15% | Bisabolol |
| 0-15% | Leaf Juice |
| 0-15% | Disodium EDTA |
| 0-15% | Glycerin |
| 0-15% | *Curcuma longa* (Tumeric) Root Extract |
| 0-15% | Leaf Extract |

Formulation Ninety-Nine

| % Range | Ingredient |
| --- | --- |
| 50-100% | Water (Aqua) |
| 3-30% | Sodium Cocoyl Glutamate |
| 3-30% | Disodium Cocoyl Glutamate |
| 0-15% | Glycerin |
| 0-15% | Fruit Juice |
| 0-15% | *Chondrus crispus* (Carrageenan) |
| 0-15% | Phenoxyethanol |
| 0-15% | Caprylyl Glycol |
| 0-15% | Citric Acid |
| 0-15% | *Pikea robusta* (Red Algae) Extract |
| 0-15% | Butylene Glycol |
| 0-15% | Potassium Sorbate |
| 0-15% | *Salix nigra* (Willow) Bark Extract |
| 0-15% | Disodium EDTA |
| 0-15% | *Amorphophallus konjac* (Konjac) Root Powder |
| 0-15% | Fragrance (Parfum) |
| 0-15% | Glucose |
| 0-15% | *Ocimum basilicum* (Basil) Leaf Extract |
| 0-15% | *Citrus grandis* (Grapefruit) Fruit Extract |
| 0-15% | *Moringa pterygosperma* (Moringa) Seed Extract |
| 0-15% | *Macrocystis pyrifera* (Kelp) Extract |

Formulation One Hundred

| % Range | Ingredient |
| --- | --- |
| 50-100% | *Helianthus annuus* (Sunflower) Seed Oil |
| 3-30% | *Aleurites moluccana* (Kukui) Seed Oil |
| 3-30% | *Macadamia integrifolia* (Macadamia) Seed Oil |
| 0-15% | Laureth-4 |
| 0-15% | *Cocos nucifera* (Coconut) Oil |
| 0-15% | Phenoxyethanol |
| 0-15% | Seed Oil |
| 0-15% | Fragrance (Parfum) |
| 0-15% | *Calophyllum inophyllum* (Tamanu) Seed Oil |
| 0-15% | *Moringa oleifera* Seed Oil |
| 0-15% | Tocopherol |
| 0-15% | *Laminaria digitata* (Algae) Extract |
| 0-15% | *Macrocystis pyrifera* (Kelp) Extract |
| 0-15% | *Gardenia tahitensis* (Tiare) Flower |
| 0-15% | Fruit Juice Concentrate |

Formulation One Hundred One

| % Range | Ingredient |
| --- | --- |
| 0-15% | Vegetable Oil |
| 0-15% | *Rosmarinus officinalis* (Rosemary) Leaf Extract |

Formulation One Hundred One

| % Range | Ingredient |
| --- | --- |
| 35-90% | Water/Aqua |
| 5-50% | *Aleurites moluccana* (Kukui) Seed Oil |
| 3-30% | *Macadamia integrifolia* (Macadamia) Seed Oil |
| 3-30% | Cetearyl Alcohol |
| 0-15% | *Cocos nucifera* (Coconut) Oil |
| 0-15% | Fruit Juice |
| 0-15% | Dimethicone |
| 0-15% | Cetearyl Glucoside |
| 0-15% | Glyceryl Stearate |
| 0-15% | PEG-100 Stearate |
| 0-15% | Glycerin |
| 0-15% | Seed Oil |
| 0-15% | *Glycine soja* (Soybean) Seed Extract |
| 0-15% | Phenoxyethanol |
| 0-15% | Caprylyl Glycol |
| 0-15% | *Glycine soja* (Soybean) Sterol |
| 0-15% | Xanthan Gum |
| 0-15% | Panthenol |
| 0-15% | Bisabolol |
| 0-15% | Ethoxydiglycol |
| 0-15% | *Pikea robusta* (Red Algae) Extract |
| 0-15% | Potassium Sorbate |
| 0-15% | Disodium EDTA |
| 0-15% | Butylene Glycol |
| 0-15% | *Gardenia tahitensis* (Tiare) Flower |
| 0-15% | *Macrocystis pyrifera* (Kelp) Extract |
| 0-15% | Ceramide NP |
| 0-15% | Leaf Extract |
| 0-15% | *Avena sativa* (Oat) Kernel Extract |
| 0-15% | Beta-Glucan |
| 0-15% | Pantolactone |
| 0-15% | Tocopherol |
| 0-15% | Sodium Hyaluronate |
| 0-15% | 1,2-Hexanediol |
| 0-15% | Citric Acid |
| 0-15% | Benzoic Acid |
| 0-15% | Sodium Benzoate |
| 0-15% | Vegetable Oil |
| 0-15% | *Rosmarinus officinalis* (Rosemary) Leaf Extract |

Formulation One Hundred Two

| % Range | Ingredient |
| --- | --- |
| 50-100% | Water (Aqua) |
| 3-30% | *Aleurites moluccana* (Kukui) Seed Oil |
| 0-15% | Cetearyl Alcohol |
| 0-15% | *Macadamia integrifolia* (Macadamia) Seed Oil |
| 0-15% | Fruit Juice |
| 0-15% | Dimethicone |
| 0-15% | Cetearyl Glucoside |
| 0-15% | Glyceryl Stearate |
| 0-15% | PEG-100 Stearate |
| 0-15% | Seed Oil |
| 0-15% | *Cocos nucifera* (Coconut) Oil |
| 0-15% | *Glycine soja* (Soybean) Seed Extract |
| 0-15% | Phenoxyethanol |
| 0-15% | Glycerin |
| 0-15% | *Glycine soja* (Soybean) Sterols |
| 0-15% | Leaf Juice |
| 0-15% | Xanthan Gum |
| 0-15% | Bisabolol |
| 0-15% | Ethoxydiglycol |
| 0-15% | Potassium Sorbate |
| 0-15% | Butylene Glycol |
| 0-15% | *Pikea robusta* (Red Algae) Extract |
| 0-15% | Fragrance (Parfum) |
| 0-15% | Panthenol |
| 0-15% | *Calophyllum inophyllum* (Tamanu) Seed Oil |
| 0-15% | Ethylhexylglycerin |
| 0-15% | Disodium EDTA |
| 0-15% | *Macrocystis pyrifera* (Kelp) Extract |
| 0-15% | *Avena sativa* (Oat) Kernel Extract |
| 0-15% | Ceramide NP |
| 0-15% | Leaf Extract |
| 0-15% | *Gardenia tahitensis* (Tiare) Flower |
| 0-15% | Tocopherol |
| 0-15% | Sodium Hyaluronate |
| 0-15% | *Musa sapientum* (Banana) Flower Extract |
| 0-15% | *Centella asiatica* (Hydrocotyl) Extract |
| 0-15% | Vegetable Oil |
| 0-15% | *Rosmarinus officinalis* (Rosemary) Leaf Extract |

Formulation One Hundred Three

| % Range | Ingredient |
| --- | --- |
| 50-100% | Water (Aqua) |
| 3-30% | Octinoxate (7.50%)** Ethylhexyl Methoxycinnamate |
| 3-30% | Octisalate (5%)** Ethylhexyl Salicylate |
| 0-15% | Cetearyl Alcohol |
| 0-15% | C12-15 Alkyl Benzoate |
| 0-15% | Fruit Juice |
| 0-15% | Avobenzone (2%)** Butyl Methoxydibenzoylmethane |
| 0-15% | Dimethicone |
| 0-15% | Butylene Glycol |
| 0-15% | Cetearyl Glucoside |
| 0-15% | Seed Oil |
| 0-15% | Glyceryl Stearate |
| 0-15% | PEG-100 Stearate |
| 0-15% | *Moringa oleifera* Seed Oil |
| 0-15% | *Glycine soja* (Soybean) Seed Extract |
| 0-15% | Phenoxyethanol |
| 0-15% | Caprylyl Glycol |
| 0-15% | *Glycine soja* (Soybean) Sterol |
| 0-15% | Leaf Juice |
| 0-15% | Xanthan Gum |
| 0-15% | *Cocos nucifera* (Coconut) Oil |
| 0-15% | Ethoxydiglycol |
| 0-15% | *Pikea robusta* (Red Algae) Extract |
| 0-15% | Fragrance |
| 0-15% | Potassium Sorbate |
| 0-15% | Panthenol |
| 0-15% | Disodium EDTA |
| 0-15% | *Macrocystis pyrifera* (Kelp) Extract |
| 0-15% | Ceramide 3 |
| 0-15% | Leaf Extract |
| 0-15% | *Curcuma longa* (Turmeric) Root Extract |
| 0-15% | BHT |
| 0-15% | *Vanilla tahitensis* (Vanilla) Fruit Extract |
| 0-15% | Sodium Hyaluronate |
| 0-15% | *Centella asiatica* (Hydrocotyl) Extract |
| 0-15% | *Musa sapientum* (Banana) Extract |
| 0-15% | Tocopherol |
| 0-15% | *Gardenia tahitensis* (Tiare) Flower |

Formulation One Hundred Four

| % Range | Ingredient |
|---|---|
| 50-100% | Water (Aqua) |
| 0-15% | Octinoxate (7.50%)** Ethylhexyl Methoxycinnamate |
| 0-15% | Octisalate (5%)** Ethylhexyl Salicylate |
| 0-15% | Cetearyl Alcohol |
| 0-15% | C12-15 Alkyl Benzoate |
| 0-15% | Fruit Juice |
| 0-15% | Avobenzone (2%)** Butyl Methoxydibenzoylmethane |
| 0-15% | Dimethicone |
| 0-15% | Butylene Glycol |
| 0-15% | Cetearyl Glucoside |
| 0-15% | Seed Oil |
| 0-15% | Glyceryl Stearate |
| 0-15% | PEG-100 Stearate |
| 0-15% | *Moringa oleifera* Seed Oil |
| 0-15% | *Glycine soja* (Soybean) Seed Extract |
| 0-15% | Phenoxyethanol |
| 0-15% | Caprylyl Glycol |
| 0-15% | *Glycine soja* (Soybean) Sterol |
| 0-15% | Leaf Juice |
| 0-15% | Xanthan Gum |
| 0-15% | *Cocos nucifera* (Coconut) Oil |
| 0-15% | Ethoxydiglycol |
| 0-15% | *Pikea robusta* (Red Algae) Extract |
| 0-15% | Fragrance |
| 0-15% | Potassium Sorbate |
| 0-15% | Panthenol |
| 0-15% | Disodium EDTA |
| 0-15% | *Macrocystis pyrifera* (Kelp) Extract |
| 0-15% | Ceramide 3 |
| 0-15% | Leaf Extract |
| 0-15% | *Curcuma longa* (Turmeric) Root Extract |
| 0-15% | BHT |
| 0-15% | *Vanilla tahitensis* (Vanilla) Fruit Extract |
| 0-15% | Sodium Hyaluronate |
| 0-15% | *Centella asiatica* (Hydrocotyl) Extract |
| 0-15% | *Musa sapientum* (Banana) Extract |
| 0-15% | Tocopherol |
| 0-15% | *Gardenia tahitensis* (Tiare) Flower |

Formulation One Hundred Five

| % Range | Ingredient |
|---|---|
| 50-100% | Water (Aqua) |
| 0-15% | Cetearyl Alcohol |
| 0-15% | *Hordeum distichon* (Barley) Extract |
| 0-15% | Fruit Juice |
| 0-15% | Squalane |
| 0-15% | Dimethicone |
| 0-15% | Cetearyl Glucoside |
| 0-15% | *Glycine soja* (Soybean) Seed Extract |
| 0-15% | Phenoxyethanol |
| 0-15% | *Santalum album* (Sandalwood) Extract |
| 0-15% | *Phellodendron amurense* Bark Extract |
| 0-15% | Glycerin |
| 0-15% | *Glycine soja* (Soybean) Sterols |
| 0-15% | Ethoxydiglycol |
| 0-15% | Leaf Juice |
| 0-15% | Bisabolol |
| 0-15% | Potassium Sorbate |
| 0-15% | Butylene Glycol |
| 0-15% | Xanthan Gum |
| 0-15% | *Pikea robusta* (Red Algae) Extract |
| 0-15% | Panthenol |
| 0-15% | Ethylhexylglycerin |
| 0-15% | Disodium EDTA |
| 0-15% | *Macrocystis pyrifera* (Kelp) Extract |
| 0-15% | Ceramide NP |
| 0-15% | *Avena sativa* (Oat) Kernel Extract |
| 0-15% | Leaf Extract |
| 0-15% | Sodium Hyaluronate |
| 0-15% | *Musa sapientum* (Banana) Flower Extract |
| 0-15% | *Centella asiatica* (Hydrocotyl) Extract |

Formulation One Hundred Six

| % Range | Ingredient |
|---|---|
| 35-90% | Water/Aqua |
| 5-50% | Kaolin |
| 3-30% | Bentonite |
| 0-15% | Glyceryl Stearate |
| 0-15% | Silica |
| 0-15% | *Butyrospermum parkii* (Shea Butter) |
| 0-15% | Boron Nitride |
| 0-15% | *Aleurites moluccana* (Kukui) Seed Oil |
| 0-15% | *Macadamia integrifolia* (Macadamia) Seed Oil |
| 0-15% | Cetearyl Alcohol |
| 0-15% | Fruit Juice |
| 0-15% | Ceteareth-20 |
| 0-15% | *Cocos nucifera* (Coconut) Oil |
| 0-15% | Phenoxyethanol |
| 0-15% | Caprylyl Glycol |
| 0-15% | Carbon |
| 0-15% | Bisabolol |
| 0-15% | Xanthan Gum |
| 0-15% | Potassium Sorbate |
| 0-15% | Citric Acid |
| 0-15% | Disodium EDTA |
| 0-15% | Boric Oxide |
| 0-15% | *Plumeria rubra* Flower Extract |
| 0-15% | *Colocasia antiquorum* (Taro) Root Extract |
| 0-15% | *Aleurites moluccana* (Kukui) Seed Extract |
| 0-15% | *Gardenia tahitensis* Flower |
| 0-15% | Tocopherol |

Formulation One Hundred Seven

| % Range | Ingredient |
|---|---|
| 50-100% | Water (Aqua) |
| 0-15% | *Macadamia integrifolia* (Macadamia) Seed Oil |
| 0-15% | *Moringa oleifera* (Moringa) Seed Oil |
| 0-15% | Cetearyl Alcohol |
| 0-15% | *Aleurites moluccana* (Kukui) Seed Oil |
| 0-15% | Dimethicone |
| 0-15% | Fruit Juice |
| 0-15% | Glyceryl Stearate |
| 0-15% | PEG-100 Stearate |
| 0-15% | Seed Oil |
| 0-15% | *Cocos nucifera* (Coconut) Oil |
| 0-15% | Boron Nitride |
| 0-15% | Phenoxyethanol |
| 0-15% | Cetearyl Glucoside |
| 0-15% | Caprylyl Glycol |
| 0-15% | Glucosamine HCl |
| 0-15% | Glycerin |
| 0-15% | Xanthan Gum |
| 0-15% | Leaf Juice |
| 0-15% | Ethoxydiglycol |
| 0-15% | *Pisum sativum* (Pea) Extract |
| 0-15% | Potassium Sorbate |
| 0-15% | *Bambusa vulgaris* (Bamboo) Extract |
| 0-15% | Panthenol |

| % Range | Ingredient |
|---|---|
| 0-15% | Disodium EDTA |
| 0-15% | Steareth-20 |
| 0-15% | Chlorhexidine Digluconate |
| 0-15% | Leaf Extract |
| 0-15% | Boric Oxide |
| 0-15% | Tocopherol |
| 0-15% | *Gardenia tahitensis* (Tiare) Flower |
| 0-15% | N-Hydroxysuccinimide |
| 0-15% | Chrysin |
| 0-15% | Palmitoyl Oligopeptide |
| 0-15% | EDTA |
| 0-15% | Vegetable Oil |
| 0-15% | Palmitoyl Tetrapeptide-7 |
| 0-15% | *Rosmarinus officinalis* (Rosemary) Leaf Extract |

Formulation One Hundred Eight

| % Range | Ingredient |
|---|---|
| 35-90% | Water (Aqua) |
| 0-15% | *Macadamia integrifolia* (Macadamia) Seed Oil |
| 0-15% | *Moringa oleifera* Seed Oil |
| 0-15% | Caprylic/Capric Triglyceride |
| 0-15% | *Aleurites moluccana* (Kukui) Seed Oil |
| 0-15% | Fruit Juice |
| 0-15% | Cetearyl Alcohol |
| 0-15% | Dimethicone |
| 0-15% | Seed Oil |
| 0-15% | *Cocos nucifera* (Coconut) Oil |
| 0-15% | Phenoxyethanol |
| 0-15% | Butylene Glycol |
| 0-15% | Glyceryl Stearate |
| 0-15% | PEG-100 Stearate |
| 0-15% | Caprylyl Glycol |
| 0-15% | Cetearyl Glucoside |
| 0-15% | *Tropaeolum majus* (Nasturtium) Flower/Leaf/Stem Extract |
| 0-15% | Leaf Juice |
| 0-15% | Xanthan Gum |
| 0-15% | Ethoxydiglycol |
| 0-15% | Glycerin |
| 0-15% | Potassium Sorbate |
| 0-15% | Fragrance (Parfum) |
| 0-15% | Magnesium Ascorbyl Phosphate |
| 0-15% | *Arctostaphylos uva ursi* (Bearberry) Leaf Extract |
| 0-15% | Disodium EDTA |
| 0-15% | Tocopherol |
| 0-15% | *Gardenia tahitensis* (Tiare) Flower |
| 0-15% | Leaf Extract |
| 0-15% | Vegetable Oil |
| 0-15% | Diacetyl Boldine |
| 0-15% | *Rosmarinus officinalis* (Rosemary) Leaf Extract |

Formulation One Hundred Nine

| % Range | Ingredient |
|---|---|
| 35-90% | Water (Aqua) |
| 5-50% | *Macadamia integrifolia* (Macadamia) Seed Oil |
| 5-50% | *Aleurites moluccana* (Kukui) Seed Oil |
| 3-30% | Cetearyl Alcohol |
| 0-15% | Fruit Juice |
| 0-15% | Cetearyl Glucoside |
| 0-15% | Glyceryl Stearate |
| 0-15% | PEG-100 Stearate |
| 0-15% | Dimethicone |
| 0-15% | Biosaccharide Gum-1 |

| % Range | Ingredient |
|---|---|
| 0-15% | *Cocos nucifera* (Coconut) Oil |
| 0-15% | Seed Oil |
| 0-15% | *Glycine soja* (Soybean) Seed Extract |
| 0-15% | Phenoxyethanol |
| 0-15% | Caprylyl Glycol |
| 0-15% | *Glycine soja* (Soybean) Sterols |
| 0-15% | Leaf Juice |
| 0-15% | Xanthan Gum |
| 0-15% | Ethoxydiglycol |
| 0-15% | Butylene Glycol |
| 0-15% | *Pikea robusta* (Red Algae) Extract |
| 0-15% | Glucosamine HCl |
| 0-15% | Potassium Sorbate |
| 0-15% | Fragrance |
| 0-15% | Panthenol |
| 0-15% | *Pisum sativum* (Pea) Extract |
| 0-15% | Hydrolyzed *Ulva lactuca* Extract |
| 0-15% | *Calophyllum inophyllum* (Tamanu) Seed Oil |
| 0-15% | Disodium EDTA |
| 0-15% | *Chlorella vulgaris* Extract |
| 0-15% | *Bambusa vulgaris* (Bamboo) Leaf/Stem Extract |
| 0-15% | *Macrocystis pyrifera* (Kelp) Extract |
| 0-15% | Ceramide NP |
| 0-15% | Leaf Extract |
| 0-15% | *Gardenia tahitensis* Flower |
| 0-15% | Tocopherol |
| 0-15% | Sodium Hyaluronate |
| 0-15% | *Musa sapientum* (Banana) Flower Extract |
| 0-15% | *Centella asiatica* (Hydrocotyl) Extract |
| 0-15% | Vegetable Oil |
| 0-15% | *Rosmarinus officinalis* (Rosemary) Leaf Extract |

Formulation One Hundred Ten

| % Range | Ingredient |
|---|---|
| 35-90% | Water (Aqua) |
| 3-30% | Disodium Cocoyl Glutamate |
| 3-30% | *Bambusa arundinacea* (Bamboo) Stem Powder |
| 0-15% | Glyceryl Stearate |
| 0-15% | PEG-100 Stearate |
| 0-15% | Cetearyl Alcohol |
| 0-15% | Sodium Cocoyl Glutamate |
| 0-15% | Fruit Juice |
| 0-15% | Glycerin |
| 0-15% | *Aleurites moluccana* (Kukui) Seed Oil |
| 0-15% | *Macadamia integrifolia* (Macadamia) Seed Oil |
| 0-15% | Squalane |
| 0-15% | *Cocos nucifera* (Coconut) Oil |
| 0-15% | Phenoxyethanol |
| 0-15% | Caprylyl Glycol |
| 0-15% | *Chondrus crispus* (Carrageenan) |
| 0-15% | Seed Oil |
| 0-15% | Citric Acid |
| 0-15% | *Macadamia ternifolia* (Macadamia) Seedcake |
| 0-15% | *Cocos nucifera* (Coconut) Shell Powder |
| 0-15% | Fragrance |
| 0-15% | Potassium Sorbate |
| 0-15% | Disodium EDTA |
| 0-15% | Allantoin |
| 0-15% | *Gardenia tahitensis* (Tiare) Flower |
| 0-15% | Maris Sal |
| 0-15% | Pearl Powder |
| 0-15% | Tocopherol |
| 0-15% | Vegetable Oil |
| 0-15% | *Rosmarinus officinalis* (Rosemary) Leaf Extract |

Formulation One Hundred Eleven

| % Range | Ingredient |
| --- | --- |
| 10-75% | *Macadamia integrifolia* (Macadamia) Seed Oil |
| 10-75% | *Helianthus annuus* (Sunflower) Seed Oil |
| 5-50% | Synthetic Beeswax |
| 3-30% | *Aleurites moluccana* (*Kukui*) Seed Oil |
| 3-30% | *Mangifera indica* (Mango) Seed Butter |
| 0-15% | *Cocos nucifera* (Coconut) Oil |
| 0-15% | Ethylhexyl Palmitate |
| 0-15% | Phenoxyethanol |
| 0-15% | Tribehenin |
| 0-15% | Sorbitan Isostearate |
| 0-15% | Seed Oil |
| 0-15% | *Gardenia tahitensis* (Tiare) Flower |
| 0-15% | Tocopherol |
| 0-15% | *Ananas sativus* (Pineapple) Fruit Extract |
| 0-15% | *Colocasia antiquorum* (Taro) Root Extract |
| 0-15% | *Carica papaya* (Papaya) Fruit Extract |
| 0-15% | Fruit Juice Concentrate |
| 0-15% | Palmitoyl Oligopeptide |

Formulation One Hundred Twelve

| % Range | Ingredient |
| --- | --- |
| 50-100% | Water/Aqua |
| 0-15% | Fruit Juice |
| 0-15% | Polysorbate 20 |
| 0-15% | Phenoxyethanol |
| 0-15% | Caprylyl Glycol |
| 0-15% | Carbomer |
| 0-15% | Glucosamine HCl |
| 0-15% | Leaf Juice |
| 0-15% | Ethoxydiglycol |
| 0-15% | *Pisum sativum* (Pea) Extract |
| 0-15% | Sodium Hydroxide |
| 0-15% | Potassium Sorbate |
| 0-15% | *Bambusa vulgaris* (Bamboo) Extract |
| 0-15% | Panthenol |
| 0-15% | Hydrolyzed Lupine Protein |
| 0-15% | Disodium EDTA |
| 0-15% | Butylene Glycol |
| 0-15% | *Hibiscus rosa-sinensis* Flower Extract |
| 0-15% | *Chondrus crispus* (Carrageenan) Extract |
| 0-15% | Sodium Hyaluronate |
| 0-15% | *Cocos nucifera* (Coconut) Fruit Juice |
| 0-15% | Glucose |
| 0-15% | Leaf Extract |
| 0-15% | EDTA |
| 0-15% | Sorbic Acid |

Formulation One Hundred Thirteen

| % Range | Ingredients |
| --- | --- |
| 0-15% | Leaf Tea Powder |
| 0-15% | *Terminalia chebula*, *Terminalia belerica* and *Embilica officinalis* (Trialpha) Fruit Extract |
| 0-15% | *Tinospora cordifolia* (Indian Tinospora) Stem Extract |
| 50-100% | Honey Powder |
| 0-15% | Firmenich Natural Orange Flavor #860100 TD0991 |
| 0-15% | Allspice |
| 0-15% | Cinnamon |
| 0-15% | Silicon Dioxide |

Formulation One Hundred Fourteen

| % Range | Ingredient |
| --- | --- |
| 0-15% | Vitamin A Palmitate |
| 0-15% | Vitamin C (Ascorbic Acid) |
| 0-15% | Calcium Ascorbate |
| 0-15% | Vitamin D3 (Cholecalciferol) |
| 0-15% | Vitamin E Acetate |
| 0-15% | Vitamin E Acetate |
| 0-15% | Vitamin B5 (d-Calcium Pantothenate) |
| 0-15% | Vitamin H |
| | Calcium from Calcium Ascorbate, d-Calcium Pantothenate, Dibasic Calcium Phosphate, Calcium Chelate |
| 0-15% | Calcium Chelate |
| 10-75% | Dibasic Calcium Phosphate Dihydrate |
| 0-15% | Atlantic Kelp (*Laminaria digitata*) Iodine |
| 0-15% | Ferrous Fumarate |
| 0-15% | Alfalfa Grass |
| 0-15% | Apple Pectin |
| 0-15% | Astragalus Root |
| 0-15% | Barley Grass |
| 0-15% | Bee Pollen Powder |
| 0-15% | Betaine Hydrochloride |
| 0-15% | Broccoli Powder |
| 0-15% | Cabbage Powder |
| 0-15% | Carrot Powder |
| 0-15% | Choline Bitartrate |
| 0-15% | Citrus Pectin |
| 0-15% | Curcumin |
| 0-15% | Echinacea Root |
| 0-15% | Garlic Powder |
| 0-15% | Hesperdin Complex |
| 0-15% | Horsetail |
| 3-30% | Inositol |
| 0-15% | Korean Panex Ginseng Powder |
| 0-15% | Phosphatidylcholine |
| 0-15% | Lemon Bioflavonoids |
| 0-15% | Ligustrum Berry |
| 0-15% | Oat Bran Flour |
| 0-15% | Parsley Powder |
| 0-15% | Quercetin Dihydrate |
| 0-15% | Raspberry Leaf Powder |
| 0-15% | Rose Hip |
| 0-15% | Rutin |
| 0-15% | Schizandra Berry |
| 0-15% | Shiitake Mushroom |
| 0-15% | Eleuthero Root |
| 0-15% | Spinach Powder |
| 0-15% | Suma Powder |
| 0-15% | Tomato Powder |
| 0-15% | Watter Cress Powder |
| 0-15% | Microcrystalline Cellulose |
| 0-15% | Magnesium Stearate |
| 0-15% | Silion Dioxide |

Formulation One Hundred Fifteen

| % Range | Ingredient |
|---|---|
| 0-15% | Beta Carotene |
| 5-50% | Vitamin C (Ascorbic Acid) |
| 5-50% | Vitamin E Acetate |
| 0-15% | Thiamine mononitrate |
| 0-15% | Riboflavin |
| 0-15% | Niacin |
| 0-15% | Niacinamide |
| 0-15% | Pyridoxine Hydrochloride |
| 0-15% | Pyridoxal-5-Phosphate |
| 0-15% | Folid Acid |
| 0-15% | Cyanocobalamin |
| 3-30% | Magnesium Oxide |
| 0-15% | Magnesium Glycinate Chelate |
| 0-15% | Zinc Gluconate |
| 0-15% | Zinc Methionine |
| 0-15% | Zinc Glyinate |
| 0-15% | Selenium Methionate |
| 0-15% | Selenium Glycinate |
| 0-15% | Copper Gluconate |
| 0-15% | Copper |
| 0-15% | Manganese Citrate |
| 0-15% | Manganese Gluconate |
| 0-15% | Manganese Glyinate Chelate |
| 0-15% | Chromium Nicotinyl Glycinate Chelate |
| 0-15% | Potassium Chloride |
| 0-15% | Potassium Glycinate Chelate |
| 0-15% | Potassium Iodine |
| 0-15% | Ferrous Bis-Glycinate |
| 0-15% | Molybdenum |
| 0-15% | Bilberry |
| 0-15% | Calcium Casienate |
| 3-30% | Enzyme Blend |
| 0-15% | Glutamic Acid |
| 0-15% | Glutathione L. |
| 0-15% | Grape Seed |
| 0-15% | Green Tea Leaf |
| 0-15% | Methionine L. |
| 0-15% | Liver Spray Dried |
| 0-15% | Papaya Leaf |
| 0-15% | Pineapple Fruit |
| 0-15% | Pine Bark |
| 0-15% | Red Wine |
| 0-15% | Silica |
| 0-15% | Vanadium |
| 5-50% | Dicalcium Phosphate Dihydrate |
| 5-50% | Phosphorus from Dicalcium Phosphate Dihydrate |
| 3-30% | Microcrystalline Cellulose |
| 0-15% | Magnesium Stearate |
| 0-15% | Silicon Dioxide |

EXAMPLES

The following example illustrates some of the embodiments of the present invention comprising the administration of a composition comprising components of the Indian Mulberry or *Morinda citrifolia* L. plant. These examples are not intended to be limiting in any way, but are merely illustrative of benefits, advantages, and remedial effects of some embodiments of the *Morinda citrifolia* compositions of the present invention.

As illustrated by the following Example, embodiments of the present invention have been tested. Specifically, the Example illustrates the results of in-vitro studies that confirmed that concentrates of processed *Morinda citrifolia* products ("TNJ" is an evaporative concentrate) and processed plants selected as sources of iridoids have unexpected beneficial physiological effects. The percentage of concentration refers to the concentration strength of the particular concentrate tested; that is, the strength of concentration relative to the processed product from which the concentrate was obtained.

Example One

A human clinical trial of TAHITIAN NONI® Juice in heavy smokers revealed that ingestion of noni juice has DNA protective activity. Phytochemical analysis of TAHIITIAN NONI® Juice has revealed iridoids, specifically deacetylasperulosidic acid (DAA) and asperulosidic acid (AA) are the major phytochemcial constituents of noni fruit. DAA and AA were isolated from noni fruit puree from French Polyensia to evaluate their DNA protective potentials in vitro and make an assessment of their role in the results observed in the clinical trial.

The SOS-chromotest in *E. coli* PQ37 was used to determine the potential for iridoids in noni fruit from French Polynesia to prevent primary DNA damage. *E. coli* PQ37 was incubated at 37° C. in the presence of deacetylasperulosidic acid and asperulosidic acid at a concentration of 250 ug mL$^{-1}$ in a 96-well plate. Replicate samples were evaluated. The samples were also incubated with 1.25 ug mL$^{-1}$ 4-nitroquinoline 1-oxide (4NQO). Blank replicates were also prepared, where cells were not incubated with to iridoids or 4NQO. Additionally, a 1.25 ug mL$^{-1}$ 4NQO positive control was included in this assay. Following incubation with the samples, 5-bromo-4-chloro-3-indolyl-β-D-galactopyranoside was added to the wells to detect β-galactosidase enzyme activity, which is induced during SOS repair of damaged DNA. The samples were again incubated for 90 minutes and the absorbances of the samples, blank and positive control were measured at 620 nm with a microplate reader. The β-galactosidase enzyme activity induction factor of each material was calculated by dividing the absorbance of the sample at 620 nm by that of the blank, while also correcting for cell viability. Induction factors of the blank, which by definition is 1, the positive control, and the sample wells containing DAA, plus 4NQO, and AA, plus 4NQO, were compared.

The β-galactosidase enzyme activity induction factor of 1.25 ug mL$^{-1}$ 4NQO was 6.09, indicating a six-fold increase in DNA damage in the cells. The induction factors (mean±standard deviation) of the DAA and AA samples, each containing 1.25 ug mL$^{-1}$ 4NQO, were 0.98±0.02 and 1.04±0.01, respectively. The results are compared graphically in FIG. 6. The results reveal that the DNA damaging ability of 4NQO was abolished by the addition of the iridoids.

The iridoids, DAA and AA, in noni fruit have the potential to protect DNA against 4NQO, a well known genotoxin. TAHITIAN NONI® Juice has also been shown to provide some level of DNA protection in humans against cigarette smoke, also a well known genotoxin. Further, chemical analysis has revealed that the major phytochemicals in noni fruit and TAHITIAN NONI® Juice are iridoids, specifically DAA and AA. Therefore, it can be concluded that these iridoids are responsible for, or at least have a prominant role in, the DNA protective effects of noni juice observed in the human clinical trial involving heavy smokers.

Example Two

Analytical method to determine the quantity of iridoids in noni plant, as well as other fruits and their juices were developed. Major iridoids were isolated from the *Morinda citrifolia* plant as follows:

Chemicals and Standards

Acetonitrile (MeCN), methanol (MeOH), and water (H$_2$O) of HPLC grade were obtained from Sigma-Aldrich (St.

Louis, Mo., USA). Formic acid of analytical grade was purchased from Spectrum Chemical Mfg. Corp. (New Brunswick, N.J., USA). The chemical standard deacetylasperulosidic acid (DAA, 1) and asperulosidic acid (AA, 2) were isolated from noni fruits in our laboratory. Their purities were determined by HPLC and NMR to be higher than 99%. The chemical structures of DAA and AA are listed in FIG. 1. They were accurately weighed and then dissolved in an appropriate volume of MeCN to produce corresponding stock solutions. The working standard solution of 1 and 2 for the calibration curve was prepared by diluting the stock solution with MeOH in seven concentration increments ranging from 0.00174-1.74 and 0.0016-0.80 mg/mL, respectively. All stock and working solutions were maintained at 0° C. in a refrigerator. The calibration curves of standards were plotted after linear regression of the peak areas versus concentrations.

Materials and Sample Preparation

Tahitian noni fruit puree as used in this example is the mashed whole fruit, excluding seeds and pericarp. The fruits were originally collected from the Tahitian Islands. One gram of the puree was diluted with 5 mL of $H_2O$-MeOH (1:1) and mixed thoroughly. The solution was then filtered through a nylon microfilter (0.45-µm pore size); the solution was collected into a 5 mL volumetric flask for HPLC analysis. Four batches of noni puree were analyzed in the experiments. Voucher specimens of the noni fruit puree are deposited in our lab. To test iridoid stability, a DAA solution of 0.5 mg/mL was prepared with MeOH. This solution was heated in a water-bath at 90° C. for 1 min, cooled to room temperature, and analyzed by HPLC.

The injection volume was 10 µL for each of the sample solutions. The column temperature was maintained at 25° C. Data collection and integration were performed using Waters Millennium software revision 32.

Method Validation

The limits of detection (LOD) and quantitation (LOQ) were defined as the lowest concentrations of analytes in a sample that can be detected and quantified. These LOD and LOQ limits were determined on the basis of signal-to-noise ratios (S/N) of 3:1 and 10:1, respectively. The working solutions of standards 1 and 2 for LOD and LOQ were prepared by diluting them sequentially. The intra- and inter-day precision assays, as well as stability tests were performed by following the method applied to the sample analysis for 3 consecutive days. Accuracy of the method (recovery) was assessed by the recovery percentage of iridoids 1 and 2 in the spiked samples. The noni fruit puree samples were spiked with standards at 3 different concentrations (equivalent to 50%, 100% and 150% concentration of 1 and 2 in the samples). The recovery percentage was calculated using the ratio of concentration detected (actual) to those spiked (theoretical). Variation was evaluated by the relative standard deviation (RSD) of triplicate injections in the HPLC experiments.

Samples Analyzed

Several fruits and fruit juice products, such as purees, were prepared and analyzed according to the methods described above. Samples of various commercial brand name fruit juices were also analyzed. Samples of noni leaves and seeds were also analyzed. The analytical results are provided in the following tables.

FIG. 7 Iridoids analysis of fruit puree and juice concentrates (mg/mL-blueberry, all others-mg/g)

| Samples/ | lot# or note | DAA[a] | AA[b] | Other iridoids | Total iridoids |
|---|---|---|---|---|---|
| Tahitian noni fruit puree | P06151-2429 | 1.308 ± 0.110 | 0.276 ± 0.003 | 0.0535 | 1.638 |
| | 16523 | 1.441 ± 0.027 | 0.218 ± 0.009 | 0.0570 | 1.716 |
| | 16524 | 1.274 ± 0.014 | 0.256 ± 0.017 | 0.0535 | 1.584 |
| | 7807 | 1.531 ± 0.057 | 0.296 ± 0.057 | 0.0520 | 1.879 |
| blueberry juice concentrate | | n.d.[c] | | 0.0621* | 0.061 |
| grape juice concentrate | | n.d.[c] | | | |
| acai puree | | n.d.[c] | | | |
| mongosteen whole fruit | extracted with MeOH | n.d.[c] | | | |
| | extracted with H2O | n.d.[c] | | | |
| mangosteen fruit puree | | n.d.[c] | | | |
| pear puree | | n.d.[c] | | | |
| goji juice | | n.d.[c] | | | |
| cupuacu puree | | n.d.[c] | | | |

[a] deacetylasperulosidic acid (daa);
[b] asperulosidic acid (aa);
[c] not detected;
*monotropein from blueberry.

Chromatographic Conditions and Instrumentation

Chromatographic separation was performed on a Waters 2690 separations module coupled with 996 PDA detectors, and equipped with an Atlantis C18 column (4.6 mm×250 mm; 5 µm, Waters Corporation, Milford, Mass., USA). The pump was connected to two mobile phases: A; MeCN, and B; 0.1% formic acid in $H_2O$ (v/v), and eluted at a flow rate of 0.8 mL/min. The mobile phase was programmed consecutively in linear gradients as follows: 0-5 min, 0% A; and 40 min, 30% A. The PDA detector was monitored in the range of 210-400 nm (235 nm was selected for quantitative analysis).

TABLE 2

Iridoids analysis of commercial brand name fruit juice blends (mg/mL)

| Samples/ Sources (note) | | DAA[a] | AA[b] | Other iridoids | Total iridoids |
|---|---|---|---|---|---|
| TNJ | TNI | 0.462 ± 0.016 | 0.030 ± 0.001 | 0.0667 | 0.568 |
| Acai blend juice | Monavie | n.d.[c] | | 0.0126* | 0.013 |
| | | n.d.[c] | | 0.00809* | 0.008 |

TABLE 2-continued

Iridoids analysis of commercial brand name fruit juice blends (mg/mL)

| Samples/ Sources (note) | | DAA$^a$ | AA$^b$ | Other iridoids | Total iridoids |
|---|---|---|---|---|---|
| Xango juice | Xango, 330 ml pouch | n.d.$^c$ | | 0.0289* | 0.029 |
| | Xango, bottled | n.d.$^c$ n.d.$^c$ | | 0.0178* 0.0155* | 0.0178 0.0155 |
| GoChi ™ Goji juice | Freelife Intl. | n.d.$^c$ | | 0.0531** | 0.0531 |
| Le'Vive juice | Ardyness intl. | 0.0147 | n.d.$^c$ | 0.0183** | 0.0330 |
| Zrii juice | Zrii | | n.d.$^c$ | | |
| G3 | Nuskin | | n.d.$^c$ | | |
| Kyani fruit juice | Kyani | | n.d.$^c$ | | |

$^a$deacetylasperulosidic acid (daa);
$^b$asperulosidic acid(aa);
$^c$not detected;
*monotropein from blueberry;
**tentatively identified as iridoids based on its UV, further confirmation needed.

TABLE 3

Iridoids analysis of noni different plant parts (mg/g)

| Samples | Notes | DAA$^a$ | AA$^b$ | Other iridoids | Total iridoids |
|---|---|---|---|---|---|
| Tahitian noni fruit puree (wet) | | 1.441 ± 0.027 | 0.218 ± 0.009 | 0.0570 | 1.716 |
| Tahitian noni whole fruit (dried) | grounded into powder, extracted with MeOH/EtOH (1:1) | 3.741 ± 0.016 | 1.253 ± 0.0051 | 0.420 | 5.414 |
| Tahitian noni leaf | | 0.338 ± 0.028 | 0.539 ± 0.0075 | 0.388 | 1.265 |
| Tahitian noni root | | 0.0873 ± 0.008 | 0.326 ± 0.0309 | 1.714* | 2.127 |
| Tahitian noni seed | | 1.303 ± 0.050 | 0.148 ± 0.0106 | n.d.$^c$ | 1.451 |
| Noni blossom | extracted with MeOH (1:100) 30' sonicated | 0.88 | 0.421 | 1.268 | 2.569 |

$^a$deacetylasperulosidic acid (daa);
$^b$asperulosidic acid(aa);
$^c$not detected;
*tentatively identified as iridoids based on its UV, further confirmation needed.

Major phytochemical component of noni fruit and TAHITIAN NONI® Juice are iridoids, specifically deacetylasperuloside and asperulosidic acid. A small quantity of another iridoid is found in blueberry fruit juice concentrate, at approximately 3.8% of the total iridoid content of noni fruit puree. The other fruits and non-noni fruit products did not contain iridoids.

The present invention may be embodied in other specific forms without departing from its spirit of essential characteristics. The described embodiments are to be considered in all respects only as illustrative and not restrictive. The scope of the invention is, therefore, indicated by the appended claims, rather than by the foregoing description. All changes that come within the meaning and range of equivalency of the claims are to be embraced within their scope.

Example Three

The proximate nutritional, vitamin, mineral, and amino acid contents of processed noni fruit puree were determined. The phytochemical properties were evaluated, as well as an assessment made on the safety and potential efficacy of the major phytochemicals present in the puree. Processed noni fruit puree is a potential dietary source of vitamin C, vitamin A, niacin, manganese, and selenium. Vitamin C is the major nutrient present, in terms of concentration. The major phytochemicals in the puree are iridoids, especially deacetylasperulosidic acid, which were present in higher concentrations than vitamin C. The iridoids in noni did not display any oral toxicity or genotoxicity, but did possess potential anti-genotoxic activity. These findings suggest that deacetylasperulosidic acid may play an important role in the biological activities of noni fruit juice that have been observed in vitro, in vivo, and in human clinical trials.

1. Introduction

*Morinda citrifolia*, commonly known as noni, is a widely distributed tropical tree. It grows on the islands of the South Pacific, Southeast Asia, Central America, Indian subcontinent, and in the Caribbean. Knowledge of the phytochemical profile of processed noni fruit puree is important in understanding potential bioactivities, as well as in understanding the compounds responsible for health effects already demonstrated in human clinical trials. Iridoids constitute the major phytochemical component of noni fruit, with a few other compounds, such as scopoletin, quercetin, and rutin have occurring in significant, although much less, quantities. Previous analyses have been limited in the amount of nutrient data provided. Further, they have not been representative of the commercially processed noni fruit puree, as processing conditions do alter the nutritional and phytochemical profiles of fruits and vegetables. Therefore, the current chemical analyses were performed to provide more complete and accurate nutritional data. Analyses of the major phytochemicals in noni fruit were also carried out to provide an important reference for quality control and identity testing of these raw materials.

As the iridoids are present in significant quantities in noni fruit puree, genotoxicity and acute toxicity tests were performed to better understand their individual safety profiles. Therefore, the anti-genotoxic activities of the iridoids were evaluated in vitro, to investigate their potential roles in this reported DNA protection.

2. Materials and Methods
2.1 Experimental Materials

Noni fruits were harvested in French Polynesia and allowed to fully ripen. The fruit was then processed into a puree by mechanical removal of the seeds and skin via micro-mesh screen in a commercial fruit pulper, followed by pasteurization (87° C. for 3 seconds) at a good manufacturing certified fruit processing facility in Mataiea, Tahiti. The pasteurized puree is filled into aseptic containers, or totes containing 880 kg of noni fruit puree, and stored under refrigeration. Samples were obtained from 10 totes, from different batches, for the chemical analyses in this study.

For the acute oral toxicity test, an iridoid enriched fruit extract was prepared. This was done by removal of seeds and skin from the fruit flesh, followed by size reduction with a 0.65 mm sieve. An aqueous extract was prepared with the remaining fruit pulp, at ambient temperature, which was then freeze-dried, resulting in a total iridoid concentration of 1690 mg/100 g extract.

Freeze-dried noni fruit powder (36 g) was extracted with 1 L of methanol by percolation to produce 10 g of methanol extract. Following addition of water, the methanol extract was partitioned with ethylacetate (150 mL three times) to remove non-polar impurities. The aqueous extract was further partitioned with n-butanol (150 mL three times) to yield 3 g n-butanol extract. The extract was subjected to flash column chromatography on silica gel, eluting with a stepwise dichloromethane:methanol (20:1→1.5:1) gradient solvent system to yield sixty-two primary fractions. Among these, the presence of two major compounds was indicated by a preliminary HPLC analysis. The iridoid containing fractions were combined and subject to further purification by using reverse phase preparative HPLC (Symmetry Prep™ C18 column, Waters Corp.), eluting with an isocratic solvent system of MeCN—H2O (35:65) at a flow rate of 3 mL/min, resulting in the isolation of DAA and AA.

2.2 Chemical Analyses

Proximate nutritional analyses of noni fruit puree were carried out to determine moisture, fat, protein, ash, and carbohydrate contents. Protein content was determined by the Kjedahl method, Association of Official Analytical Chemists (AOAC) Method 979.09 (AOAC, 2000a). Total moisture was determined gravimetrically by loss on drying at 100° C. in a vacuum oven. Fat determination involved continuous extraction by petroleum ether in a Soxhlet apparatus, AOAC Method 960.39 (AOAC, 2000 b). Ash was determined gravimetrically following combustion in a furnace at 550° C. Carbohydrate was then calculated by difference. Total dietary fiber was determined according to AOAC Method 991.43 (AOAC, 2000 c). Fructose, glucose, and sucrose contents were determined according to AOAC method 982.14 (AOAC, 2000 d).

Minerals were determined by inductively coupled plasma (ICP) emission spectrometry (AOAC, 2000 e; AOAC, 2000 f). Vitamin A, as β-carotene, was determined by a modified AOAC official method 941.15 for an HPLC system (AOAC, 2000 g). Vitamin C was determined by titration with 2,6-dichloroindophenol, by the microfluorometric method, or by HPLC and UV detection of oxidized ascorbic acid (AOAC, 2000 h; AOAC, 2000l). Niacin, thiamin, riboflavin, vitamin B6, vitamin B12, vitamin E, folic acid, biotin, and pantothenic acid were determined by AOAC and United States Pharmacopoeia methods (AOAC, 2000 j; AOAC, 2000 k; AOAC, 2000 l; AOAC, 2000 m; AOAC, 2000 n; AOAC, 2000 0; AOAC, 2000 p; United States Pharmacopeia, 2005; Scheiner & De Ritter, 1975). Vitamin E was determined by HPLC similar to a previously reported method (Omale and Omajali, 2010), but with direct organic solvent extraction and use of a 2-propanol:$H_2O$ (60:20, %:%) mobile phase. Vitamin K was determined according to AOAC method 992.27 (AOAC, 2000 p). Amino acids were determined with an automated amino acid analyzer, following acid hydrolysis, except for tryptophan which involved hydrolysis with sodium hydroxide (AOAC, 2000 q).

The iridoid content, inclusive of deacetylasperulosidic acid (DAA) and asperulosidic acid (AA), was determined by HPLC, according to a previously reported method (Deng et al., 2010 b). Other significant secondary metabolites, such as scopoletin, rutin, and quercetin, were also determined by HPLC (Deng et al., 2010a).

2.4 Acute Toxicity Test of Iridoids

Twenty healthy Sprague-Dawley rats (10 males, 10 females, body weight 181-205 g) were selected for the tests. An iridoid enriched fruit extract was dissolved in water to produce a total iridoid concentration of 8.5 mg/mL. A dose of 340 mg total iridoids/kg body weight (bw) was given to each animal by gastric intubation (20 mL/kg bw twice per day). For 14 days following the administration of the iridoid solution, animals were observed daily for occurrences of death and symptoms of toxicity, including convulsions, irregular breathing, piloerection, and paralysis. As decreased weight is a typical symptom of toxicity, body weights were recorded for each animal on days 0 and 14. The acute toxicity test was carried out in accordance with EC Directive 86/609/EEC (European Communities, 1986).

2.5 Primary DNA Damage Test in *E. coli* PQ37

The SOS-chromotest in *E. coli* PQ37 was used to determine the potential for DAA and AA to induce primary DNA damage. This test was carried out according to the previously developed method (Fish et al., 1987). DAA and AA were isolated from noni fruits from Tahiti and purified to >98%. *E. coli* PQ37 was incubated in LB medium in a 96-well plate at 37° C. in the presence of DAA or AA for 2 hours. The DAA and AA concentrations tested were 7.81, 15.6, 31.2, 62.5, 125, 250, 500, and 1000 µg mL$^{-1}$. Samples were evaluated in triplicate. Following incubation with the samples, 5-bromo-4-chloro-3-indolyl-β-D-galactopyranoside was added to the wells to detect β-galactosidase enzyme activity, which is induced during SOS repair of damaged DNA. Nitrophenyl phosphate is also added to the wells to measure alkaline phosphatase activity, an indicator of cell viability. The samples were again incubated and the absorbances of the samples, blanks and controls were measured at 410 and 620 nm with a microplate reader. Vehicle blanks and positive controls, 1.25 µg mL$^{-1}$ 4-nitroquinoline 1-oxide (4NQO), were included in this test. The induction factor of each material was calculated by dividing the absorbance of the sample at 620 nm by that of the blank, while also correcting for cell viability. Induction factors less than two indicate an absence of genotoxic activity.

2.6 Anti-Genotoxicity Test in *E. coli* PQ37

The primary DNA damage test was performed again, similar to the method described above. However, the method was modified to include incubation of *E. coli* PQ37 in the presence of both 1.25 µg mL$^{-1}$ 4NQO and 250 µg mL$^{-1}$ DAA or AA. Induction factors were calculated in the same manner as described above. The percent reduction in genotoxicity was determined by dividing the difference between the induction factor of 4NQO and the blank (induction factor of 1) by the difference between the induction factor of 4NQO plus DAA or AA and the blank.

2.7 Statistical Analyses

Means and standard deviations were calculated for each set of analytical results obtained from the different batches. In both the primary DNA damage test and the anti-genotoxicity test, intergroup comparisons were made with Student's t-test.

3. Results and Discussion

The nutrient composition of processed noni fruit puree is summarized in FIG. 10. Proximate nutritional parameters are within the typical ranges for fruits in general. Processed noni fruit puree contains 2 g 100 g$^{-1}$ dietary fiber. Noni fruit does not contain a significant quantity of protein or fat. However, all but one essential amino acid, tryptophan, as well as histidine, essential for infants, were detected in the puree (Table 5). Aspartic acid was the most predominant amino acid.

TABLE 4

Nutrient content of processed noni fruit puree.

| Assay | Mean | S.D. |
|---|---|---|
| Protein (g/100 g) | 0.55 | 0.11 |
| Fat (g/100 g) | 0.10 | 0.12 |
| Moisture (g/100 g) | 91.63 | 1.98 |
| Ash (g/100 g) | 0.54 | 0.19 |
| Carbohydrate (g/100 g) | 7.21 | 1.81 |
| Fructose (g/100 g) | 1.07 | 0.39 |
| Glucose (g/100 g) | 1.30 | 0.36 |
| Sucrose (g/100 g) | <0.1 | — |
| Kilojoules/100 g | 135.56 | 31.73 |
| Dietary fiber (g/100 g) | 2.01 | 0.27 |
| Ca (mg/100 g) | 48.20 | 16.04 |
| K (mg/100 g) | 214.34 | 56.91 |
| Na (mg/100 g) | 16.99 | 5.98 |
| Mg (mg/100 g) | 26.10 | 8.33 |
| P (mg/100 g) | 20.35 | 6.78 |
| Fe (mg/100 g) | 0.74 | 0.06 |
| Cu (mg/100 g) | 0.08 | 0.07 |
| Mn (mg/100 g) | 0.47 | 0.62 |
| Se (mg/100 g) | 0.01 | 0.01 |
| Zn (mg/100 g) | 0.06 | 0.07 |
| β-carotene (µg/g) | 19.09 | 12.15 |
| Niacin (mg/g) | 0.03 | 0.01 |
| Vitamin C (mg/g) | 1.13 | 0.77 |
| Thiamin (mg/g) | <0.018 | — |
| Riboflavin (mg/g) | <0.018 | — |
| Vitamin B6 (mg/g) | <0.018 | — |
| Vitamin B12 (µg/g) | <0.0012 | — |
| Vitamin E (µg/g) | 10.96 | 6.62 |
| Folic acid (µg/g) | <0.06 | — |
| Biotin (µg/g) | 0.02 | 0.00 |
| Pantothenic acid (mg/g) | <0.018 | — |
| Vitamin K (µg/g) | <0.10 | — |

S.D. = standard deviation.

TABLE 5

Amino acid profile of processed noni fruit puree.

| Amino acid | Mean | S.D. |
|---|---|---|
| Alanine (mg/g) | 0.45 | 0.04 |
| Arginine (mg/g) | 0.32 | 0.04 |
| Aspartic acid (mg/g) | 0.80 | 0.08 |
| Cystine (mg/g) | 0.23 | 0.03 |
| Glutamic acid (mg/g) | 0.64 | 0.05 |
| Glycine (mg/g) | 0.36 | 0.04 |
| Histidine (mg/g) | <0.1 | — |
| Isoleucine (mg/g) | 0.29 | 0.01 |
| Leucine (mg/g) | 0.38 | 0.02 |
| Lysine (mg/g) | 0.25 | 0.04 |
| Methionine (mg/g) | <0.1 | — |
| Phenylalanine (mg/g) | 0.21 | 0.05 |
| Proline (mg/g) | 0.26 | 0.03 |
| Serine (mg/g) | 0.27 | 0.02 |
| Threonine (mg/g) | 0.27 | 0.03 |
| Tryptophan (mg/g) | <0.1 | 0.00 |
| Tyrosine (mg/g) | 0.25 | 0.03 |
| Valine (mg/g) | 0.36 | 0.03 |

Vitamin C is the most prominent vitamin in noni fruit puree, with a mean content of 1.13 mg$^{-1}$ g. At this concentration, 100 g of puree provides 251% of the recommended daily vitamin C requirement for adults (FAO/WHO, 2001). Noni fruit puree contains appreciable quantities of β-carotene. As calculated from β-carotene concentration, the mean vitamin A content per 100 g of puree is 318.17 retinol equivalents (RE). The joint FAO/WHO recommendation for average vitamin A daily intake by adults is 270 RE for females and 300 RE for males (FAO/WHO, 1998). As such, noni fruit puree appears to have the potential to be a significant dietary source of vitamin A. The niacin content of processed noni fruit is great enough to have some nutritional impact, but will only be significant when larger quantities are consumed. At 100 g, the puree provides 18 to 21% of the recommended niacin intake for adults (FAO/WHO, 2001). Thiamin, riboflavin, vitamin B6, vitamin B12, folic acid, pantothenic acid, and vitamin K were below detection limits. Processed noni fruit puree contains, but is not a significant source of, vitamin E and biotin.

Potassium appears to be the most abundant mineral in processed noni fruit puree. It is more than four times the concentration of calcium, the next most abundant mineral, although neither is present in nutritionally significant quantities. Only two minerals are present in nutritionally significant amounts. In 100 g of noni puree, manganese and selenium contents would meet approximately 18 to 26% of the recommended daily allowance for adults (Institute of Medicine, 2000; Institute of Medicine, 2001).

The phytochemical analyses reveal that iridoids are the major secondary metabolites produced by noni fruit and are present in significant quantities following processing (Table 6). Scopoletin, rutin, and quercetin were also present after processing. The total iridoid content was 20 times greater than the combined concentrations of the other three phytochemicals. Deacetylasperulosidic acid accounted for 78% of the total iridoid content. Due to their prevalence in noni fruit, both iridoids may be used as markers for identification of products containing authentic noni ingredients. Bioactivities of iridoids from noni fruit juice and noni fruit extracts may ionclude antioxidant, anti-inflammatory, immunomodulatory, hepatoprotective, and hypolipidemic activities.

No deaths or symptoms of toxicity were observed in the acute toxicity test. Animals also gained appropriate weight (Table 7). The LD$_{50}$ of noni iridoids was determined to be >340 mg/kg bw. In the primary DNA damage test in *E. coli* PQ37 (Table 8), the mean induction factors for DAA and AA, at 1000 µg mL$^{-1}$, were 1.07 and 1.09, respectively. At all concentrations tested, DAA and AA did not induce any SOS repair at a frequency significantly above that of the blank. Statistically, induction factors were no different than that of the blank, and all results remained well below the two-fold criteria for genotoxicity. SOS-chromotest results have a high level of agreement (86%) with those from the reverse mutation assay (Legault et al., 1994). Therefore, the SOS-chromotest has some utility in predicting potential mutagenicity, in addition to primary DNA damage. The lack of DAA and AA toxicity in these tests are consistent with the results of toxicity tests of noni fruit juice (West et al., 2009a; West et al., 2009 b; Westendorf et al., 2007).

TABLE 6

Phytochemical content of precessed noni fruit puree.

| Assay | Mean | S.D. |
|---|---|---|
| Deacetylasperulosidic acid (mg/100 g) | 137.61 | 13.69 |
| Asperulosidic acid (mg/100 g) | 38.79 | 9.18 |
| Scopoletin (mg/100 g) | 5.68 | 1.58 |
| Rutin (mg/100 g) | 1.42 | 0.84 |
| Quercetin (mg/100 g) | 1.59 | 0.71 |

TABLE 7

Acute toxicity test of noni iridoids.

| Animal | Sex | Animal number | Body weight (g) Before | Body weight (g) After | $LD_{50}$ (mg iridoids/kg bw) |
|---|---|---|---|---|---|
| S.D. rat | Male | 10 | 191.2 ± 5.9 | 216.1 ± 8.3 | >340.0 |
| | Female | 10 | 192.8 ± 12.3 | 289.4 ± 12.3 | >340.0 |

In the anti-genotoxicity test, 4NQO, exhibited obvious genotoxicity, inducing SOS repair more than 8-fold above that of the vehicle blank. But the induction factors of 4NQO plus DAA or AA, were the same as those of DAA or AA alone (Table 9), with no statistical difference from that of the vehicle blank. The reductions in genotoxicity from 250 μg mL$^{-1}$ DAA and AA were 98.96 and 99.22%, respectively. Therefore, the genotoxic activity of 4NQO was almost entirely abolished by the addition of either iridoid.

A double-blind human clinical trial revealed that ingestion of noni fruit juice reduced the amount of aromatic DNA-adduct formation in the lymphocytes of current heavy cigarette smokers. 4NQO exhibits genotoxic activity in E. coli through the formation of 4NQO-guanine and 4NQO-adenine adducts. These DNA lesions lead to the induction of the SOS repair mechanism. As such, the reduction in 4NQO genotoxicity by DAA and AA equates to a reduction in DNA adduct formation. Therefore, the results of the current anti-genotoxicity test suggest the possible involvement of these iridoids in noni juice's DNA protective effects.

4. Conclusion

Processed noni fruit puree is a potential dietary source of vitamin C, vitamin A, niacin, manganese, and selenium. Vitamin C is the major nutrient present, in terms of concentration. The major phytochemicals in the puree are iridoids, especially DAA. The iridoids in noni did not display any toxicity. On the other hand, these iridoids did display potential anti-genotoxic activity. Even though processed noni fruit puree contained an appreciable quantity of vitamin C, the average DAA content was approximately 22% greater than that of vitamin C. These findings suggest that DAA may play an important role in the biological activities of noni fruit juice that have been observed in vitro, in vivo, and in human clinical trials.

TABLE 8

Primary DNA damage assay in E. coli PQ37.

| Compound | Concentration (μg mL$^{-1}$) | Induction factor |
|---|---|---|
| Deacetylasperulosidic acid | 1000 | 1.07 ± 0.14 |
| | 500 | 1.03 ± 0.02 |
| | 250 | 1.06 ± 0.06 |
| | 125 | 1.00 ± 0.08 |
| | 62.5 | 1.05 ± 0.07 |
| | 31.2 | 1.04 ± 0.08 |
| | 15.6 | 1.03 ± 0.16 |
| | 7.81 | 0.93 ± 0.13 |
| Asperulosidic acid | 1000 | 1.09 ± 0.03 |
| | 500 | 1.07 ± 0.04 |
| | 250 | 1.11 ± 0.16 |
| | 125 | 1.02 ± 0.08 |
| | 62.5 | 1.04 ± 0.13 |
| | 31.2 | 0.99 ± 0.06 |
| | 15.6 | 1.04 ± 0.11 |
| | 7.81 | 1.01 ± 0.05 |
| 4NQO | 1.25 | 8.69 ± 3.69* |

*P < 0.05, compared to vehicle blank.

TABLE 9

Anti-genotoxicity test in E. coli PQ37.

| Compound | Concentration (μg mL$^{-1}$) | Induction factor |
|---|---|---|
| Positive control (4NQO) | 1.25 | 8.69 ± 3.69** |
| 4NQO + deacetylasperulosidic acid | 250* | 1.08 ± 0.12 |
| 4NQO + asperulosidic acid | 250* | 1.06 ± 0.03 |

*DAA or AA concentration; 4NQO concentration is 1.25 μg mL$^{-1}$.
**P < 0.05, compared to vehicle blank.

Example Four

Noni is a medicinal plant with a long history of use as a folk remedy in many tropical areas, and is attracting more attention worldwide. A comprehensive study on the major phytochemicals in different noni plant parts, such as fruit, leaf, seed, root and flower is of great value for fully understanding their diverse medicinal benefits. Moreover, the diversity of geographic environments may contribute to the variation of noni's components.

Objective—

This study quantitatively determines the major iridoid components in different parts of noni plants, and compares iridoids in noni fruits collected from different tropical areas worldwide.

Methodology—

The optimal chromatographic conditions were achieved on a $C_{18}$ column with gradient elution using 0.1% formic acid aqueous formic acid and acetonitrile at 235 nm. The selective HPLC method was validated for precision, linearity, limit of detection (LOD), limit of quantitation (LOQ), and accuracy.

Results—

Deacetylasperulosidic acid (DAA) was found to be the major iridoid in noni fruit. In order of predominance, DAA concentrations in different parts of the noni plant were dried noni fruit>fruit juice>seed>flower>leaf>root. The order of predominance for asperulosidic acid (AA) concentration was dried noni fruit>leaf>flower>root>fruit juice>seed. DAA and AA contents of methanolic extracts of noni fruits collected from different tropical regions were 13.8-42.9 mg/g and 0.7-8.9 mg/g, respectively, with French Polynesia containing the highest total iridoids and the Dominican Republic containing the lowest.

Conclusion—

Iridoids are found to be present in leaf, root, seed, and flower of noni plants, and were identified as the major components in noni fruit. Given the great variation of iridoid contents in noni fruit grown in different tropical areas worldwide, geographical factors appear to have significant effects on fruit composition. The iridoids in noni fruit were stable at temperatures used during pasteurization and, therefore, may be useful marker compounds for identity and quality testing of commercial noni products.

Introduction

Noni (Morinda citrifolia Linn.) is a popular medicinal plant indigenous to a wide range of tropical areas, such as southern Asia, the Caribbean, and the Pacific Islands. This study aims to quantitatively determine the major iridoids in different parts of noni (fruit, leaf, root, seed, and flower), and comparatively analyze the iridoids in different noni fruits cultivated and collected worldwide, by using a validated HPLC-PDA method.

Chemicals and Standards

Figure 4:
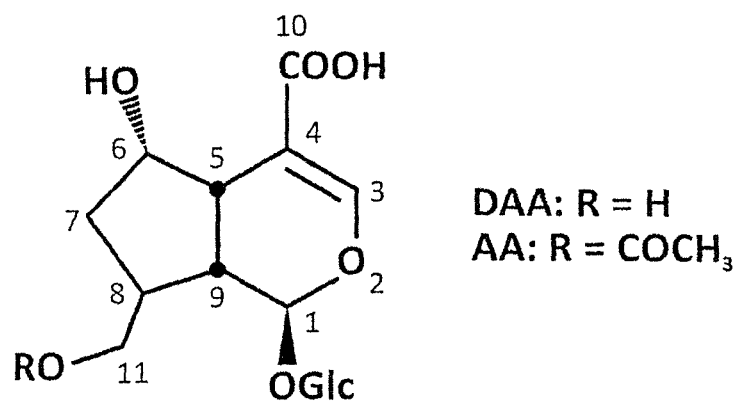
FIG. 4 depicts the chemical structures of deacetylasperulosidic acid and asperulosidic acid.

HPLC grade acetonitrile (MeCN), methanol (MeOH), and water ($H_2O$) were obtained from Sigma-Aldrich (St. Louis, Mo., USA). Analytical grade formic acid was purchased from Spectrum Chemical Mfg. Corp. (New Brunswick, N.J., USA). The chemical standards deacetylasperulosidic acid (DAA) and asperulosidic acid (AA) were isolated from authentic noni fruit in our laboratory. Their identification and purities were determined by HPLC, Mass spectrometry, and NMR to be higher than 99% (data not shown). The chemical structures of DAA and AA are listed in FIG. 4. They were accurately weighed and then dissolved in an appropriate volume of MeOH to produce corresponding stock solutions. The working standard solution of DAA and AA for the calibration curve was prepared by diluting the stock solution with MeOH in seven concentration increments ranging from 0.00174-1.74 and 0.0016-0.80 mg/mL, respectively. All stock and working solutions were maintained at 0° C. in a refrigerator. The calibration curves of the standards were plotted after linear regression of the peak areas versus concentrations.

Conditions and Instrumentation

Chromatographic separation was performed on a Waters 2690 separations module coupled with 996 PDA detectors, equipped with an C18 column (4.6 mm×250 mm; 5 µm, Waters Corporation, Milford, Mass., USA). The pump was connected to two mobile phases: A; MeCN, and B; 0.1% formic acid in $H_2O$ (v/v), and eluted at a flow rate of 0.8 mL/min. The mobile phase was programmed consecutively in linear gradients as follows: 0-5 min, 0% A; and 40 min, 30% A. The PDA detector was monitored in the range of 210-400 nm. The injection volume was 10 µL for each of the sample solutions. The column temperature was maintained at 25° C. Data collection and integration were performed using Waters Millennium software revision 32.

Materials and Sample Preparation

Fresh noni fruit juice (sample A, FIG. 5) was squeezed from the noni fruit originally collected from the French Polynesia (Tahitian islands). One gram of the fresh fruit juice was diluted with 5 mL of $H_2O$-MeOH (1:1), and mixed thoroughly; the solution was collected into a 5 mL volumetric flask for HPLC analysis. Dried fruit, seed, root, leaf, and flower (samples B-F, FIG. 5) were collected from the Tahitian islands. These were grounded into powder, and extracted with MeOH-EtOH (1:1) twice with a sonicator for 30 min each time. The extracts were combined, filtered and then dried in a rotary evaporator under vacuum at 50° C. The dried extracts were re-dissolved with MeOH for HPLC analysis.

The raw noni fruit samples (FIG. 6) were collected from different areas, including the Tahitian islands, Tonga, Dominican Republic, Okinawa, Thailand, and Hawaii. The fruit samples were stored below 0° C. before use. The fruits were thawed and mashed. Two g of each mashed fruit was extracted twice with MeOH (125 mL, 30 min each) using a sonicator. The MeOH extract was dried under vacuum in a rotary evaporator. The dried MeOH extracts were re-dissolved with 10 mL of MeOH. Voucher specimens of noni samples are deposited in our lab.

Analytical Method Validation

The limits of detection (LOD) and quantitation (LOQ) were defined as the lowest concentrations of analytes in a sample that can be detected and quantified. These LOD and LOQ limits were determined on the basis of signal-to-noise ratios (S/N) of 3:1 and 10:1, respectively. The working solutions DAA and AA standards, for LOD and LOQ determinations, were prepared by serial dilution. The intra- and inter-day precision assays, as well as stability tests were performed by following the method applied to the sample analysis for 3 consecutive days. Repeatability is the degree of agreement between results, when experimental conditions are maintained as constant as possible, and is expressed as the relative standard deviation (RSD) of replicates.

In the study, intra- and inter-day precisions of the HPLC method were measured by triplicate injections of samples on 3 consecutive days. Accuracy of the method (recovery) was assessed by the recovery percentage of DAA and AA in the spiked samples. The noni fruit juices were spiked with standards at three different concentrations (equivalent to 50%, 100% and 150% concentration of DAA and AA in the samples). The recovery percentage was calculated using the ratio of concentration detected (actual) to those spiked (theoretical). Variation was evaluated by the relative standard deviation (RSD) of triplicate injections in the HPLC experiments.

Results and Discussion

Analytical Method Validation

The validation of the developed HPLC chromatographic method was conducted on the fresh noni juice to determine LOD, LOQ, linearity, intra-day and inter-day precisions, and accuracy (Tables 10-13). The selected MeCN—$H_2O$ gradient exhibited a good separation and symmetrical peak shapes of target analytes in the HPLC chromatograms. The LODs (S/N=3) and LOQs (S/N=10) for DAA and AA are 10.6 and 9.7 ng, and 34.8 and 32.0 ng, respectively. The linear regression equations for DAA and AA were calculated as: $y=1.443 \times 10^7 - 17342.2$ and $y=1.537 \times 10^7 - 40804.7$, respectively, where x is the concentration and y is the peak area. The results showed good linearity with correlation coefficients of 0.9994 and 0.9999 for DAA and AA, within the range of concentrations investigated. The intra- and inter-day precisions, as RSD's, of DAA and AA were less than 0.86% and 3.0%, respectively, indicating that DAA and AA were stable during investigation period. Under the established experimental conditions, percent recoveries of analytes DAA and AA were from 90.49% to 105.32%, with RSD ranging from 0.40-2.66% (Table 12). The results of the experiments are within tolerance ranges recommended in the guideline for dietary supplement issued by the Association of Analytical Communities (AOAC International, 2002). The characterization of iridoids DAA and AA in noni samples were conducted by comparing their HPLC retention times and UV maximum absorptions with these of standards (Table 10).

TABLE 10

Table 1. Chromatographic and spectroscopic characteristics of the iridoids

| Compounds | UV $\lambda_{max}$ (nm) | $R_t$ (min) | LOD (ng) | LOQ (ng) | Linearity range (mg/mL) |
|---|---|---|---|---|---|
| DAA[a] | 235.5 | 15.94 | 10.6 | 34.8 | 0.00174-1.74 |
| AA[b] | 235.5 | 26.08 | 9.7 | 32.0 | 0.0016-0.80 |

[a]Deacetylasperulosidic acid;
[b]asperulosidic acid.

TABLE 11

Table. 2 Intra- and inter-day precisions and stability assays for the quantitative determination of iridoids in noni by HPLC-PDA

| Samples | Day 1 | | Day 2 | | Day 3 | | Inter-day | |
|---|---|---|---|---|---|---|---|---|
| | Amount detected[a] | RSD (%) | Amount detected[a] | RSD (%) | Amount detected[a] | RSD (%) | Amount detected[a] | RSD (%) |
| DAA[b] | 1.308 | 0.86 | 1.291 | 0.43 | 1.291 | 0.62 | 1.297 | 0.86 |
| AA[c] | 0.276 | 1.16 | 0.281 | 3.00 | 0.287 | 1.84 | 0.281 | 2.49 |

[a]Mean ± SD, n = 3, mg/ml.;
[b]descetylasperulosidic acid;
[c]asperulosidic acid.

TABLE 12

Table 3. Accuracy assays for the quantitative determination of iridoids in noni by HPLC-PDA

| Samples | Concentration spiked[d] | Concentration detected[a,b] | Recovery Percentage (%) | RSD % |
|---|---|---|---|---|
| DAA[c] | 0.66 | 0.619 ± 0.016 | 93.84 | 2.66 |
| | 1.32 | 1.271 ± 0.019 | 96.29 | 1.53 |
| | 2.00 | 2.106 ± 0.009 | 105.32 | 0.40 |
| AA[a] | 0.146 | 0.132 ± 0.002 | 90.49 | 1.58 |
| | 0.291 | 0.273 ± 0.004 | 93.93 | 1.39 |
| | 0.437 | 0.433 ± 0.004 | 99.25 | 0.93 |

[a]Unit, mg/mL;
[b]mean ± SD; n = 3;
[c]deacetylasperulosidic acid;
[d]asperulosidic acid.

TABLE 13

Table 4. The concentration of major iridoids in different parts of noni

| Samples | DAA[a] | AA[b] |
|---|---|---|
| Fruit juice (mg/mL) | 1.441 ± 0.027 | 0.218 ± 0.009 |
| Fruit (dried) (mg/g) | 3.741 ± 0.016 | 1.253 ± 0.005 |
| Leaf (mg/g) | 0.338 ± 0.028 | 0.539 ± 0.007 |
| Root (mg/g) | 0.087 ± 0.008 | 0.326 ± 0.031 |
| Seed (mg/g) | 1.303 ± 0.050 | 0.148 ± 0.011 |
| Flower (mg/g) | 0.880 ± 0.040 | 0.421 ± 0.021 |

[a]Deacetylasperulosidic acid;
[b]asperulosidic acid; mean ± SD; n = 3.

Characterization and Quantitation of DAA and AA in Noni Different Plant Parts

Figure 5:
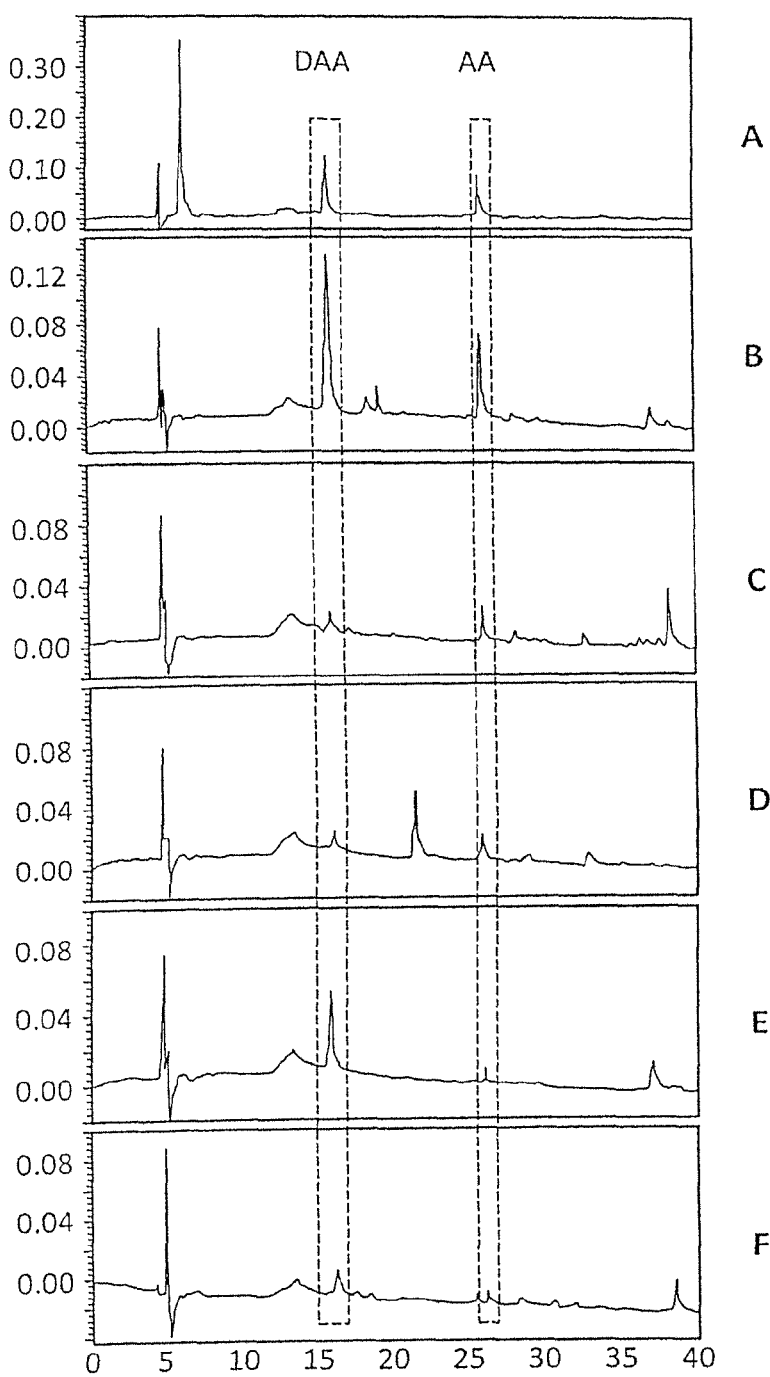
FIG. 5 depicts HPLC chromatograms of iridoid analysis in the different parts of noni plant.

Iridoids have been identified in noni fruit, leaf, and root previously. In our preliminary experiments, DAA and AA appear to be the major iridoids in most parts of the noni plant. As such, these two iridoids were employed for the quantitation and comparison of iridoid contents in different noni parts. The typical HPLC chromatograms of noni fruit, leaf, root, seed, and flower are shown in FIG. 5. The experimental results (Table 13) indicated that the DAA content in various parts of the plant are, in order of predominance, dried noni fruit>fruit juice>seed>flower>leaf>roots. For AA contents, the rank is dried noni fruit>leaf>flower>root>fruit juice>seed. Among the different plant parts, noni fruit (juice) seems a good source of iridoids. Iidoids, specifically deacetylasperulosidic acid and asperulosidic acid are the major secondary metabolites in noni fruit. As such, these may be responsible for its diverse health effects. For example, DAA and AA may have many biological activities, including anti-clastogenic, antiarthritic, antinociceptive, anti-inflammatory, cardiovascular, cancer-preventive, and anti-tumor effects. Toxicity tests suggested DAA and AA are non-genotoxic in mammalian cells.

Comparison of Iridoid Contents in Noni Fruits from Different Areas

Figure 6:
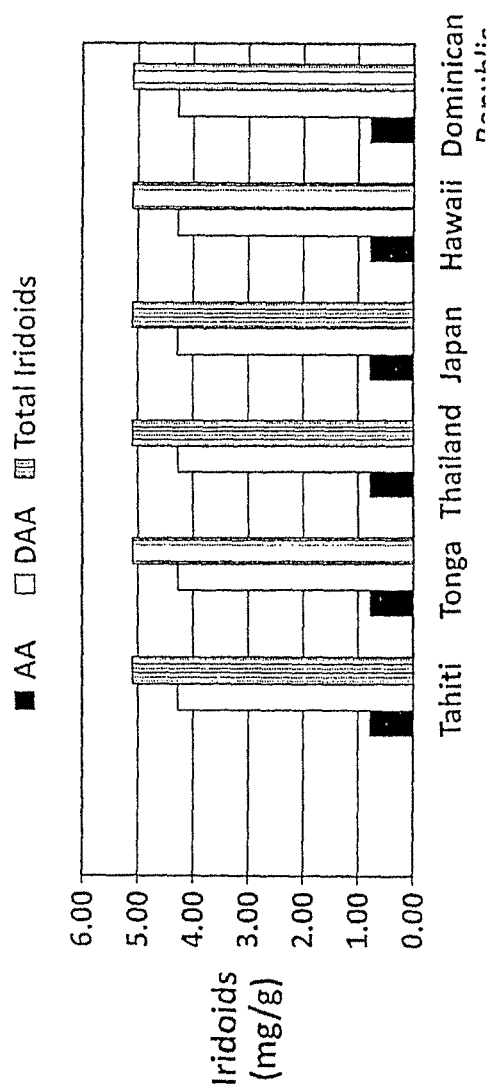
FIG. 6 depicts a comparison of iridoid contenst in the methanolic extracts of noni fruits collected from different tropical areas worldwide.

To evaluate the impact of geographical environments (soil, sunlight, temperature, precipitation, etc.) on the iridoid contents in noni fruit, analyses were performed on noni fruits cultivated and collected from different tropical regions worldwide. Ripe noni fruit samples were kept frozen during shipment. Further, MeOH extracts were analyzed to control for moisture variations. FIG. 6 shows a comparison of DAA, AA, and total iridoids (DAA+AA) in different noni fruits. The concentration ranges of DAA and AA in the MeOH extracts were 13.8-42.9 mg/g and 0.7-8.9 mg/g, respectively. Moreover, noni fruit collected from French Polynesia had the highest amount of the total iridoids, and noni fruit from the Dominican Republic contained the least. The results showed that geographical factors have significant effects on the iridoid contents in noni fruits. As such, different pharmacological activities may be expected to noni fruits collected from various areas.

The Impact of Pasteurization on DAA Content

Noni fruit juice is usually subjected to heat pasteurization during commercial processing. Pasteurization is usually employed in noni industry, i.e., heating up to 87.7° C. for several seconds. In this study, the stability of DAA was conducted. DAA was exposed to 90° C. at pH 3.3 for one minute to determine its thermal stability at acidic conditions. The results indicated that there was no difference in the DAA contents before and after heating, indicating that DAA is stable under the pasteurization conditions.

Example Five

Noni fruits were harvested in French Polynesia and allowed to fully ripen. The fruit was then processed into a puree by mechanical removal of the seeds and skin at a good manufacturing certified fruit processing facility in Mataiea, Tahiti. Olive leaf extract was prepared by extraction of dried *O. europaea* leaves with ethanol, followed by removal of the solvent and residual water by evaporation. The resulting extract was reduced to a powder with a particle size <0.420 mm and total moisture <6%. Ripe *C. mas* and *C. officinalis* fruits were harvested during the autumn season. *C. mas* fruit was harvested in the Anatolia region of Turkey, whereas *C. officinalis* fruit was harvested in the Shaanxi and Hunan provinces of China. The seed pits were removed from fruit with automatic fruit pitters. Batches of *C. mas* fruit were processed into puree in an auger press micro-mesh (4 mm) screen fruit pulper. Depitted *C. officinalis* fruits were dried at low heat and then shipped to the U.S. where the reconstituted juice was extracted by pumping/filtration through a stainless steel mesh screen. All ingredients were blended and pasteurized at a good manufacturing certified fruit processing facility in American Fork, Utah to produce the finished product used in this study, Thrive Adaptogenics Max (Morinda Bioactives, Utah, USA). The total solids content (mean±standard deviation) of the final test product was 20.24±0.48%.

Iridoid Analysis

Samples from separate batches were analyzed. Analysis for iridoids was performed by high performance liquid chromatography (HPLC), according to a previously reported method (Deng et al., 2011). Prior to analysis, one g of sample was dissolved in 10 mL 1:1 (v/v) water:methanol and then filtered through a 0.2 μm PTFE filter. Iridoid standards were dissolved in methanol (MeOH) to a concentration of 1 mg/mL and further diluted to produce standard curves for iridoids identified in the samples. Chromatographic separations were performed on a Waters 2690 separations module coupled with 996 PDA detectors (Waters Corporation, Milford, Mass., USA), equipped with a C18 column. Elution was accomplished with two mobile phases, MeCN and 0.1% formic acid in $H_2O$ (v/v), with a flow rate of 0.8 mL/min. A linear gradient of 100% aqueous formic acid (0.1%) for 0-5 min, followed by 70% aqueous formic acid and 30% MeCN for 40 min, was used. The PDA detector was monitored in the range of 210-400 nm. The injection volume was 10 μL for each of the sample solutions. The column temperature was maintained at 25° C. Iridoids were identified in the samples by comparison of retention times and UV absorbance of compounds in the samples and the standards.

2,2-Diphenylpicrylhydrazyl (DPPH) Radical Scavenging Assay

In the DPPH test, the beverage was diluted serially with deionized water. The diluted samples, and a water blank, were combined 1:1 (v/v) with 0.4 mM DPPH in ethanol. The absorbance of each sample, in triplicate, and blank was read at 515 nm with a Synergy™ HT microplate reader (BioTek Instruments, Inc., Winooski, Vt., USA) after incubation at 25±2° C. for 60 minutes. Percent radical scavenging activity was calculated by dividing the difference in absorbance of the blank and the sample by the absorbance of the blank alone. The concentration of Thrive Adaptogenics Max which scavenged 50% of the DPPH radicals ($IC_{50}$) was calculated with the linear equation that best fit the plot of concentration versus scavenging activity ($R^2 > 0.99$).

Efficacy in Type 2 Diabetic Sprague Dawley (SD) Rats

Fifty healthy male SD rats, 200-220 g, were acquired from the Tianjin Drug Research Center (Tianjin, China). These were acclimated for one week while receiving standard rodent feed, composed of 23% protein, 53% carbohydrates, and 5% fat. Following acclimation, the rats were randomly divided into five groups of 10 animals each. One group, the normal control, continued to be fed the standard diet. The four other groups were fed a high fat and sugar diet composed of 20% protein, 48% carbohydrates, and 22% fat. Water and feed were provided ad libitum. The normal control group and one of the groups receiving the high fat diet, the diabetic controls, were fed 2 mL saline twice per day by gavage. The remaining three groups received, twice daily by gavage, 2 mL of solutions containing 25% (low dose), 50% (mid dose), or 100% (high dose) Thrive Adaptogenics Max. All animals were fed saline or test product solutions at the same time every morning and evening. After four weeks of the various treatments and feeding of the assigned diets, the animals were fasted for 12 hours and administered a single abdominal injection, at 30 mg/kg body weight (b.w.), of 0.5% streptozotocin in citrate buffer (pH 4.2). The normal control animals did not receive the streptozotocin solution, but were administered citrate buffer only. All groups were provided water and the standard diet for another 7 days then fasted over night.

On the final day of the study (day 35), all animals received an abdominal injection of glucose solution at 2 g/kg b.w. Glucose levels in blood from the tail vein of each animal were measured with a glucometer (Changsha Sannuo Biologic & Sensing Technology, Inc., Changsha, Hunan, China) at 0 and 2 hours after glucose injection. Following the glucose test, the rats were anesthetized with ether, and 1.5 mL blood was removed from the orbital sinus. For the detection of T-cell subsets, 1 mL blood was mixed with heparin. For detection of AGEs, 0.5 mL blood was centrifuged at 3000 rpm for 10 minutes, followed by collection of the serum.

Heparinized blood samples were prepared for flow cytometry analysis with a T cell subset detection kit (MultiSciences Biotech Co., Ltd., Hangzhou, Zejiang, China). This involved labeling of specific lymphocytes with fluorescently-labeled antibodies for $CD3^+$, $CD4^+$, and $CD8^+$ proteins, according to the kit manufacturer's instructions. Labeled cells were detected with a flow cytometer (Beckman Coulter, Brea, Calif., USA), and the percentages of $CD3^+$, $CD4^+$, and $CD8^+$ T-cell subsets were determined. The $CD4^+/CD8^+$ ratios were also calculated. Centrifuged blood samples were prepared for AGE detection with an enzyme linked immunosorbent assay (ELISA) kit (Shanghai YanHui Biotechnical, Inc., Shanghai, China), according to the kit manufacturer's instructions. Fluorescent detection of labeled AGE's was performed with a Bio-Rad 550 microplate ELISA reader (Bio-Rad, Hercules, Calif., USA). Animal weights were also recorded throughout the study.

The means and standard deviations of each measurement were calculated for each group. Statistical differences between control and test groups were evaluated with Student's t-test, using SPSS® software version 16.0 (IBM Corporation, Armonk, N.Y., USA).

Results and Discussion

Iridoid Analysis

The phytochemical analysis revealed that Thrive Adaptogenics Max is an iridoid rich beverage, with total iridoid content (mean±standard deviation) of 2.09±0.08 mg/mL. The major iridoids present were identified as asperulosidic acid, deacetylasperulosidic acid, oleuropein, morroniside, loganic acid, and loganin. Noni fruit puree is the source of asperulosidic acid and deacetylasperulosidic acid (West et al., 2011). Oleuropein is a well known and well researched iridoid in noni leaf extract (Japon-Lujan et al., 2006). Morroniside and loganin are contributed primarily by *C. officinalis* fruit (Gu et al., 1996; Du et al., 2008). Our analysis resulted in the first discovery of loganic acid in *C. mas* fruit. The concentrations found in the beverage indicate that processing conditions are suitable for the preservation of the iridoids.

DPPH Radical Scavenging Assay

In the DPPH radical scavenging assay, remarkably high in vitro antioxidant activity was observed, with an $IC_{50}$ of 3.8 μL/mL. The antioxidant activity of this beverage is much greater than those reported for several fruits and fruit juices. The $IC_{50}$'s reported for mangosteen, orange, pomelo, grapes, and papaya ranged from 11.18-32.80 mg/mL, while those of orange juice, grape, rose apple, and jackfruit were from 50.62-110.46 mg/mL (Surinut et al., 2005). Different varieties of pomegranate juice are also reported to have a lower $IC_{50}$'s, ranging from 15.98-23.98 μL/mL (Elfalleh et al., 2009). The DPPH radical scavenging activity of Thrive Adaptogenics Max is at least three times greater than that reported for any of these other fruit products.

Efficacy in Type 2 Diabetic Rats

Average weights throughout the study are summarized in FIG. 7. There were no differences in the initial weights of the groups. However, significant differences from normal controls were evident by week 2 in the diabetic control and low dose groups. At the same time point, mid and high dose group weights were no different than those of normal controls. At week 4, high dose group weights were not significantly different from those of normal controls. During the entire study, weight gain was greatest in the diabetic control group, which received no test product. Significant reductions in weight gain of the high and mid dose groups, as compared to the diabetic control group, were also apparent throughout the entire study. A trend of lower weight was also present in the low dose group, reaching statistical significance at week 4. Overall, weight differences were dose-dependent and demonstrated that supplementation with the test product reduced weight gain in rats fed a high fat and high sugar diet.

Blood glucose levels at 0 and 2 hours after glucose injection, or challenge, are presented in FIG. 8. Glucose levels in all groups fed the high fat and sugar diet were significantly greater than the normal control group. But significant dose-dependent reductions in blood glucose, as compared to the diabetic controls, were seen in the low, mid and high dose groups. Animals with 0 and 2 hour glucose levels >7.0 and >11.0 mmol/L, respectively, were categorized as diabetic. The percentage of animals categorized as diabetic in each group is also presented in FIG. 8. All animals in the diabetic control group were above these limits, demonstrating the successful induction of diabetes. As with mean blood glucose, a dose-dependent decrease in the percentage of diabetic rats occurred in the test product groups. It is remarkable that no animals met the diabetic threshold in the high dose group.

T cell subsets in each group are summarized and compared in FIG. 9. The percentage of T cells among total lymphocytes is expressed by $CD3^+$ values. $CD4^+$ cells are T helper cells that play a central role in regulating the immune system, whereas $CD8^+$ cells (cytotoxic or suppressor cells T cells) down regulate immune function (Hung et al. 1998; Jiang and Chess, 2006; WHO, 2007). The $CD4^+/CD8^+$ ratio, also referred to as the T-lymphocyte helper/suppressor profile, is an indicator of immune system function. In a properly functioning immune system, this ratio is greater than one, as $CD4^+$ cell count should be greater than $CD8^+$. Reductions in $CD4^+/CD8^+$ ratios have been associated with immune deficiency (Reinherz and Schlossman, 1980; Kiecolt-Glaser et al., 1986). Human studies have demonstrated an inverse association between T helper cell percentage and the severity (in HbA1C levels) and duration of type 2 diabetes (Sumida, 1991). A similar reduction in relative $CD4^+$ count was also observed in patients progressing towards onset of type 1 diabetes (Al-Sakkaf et al., 1989). As revealed in FIG. 9, $CD3^+$, $CD4^+$, and $CD4^+/CD8^+$ values are significantly lower in all the diabetic groups than in the normal control group, with the exception of the high dose group. $CD4^+$ and $CD8^+$ percentages in the high dose group, as well as the $CD4^+/CD8^+$ ratio, were not significantly different than those in the normal control group. Further, there was a trend of increased total $CD3^+$ cells with increased test product dose, with high dose values being significantly greater than those in the diabetic control group. A similar trend was observed with $CD4^+$ values and $CD4^+/CD8^+$ ratios, with statistically significant increases occurring in the mid and high dose groups. $CD8^+$ percentages were greatest in the diabetic control group. However, these decreased as test product dose increased. As $CD8^+$ percentage is inversely associated with $CD4^+$ percentage, the changes are expected. The $CD8^+$ percentage in the high dose group is significantly less than that of the diabetic control group. These changes demonstrate improvements in immune system function that occur with increased ingestion of the test product.

Serum AGE levels were highest in the diabetic control group, FIG. 10. As expected, AGEs were lowest in normal controls. Interestingly, there was no significant difference between the level in this group and that of the high dose group. Further, the mid dose also had significantly lower AGEs than the diabetic controls. As such, a dose dependent trend of reduced AGEs was evident in the groups receiving the test product. AGEs, products of nonenzymatic glycation of proteins (Maillard reaction), accumulate during aging and in a number of diseased states, such as diabetes, chronic inflammation, and kidney failure (Ramasamy et al., 2005). AGE formation occurs over extended periods of time and is associated with elevated glucose levels (Singh et al., 2001). Therefore, the reduction in blood glucose levels by the test product may be a major reason for lower AGEs. AGE formation is also accelerated by oxidative stress (Miyata et al., 1997). It is likely, therefore, that the antioxidant activity of the test product helps control AGE levels. Cross-links formed between intra and extracellular molecules and AGEs lead to a wide variety of health complications, due to altered cell structure and function and the induction of inflammation (Goldin et al., 2006; Naidoo et al., 2011). Therefore, controlling AGE formation may slow the progression of pathologies associated with aging and deviations from normal metabolism, such as metabolic syndrome and diabetes (Lee and Cerami, 1994; Kitano et al., 2004; Peppa and Vlassara, 2005).

Example Five Conclusion

The combination of noni, Cornelian cherries, and olive leaf extract appears to have significant potential for improving and maintaining health. The iridoid rich beverage may help mitigate adverse health effects associated with the aging process, something that confronts all people. Those with metabolic imbalances, such as diabetes and metabolic syndrome, may also benefit from supplementation with the beverage. People with metabolic syndrome constitute a large segment of the population. Its prevalence among developed nations, such as the US and the European Union, is ever increasing (Ford et al., 2004). In 2006, 34% of the US adult population met the criteria for metabolic syndrome (Ervin, 2009). Surprisingly, similar percentages were reported for adult males in the Okayama Prefecture of Japan (Miyatake et al., 2006). Metabolic syndrome is also an increasing public health problem in emerging economies, such as Malaysia and Russia (Tan et al., 2011; Metelskaya et al. 2011), and effective interventions may have a major impact on these populations.

CONCLUSION

A selective analytical HPLC method has been developed and validated for analysis of iridoids in noni. Iridoids, specifically deacetylasperulosidic acid and asperulosidic acid, are identified as the major components in noni fruit, and also present in leaf, root, seed, and flower of the noni plant. Geographical factors seem to influence iridoid content of the fruit. Noni iridoids are stable during pasteurization. Therefore, the method reported herein may provide an accurate and rapid tool in the qualitative and quantitative analysis of noni and its commercial products.

What is claimed is:

1. A formulation comprising, by weight of the formulation:
   *Morinda citrifolia* fruit juice in amount by weight between about 0.1 and 80 percent, *Cornus mas* puree in amount by weight between 0.1 and 80 percent, *Cornus officinalis* juice in amount by weight between 0.1 and 80 percent, *Vitis vinifera* juice concentrate in an amount by weight between 0.1 and 80 percent, *Vaccinium corymbosum* juice in an amount by weight of about 1.0 and 80 percent, *Prunus cerasus* juice concentrate in an amount by weight about 0.1 and 30 percent, *Vitis labrusca* juice concentrate in an amount by weight of about 0.1 to 30 percent, *Olea europea* leaf extract in an amount by weight of about 1.0 percent, *Vaccinium macrocarpon* juice concentrate in an amount by weight of about 1.0 percent and natural flavors in an amount by weight of about 1.0 percent.

2. A formulation comprising, by weight of the formulation:
   *Morinda citrifolia* fruit juice in amount by weight between about 0.1 and 80 percent, *Cornus mas* puree in amount by weight between 0.1 and 80 percent, *Vitis vinifera* juice concentrate in an amount by weight between 0.1 and 80 percent, *Vaccinium corymbosum* juice in an amount by weight of about 1.0 and 80 percent, *Prunus cerasus* juice concentrate in an amount by weight about 0.1 and 30 percent, *Vitis labrusca* juice concentrate in an amount by weight of about 0.1 to 30 percent, *Olea europea* leaf extract in an amount by weight of about 1.0 percent, *Vaccinium macrocarpon* juice concentrate in an amount by weight of about 1.0 percent and natural flavors in an amount by weight of about 1.0 percent.

3. A formulation comprising, by weight of the formulation:
   *Morinda citrifolia* fruit juice in amount by weight between about 0.1 and 80 percent, *Cornus officinalis* juice in amount by weight between 0.1 and 80 percent, *Vitis vinifera* juice concentrate in an amount by weight between 0.1 and 80 percent, *Vaccinium corymbosum* juice in an amount by weight of about 1.0 and 80 percent, *Prunus cerasus* juice concentrate in an amount by weight about 0.1 and 30 percent, *Vitis labrusca* juice concentrate in an amount by weight of about 0.1 to 30 percent, *Olea europea* leaf extract in an amount by weight of about 1.0 percent, *Vaccinium macrocarpon* juice concentrate in an amount by weight of about 1.0 percent and natural flavors in an amount by weight of about 1.0 percent.

* * * * *